United States Patent
Abbasian et al.

(10) Patent No.: US 11,401,336 B2
(45) Date of Patent: Aug. 2, 2022

(54) BCMA-BINDING ANTIBODIES AND USES THEREOF

(71) Applicant: CELGENE CORPORATION, Summitt, NJ (US)

(72) Inventors: Mahan Abbasian, San Diego, CA (US); Henry Chan, Poway, CA (US); Kandasamy Hariharan, San Diego, CA (US); Jeonghoon Sun, San Francisco, CA (US); Andrew Wurmser, San Diego, CA (US)

(73) Assignee: CELGENE CORPORATION, Summit, NJ (US)

( * ) Notice: Subject to any disclaimer, the term of this patent is extended or adjusted under 35 U.S.C. 154(b) by 0 days.

(21) Appl. No.: 16/971,925

(22) PCT Filed: Feb. 20, 2019

(86) PCT No.: PCT/US2019/018698
§ 371 (c)(1),
(2) Date: Aug. 21, 2020

(87) PCT Pub. No.: WO2019/164891
PCT Pub. Date: Aug. 29, 2019

(65) Prior Publication Data
US 2020/0399386 A1    Dec. 24, 2020

Related U.S. Application Data

(60) Provisional application No. 62/633,152, filed on Feb. 21, 2018.

(51) Int. Cl.
*C07K 16/28*    (2006.01)
(52) U.S. Cl.
CPC .... *C07K 16/2878* (2013.01); *C07K 2317/565* (2013.01)
(58) Field of Classification Search
CPC .................................................. C07K 16/2878
See application file for complete search history.

(56) References Cited

U.S. PATENT DOCUMENTS

2010/0196388 A1*  8/2010  Jenkins .................. A61P 25/28
                                                        424/142.1
2016/0297885 A1   10/2016  Kuo et al.

FOREIGN PATENT DOCUMENTS

| WO | 2012163805 A1 | 12/2012 |
| WO | 2014089335 A2 | 6/2014 |
| WO | 2016014565 A1 | 1/2016 |
| WO | 2016094304 A2 | 6/2016 |
| WO | 2016166630 A1 | 10/2016 |
| WO | 2017021450 A1 | 2/2017 |
| WO | 2017223111 A1 | 12/2017 |

OTHER PUBLICATIONS

Carpenter, R. O., et al., "B-cell Maturation Antigen Is a Promising Target for Adoptive T-cell Therapy of Multiple Myeloma", Apr. 15, 2013 (Apr. 15, 2013), vol. 19, No. 8, p. 2048-2060.
Carlos A. Ramos, et al., "CAR-T Cell Therapy for Lymphoma", Annual Review of Medicine : Selected Topics in the ClinicalSciences,vol. 67, No. 1, Jan. 14, 2016 (Jan. 14, 2016), p. 165-183.
International Search Report of PCT/US2019/018698, dated Jun. 12, 2019.

* cited by examiner

*Primary Examiner* — Amy E Juedes
*Assistant Examiner* — Peter Johansen
(74) *Attorney, Agent, or Firm* — Eckert Seamans Cherin & Mellott, LLC

(57) ABSTRACT

Antibody species that bind B-Cell Maturation Antigen (BCMA) are provided as well as methods of depleting BCMA-expressing cells in a patient in need thereof, comprising administering a therapeutically effective amount of the antibody species or an entity comprising a BCMA binding fragment thereof. Methods of treating B cell-related disorders associated with BCMA expression in a patient in need thereof are provided, comprising administering to the patient a therapeutically effective amount of the antibody species or an entity comprising a BCMA binding fragment thereof.

18 Claims, 10 Drawing Sheets

Specification includes a Sequence Listing.

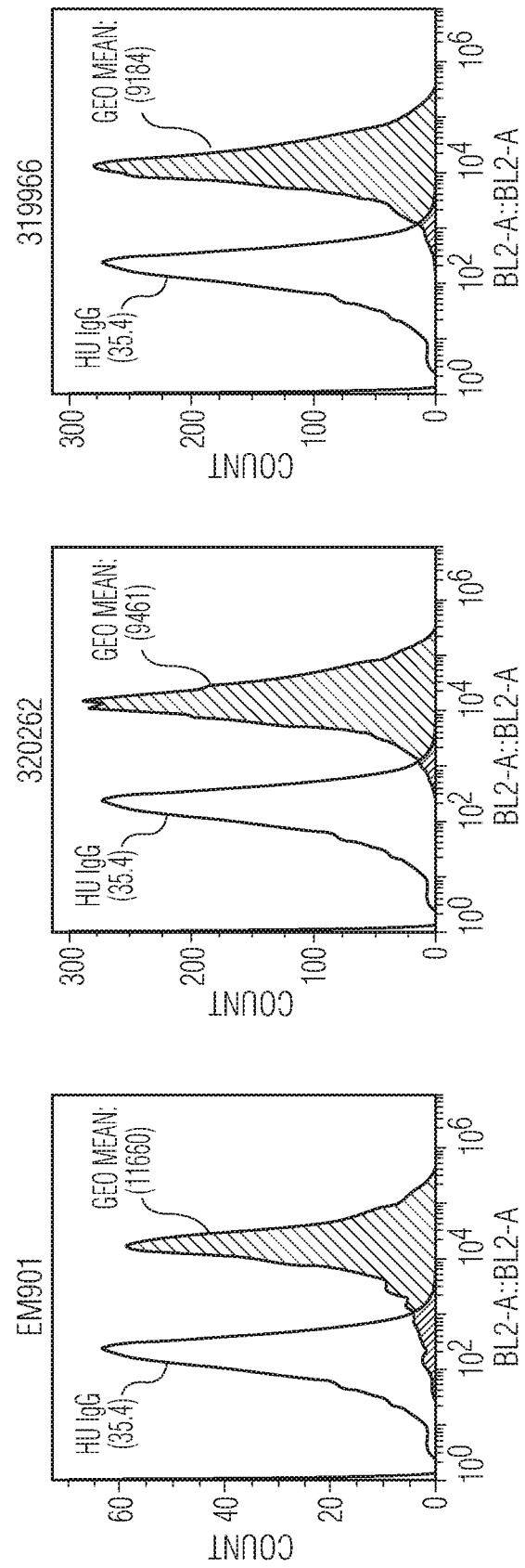

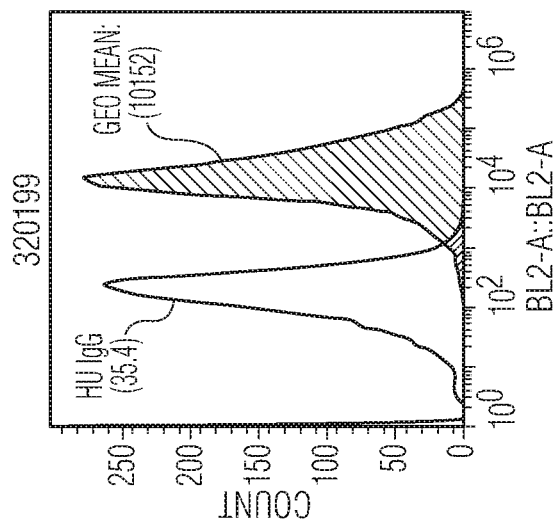
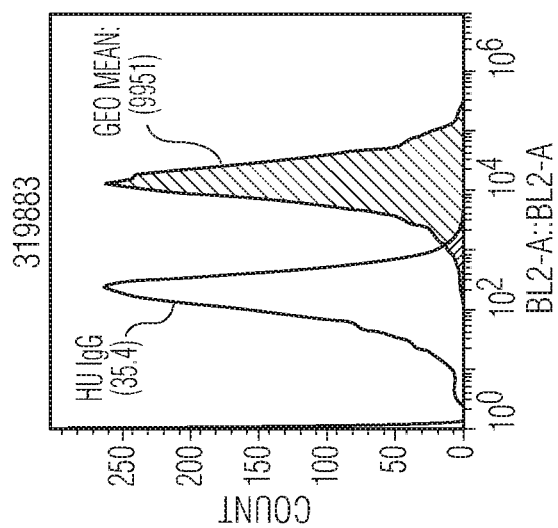
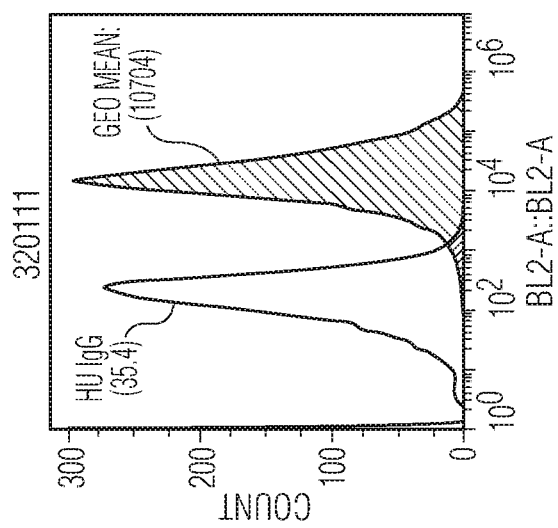
FIG. 2D
FIG. 2E
FIG. 2F

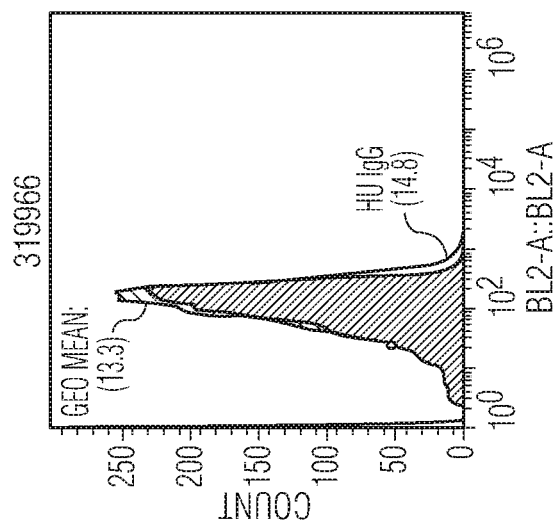
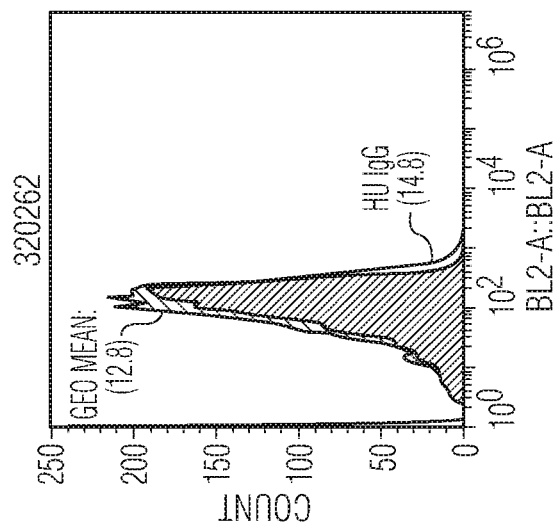
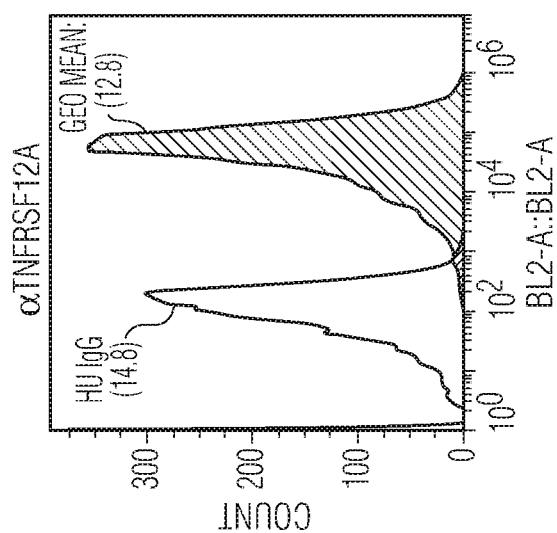

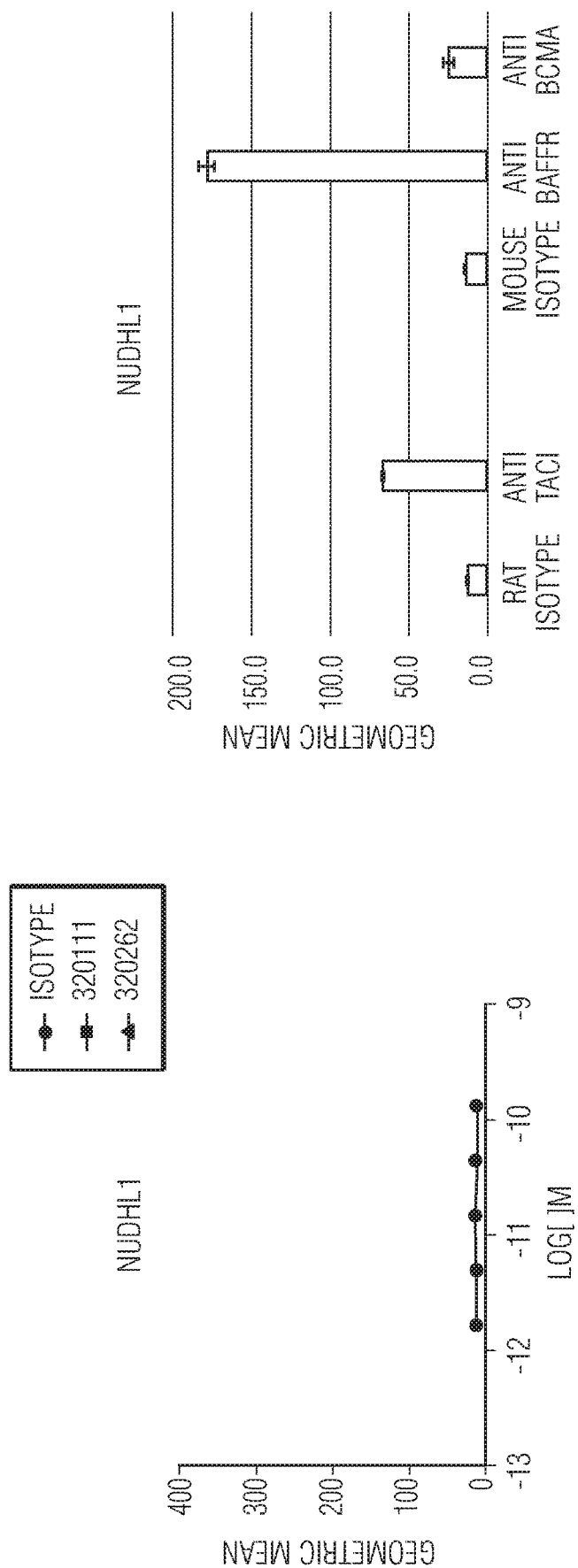

BCMA-BINDING ANTIBODIES AND USES THEREOF

CROSS-REFERENCE TO RELATED APPLICATIONS

This application is a U.S. National Phase of International Application No. PCT/US2019/018698, filed. Feb. 20, 2019, which claims priority to U.S. Provisional Patent Application No. 62/633,152 filed Feb. 21, 2018, each of which are incorporated herein by reference in their entirety.

1. SEQUENCE LISTING

The instant application contains a Sequence Listing which has been submitted electronically in ASCII format via EFS-Web and is hereby incorporated by reference in its entirety. Said ASCII copy, created on Feb. 2, 2022, is named 298068-00340_Sequence_Listing.txt and is 23,075 bytes in size.

2. FIELD

The present disclosure related to isolated antibodies or fragments thereof that bind to B-Cell Maturation Antigen (BCMA), polynucleotides encoding the antibodies or fragments, host cells producing the antibodies or fragments, and methods of use or treatment using the antibodies or fragments.

3. BACKGROUND

BCMA (B-cell maturation antigen; also designated as TNFRSF17 or CD269) is a transmembrane protein belonging to the TNF receptor super family. BCMA is a B-cell marker that is essential for B-cell development and homeostasis due to its interaction with its ligands BAFF (B cell Activation Factor of TNF Family; also designated TALL-1 or TNFSF13B) and APRIL (A Proliferation-Inducing Ligand).

BCMA expression is understood to be restricted to the B-cell lineage and is mainly present on plasma cells and plasmablasts, and to some extent on memory B-cells, but is virtually absent on peripheral and naive B-cells. Together with its family members Transmembrane Activator and Cyclophylin ligand Interactor (TACI) and B cell Activation Factor of TNF Family receptor (BAFF-R), BCMA regulates different aspects of humoral immunity, B-cell development and homeostasis.

BCMA is also expressed on multiple myeloma (MM) cells. BCMA appears to support growth and survival of multiple myeloma (MM) cells. MM cell lines and freshly isolated MM cells typically express BCMA and TACI protein on their cell surfaces and have variable expression of BAFF-R protein on their cell surface. Multiple myeloma is the second most common hematological malignancy, constituting 2% of all cancer deaths. MM is a heterogeneous disease and caused by mostly by chromosome translocations, including t(11;14), t(4;14), t(8;14), del(13), and del (17). MM-affected patients may experience a variety of disease-related symptoms due to, and including, bone marrow infiltration, bone destruction, renal failure, immunodeficiency, and the psychological burden of a cancer diagnosis.

Current therapies used to treat multiple myeloma are usually not curative. Stem cell transplantation may not be an option for many patients because of advanced age, presence of other serious illness, or other physical limitations. Chemotherapy only partially controls multiple myeloma, and it rarely leads to complete remission. As such, there is a need for new, innovative treatments for multiple myeloma, and for other plasma cell- or B cell-related diseases or disorders.

4. SUMMARY

In a first aspect, provided herein is an antibody that binds to B-Cell Maturation Antigen (BCMA), or a BCMA-binding fragment thereof, comprising heavy chain CDR1, CDR2 or CDR3 sequences of: SEQ ID NO:7, SEQ ID NO:8, and SEQ ID NO:9, respectively; SEQ ID NO:10, SEQ ID NO:11 and SEQ ID NO:12, respectively; SEQ ID NO:13, SEQ ID NO:14 and SEQ ID NO:15, respectively; SEQ ID NO:18, SEQ ID NO:19 and SEQ ID NO:20, respectively; SEQ ID NO:21, SEQ ID NO:22 and SEQ ID NO:23, respectively; SEQ ID NO:24, SEQ ID NO:25 and SEQ ID NO:26, respectively; SEQ ID NO:29, SEQ ID NO:30 and SEQ ID NO:31, respectively; SEQ ID NO:32, SEQ ID NO:33 and SEQ ID NO:34, respectively; SEQ ID NO:35, SEQ ID NO:36 and SEQ ID NO:37, respectively; SEQ ID NO:40, SEQ ID NO:41 and SEQ ID NO:42, respectively; SEQ ID NO:43, SEQ ID NO:44 and SEQ ID NO:45, respectively; SEQ ID NO:46, SEQ ID NO:47 and SEQ ID NO:48, respectively; SEQ ID NO:51, SEQ ID NO:52 and SEQ ID NO:53, respectively; SEQ ID NO:54, SEQ ID NO:55 and SEQ ID NO:56, respectively; or SEQ ID NO:57, SEQ ID NO:58 and SEQ ID NO:59, respectively. In a specific embodiment, the antibody additionally comprises the light chain CDR1, CDR2 or CDR3 sequences of SEQ ID NO:2, SEQ ID NO:3 or SEQ ID NO:4, respectively. In another specific embodiment, the antibody additionally comprises light chain CDR1, CDR2 and CDR3 sequences of SEQ ID NO:2, SEQ ID NO:3 and SEQ ID NO:4, respectively.

In specific embodiment, provided herein is an antibody that binds to BCMA, or a BCMA-binding fragment thereof, comprising a light chain comprising CDR1, CDR2 or CDR3 sequences of SEQ ID NO:2, SEQ ID NO:3 and SEQ ID NO:4, respectively, and heavy chain CDR1, CDR2 and CDR3 sequences of SEQ ID NO:7, SEQ ID NO:8, and SEQ ID NO:9, respectively; SEQ ID NO:10, SEQ ID NO:11, and SEQ ID NO:12, respectively; or SEQ ID NO:13, SEQ ID NO:14 and SEQ ID NO:15, respectively.

In another specific embodiment, provided herein is an antibody that binds to BCMA, or a BCMA-binding fragment thereof, comprising a light chain comprising CDR1, CDR2 or CDR3 sequences of SEQ ID NO:2, SEQ ID NO:3 and SEQ ID NO:4, respectively, and heavy chain CDR1, CDR2 and CDR3 sequences of SEQ ID NO:18, SEQ ID NO:19 and SEQ ID NO:20, respectively; SEQ ID NO:21, SEQ ID NO:22 and SEQ ID NO:23, respectively; or SEQ ID NO:24, SEQ ID NO:25 and SEQ ID NO:26, respectively.

In another specific embodiment, provided herein is an antibody that binds to BCMA, or a BCMA-binding fragment thereof, comprising a light chain comprising CDR1, CDR2 or CDR3 sequences of SEQ ID NO:2, SEQ ID NO:3 and SEQ ID NO:4, respectively, and heavy chain CDR1, CDR2 and CDR3 sequences of SEQ ID NO:29, SEQ ID NO:30 and SEQ ID NO:31, respectively; SEQ ID NO:32, SEQ ID NO:33 and SEQ ID NO:34, respectively; or SEQ ID NO:35, SEQ ID NO:36 and SEQ ID NO:37, respectively.

In another specific embodiment, provided herein is an antibody that binds to BCMA, or a BCMA-binding fragment thereof, comprising a light chain comprising CDR1, CDR2 or CDR3 sequences of SEQ ID NO:2, SEQ ID NO:3 and SEQ ID NO:4, respectively, and heavy chain CDR1, CDR2 and CDR3 sequences of SEQ ID NO:40, SEQ ID NO:41 and SEQ ID NO:42, respectively; SEQ ID NO:43, SEQ ID NO:44 and SEQ ID NO:45, respectively; or SEQ ID NO:46, SEQ ID NO:47 and SEQ ID NO:48, respectively.

In another specific embodiment, provided herein is an antibody that binds to BCMA, or a BCMA-binding fragment thereof, comprising a light chain comprising CDR1, CDR2 or CDR3 sequences of SEQ ID NO:2, SEQ ID NO:3 and SEQ ID NO:4, respectively, and heavy chain CDR1, CDR2 and CDR3 sequences of SEQ ID NO:51, SEQ ID NO:52 and SEQ ID NO:53, respectively; SEQ ID NO:54, SEQ ID NO:55 and SEQ ID NO:56, respectively; or SEQ ID NO:57, SEQ ID NO:58 and SEQ ID NO:59, respectively.

In another more specific embodiment of any of the above antibodies or BCMA-binding fragments thereof, the antibody or BCMA-binding fragment thereof comprises a light chain variable domain amino acid sequence at least 80%, at least 85%, at least 90%, at least 95%, at least 96%, at least 97%, at least 98%, at least 99%, or 100% identical to SEQ ID NO:1 and a heavy chain variable domain amino acid sequence at least 80%, at least 85%, at least 90%, at least 95%, at least 96%, at least 97%, at least 98%, at least 99%, or 100% identical to SEQ ID NO:6, SEQ ID NO:17, SEQ ID NO:28, SEQ ID NO:39, or SEQ ID NO:50.

In a more specific embodiment of any of the above antibodies or BCMA-binding fragments thereof, the antibody or BCMA-binding fragment thereof comprises the light chain variable domain amino acid sequence of SEQ ID NO:1, or a light chain variable domain amino acid sequence at least 80%, at least 85%, at least 90%, at least 95%, at least 96%, at least 97%, at least 98%, or at least 99% identical to SEQ ID NO:1. In another more specific embodiment of any of the above antibodies or BCMA-binding fragments thereof, the antibody or BCMA-binding fragment thereof comprises the heavy chain variable domain amino acid sequence of SEQ ID NO:6, SEQ ID NO:17, SEQ ID NO:28, SEQ ID NO:39, or SEQ ID NO:50, or a heavy chain variable domain amino acid sequence at least 80%, at least 85%, at least 90%, at least 95%, at least 96%, at least 97%, at least 98%, or at least 99% identical to SEQ ID NO:6, SEQ ID NO:18, SEQ ID NO:28, SEQ ID NO:39, or SEQ ID NO:50. In another more specific embodiment of any of the above antibodies or BCMA-binding fragments thereof, the antibody or BCMA-binding fragment thereof comprises a light chain variable domain amino acid sequence at least 80%, at least 85%, at least 90%, at least 95%, at least 96%, at least 97%, at least 98%, at least 99%, or 100% identical to SEQ ID NO:1 and a heavy chain variable domain amino acid sequence at least 80%, at least 85%, at least 90%, at least 95%, at least 96%, at least 97%, at least 98%, at least 99%, or 100% identical to SEQ ID NO:6, SEQ ID NO:17, SEQ ID NO:28, SEQ ID NO:39, or SEQ ID NO:50.

In a more specific embodiment of any of the above antibodies or BCMA-binding fragments thereof, the antibody or BCMA-binding fragment thereof comprises a light chain variable domain amino acid sequence that comprises the amino acid sequence of SEQ ID NO:2, SEQ ID NO:3 and SEQ ID NO:4, and is at least 80%, at least 85%, at least 90%, at least 95%, at least 96%, at least 97%, at least 98%, or at least 99% identical to SEQ ID NO:1. In other more specific embodiments of any of the above antibodies or BCMA-binding fragments thereof, the antibody or BCMA-binding fragment thereof comprises a heavy chain variable domain amino acid sequence of SEQ ID NOS:7-9, 10-12 or 13-15, and is at least 80%, at least 85%, at least 90%, at least 95%, at least 96%, at least 97%, at least 98%, or at least 99% identical to SEQ ID NO:6; the antibody or BCMA-binding fragment thereof comprises a heavy chain variable domain amino acid sequence of SEQ ID NOS:18-20, 21-23, or 24-26, and is at least 80%, at least 85%, at least 90%, at least 95%, at least 96%, at least 97%, at least 98%, or at least 99% identical to SEQ ID NO:17; the antibody or BCMA-binding fragment thereof comprises a heavy chain variable domain amino acid sequence of SEQ ID NOS:29-31, 32-34 or 35-37, and is at least 80%, at least 85%, at least 90%, at least 95%, at least 96%, at least 97%, at least 98%, or at least 99% identical to SEQ ID NO:28; the antibody or BCMA-binding fragment thereof comprises a heavy chain variable domain amino acid sequence of SEQ ID NOS:40-42, 43-45, or 46-48, and is at least 80%, at least 85%, at least 90%, at least 95%, at least 96%, at least 97%, at least 98%, or at least 99% identical to SEQ ID NO:39; the antibody or BCMA-binding fragment thereof comprises a heavy chain variable domain amino acid sequence of SEQ ID NOS:51-53, 54-56, or 57-59, and is at least 80%, at least 85%, at least 90%, at least 95%, at least 96%, at least 97%, at least 98%, or at least 99% identical to SEQ ID NO:50.

In specific embodiments of any of the anti-BCMA antibodies or BCMA-binding fragments thereof, provided herein, the antibody is a monoclonal antibody, a chimeric antibody, a diabody, a Fab fragment, a Fab' fragment, or F(ab')2 fragment, an Fv, a bispecific antibody, a bispecific Fab2, a bispecific (mab)2, a humanized antibody, an artificially-generated human antibody, bispecific T-cell engager, bispecific NK cell engager, a single chain antibody (e.g., single-chain Fv fragment or scFv), triomab, knobs-into-holes (kih) IgG with common light chain, crossmab, ortho-Fab IgG, DVD-Ig, 2 in 1-IgG, IgG-scFv, sdFv2-Fc, bi-nanobody, tandAb, dual-affinity retargeting antibody (DART), DART-Fc, scFv-HSA-scFv (where HSA=human serum albumin), or dock-and-lock (DNL)-Fab3. In another specific embodiment of any of the anti-BCMA antibodies or BCMA-binding fragments thereof provided herein, said antibody or fragment is an antibody-drug conjugate.

In another aspect, provided herein is a polypeptide that comprises the heavy chain CDR1, CDR2 or CDR3 sequences of SEQ ID NO:7, SEQ ID NO:8, and SEQ ID NO:9, respectively; SEQ ID NO:10, SEQ ID NO:11 and SEQ ID NO:12, respectively; SEQ ID NO:13, SEQ ID NO:14 and SEQ ID NO:15, respectively; SEQ ID NO:18, SEQ ID NO:19 and SEQ ID NO:20, respectively; SEQ ID NO:21, SEQ ID NO:22 and SEQ ID NO:23, respectively; SEQ ID NO:24, SEQ ID NO:25 and SEQ ID NO:26, respectively; SEQ ID NO:29, SEQ ID NO:30 and SEQ ID NO:31, respectively; SEQ ID NO:32, SEQ ID NO:33 and SEQ ID NO:34, respectively; SEQ ID NO:35, SEQ ID NO:36 and SEQ ID NO:37, respectively; SEQ ID NO:40, SEQ ID NO:41 and SEQ ID NO:42, respectively; SEQ ID NO:43, SEQ ID NO:44 and SEQ ID NO:45, respectively; SEQ ID NO:46, SEQ ID NO:47 and SEQ ID NO:48, respectively; SEQ ID NO:51, SEQ ID NO:52 and SEQ ID NO:53, respectively; SEQ ID NO:54, SEQ ID NO:55 and SEQ ID NO:56, respectively; or SEQ ID NO:57, SEQ ID NO:58 and SEQ ID NO:59, respectively. In another embodiment, provided herein is a polypeptide that comprises the light chain CDR1, CDR2 and CDR3 sequences of SEQ ID NO:2, SEQ ID NO:3 and SEQ ID NO:4, respectively. In a specific embodiment of any of the polypeptides provided herein, the polypeptide additionally comprises light chain CDR1, CDR2 or CDR3 sequences of SEQ ID NO:2, SEQ ID NO:3 or SEQ ID NO:4, respectively. In a specific embodiment of any of the polypeptides provided herein, the polypeptide additionally comprises light chain CDR1, CDR2 or CDR3 sequences of SEQ ID NO:2, SEQ ID NO:3 and SEQ ID NO:4, respectively. Further provided herein is a polypeptide that comprises the light chain variable sequence of SEQ ID NO:1. Further provided herein is a polypeptide that comprises the heavy chain variable sequence of SEQ ID NO:6, SEQ ID NO:17, SEQ ID NO:28, SEQ ID NO:39, or SEQ ID NO:50.

In another aspect, provided herein is a composition comprising any of the antibodies, binding fragments thereof, or polypeptides provided herein. In a specific embodiment, the composition is a pharmaceutical composition. In other specific embodiments, the composition is formulated for intravenous, intraarterial, intramuscular, intradermal, subcutaneous, intradural, intrathecal, or intraperitoneal delivery.

In another aspect, provided herein are polynucleotides encoding any of the antibodies, antibody fragments, or polypeptides provided herein. In one embodiment, provided herein is a polynucleotide encoding an anti-BCMA antibody, BCMA-binding antibody fragment, or polypeptide comprising heavy chain CDR1, CDR2 or CDR3 sequences of SEQ ID NO:7, SEQ ID NO:8, and SEQ ID NO:9, respectively; SEQ ID NO:10, SEQ ID NO:11 and SEQ ID NO:12, respectively; SEQ ID NO:13, SEQ ID NO:14 and SEQ ID NO:15, respectively; SEQ ID NO:18, SEQ ID NO:19 and SEQ ID NO:20, respectively; SEQ ID NO:21, SEQ ID NO:22 and SEQ ID NO:23, respectively; SEQ ID NO:24, SEQ ID NO:25 and SEQ ID NO:26, respectively; SEQ ID NO:29, SEQ ID NO:30 and SEQ ID NO:31, respectively; SEQ ID NO:32, SEQ ID NO:33 and SEQ ID NO:34, respectively; SEQ ID NO:35, SEQ ID NO:36 and SEQ ID NO:37, respectively; SEQ ID NO:40, SEQ ID NO:41 and SEQ ID NO:42, respectively; SEQ ID NO:43, SEQ ID NO:44 and SEQ ID NO:45, respectively; SEQ ID NO:46, SEQ ID NO:47 and SEQ ID NO:48, respectively; SEQ ID NO:51, SEQ ID NO:52 and SEQ ID NO:53, respectively; SEQ ID NO:54, SEQ ID NO:55 and SEQ ID NO:56, respectively; or SEQ ID NO:57, SEQ ID NO:58 and SEQ ID NO:59, respectively. In a more specific embodiment of any of the polynucleotides provided herein, polynucleotide comprises the nucleotide sequence of SEQ ID NO:5, SEQ ID NO:16, SEQ ID NO:27, SEQ ID NO:38, SEQ ID NO:49 or SEQ ID NO:60. In another embodiment, provided herein is a polynucleotide encoding an anti-BCMA antibody, BCMA-binding antibody fragment, or polypeptide comprising light chain CDR1, CDR2 or CDR3 sequences of SEQ ID NO:2, SEQ ID NO:3 and SEQ ID NO:4, respectively. In another embodiment, provided herein is a polynucleotide that encodes a encoding an anti-BCMA antibody, BCMA-binding antibody fragment, or polypeptide that comprises the light chain variable sequence of SEQ ID NO:1. In another embodiment, provided herein is a polynucleotide that encodes an anti-BCMA antibody, BCMA-binding antibody fragment, or polypeptide that comprises the heavy chain variable sequence of SEQ ID NO:6, SEQ ID NO:17, SEQ ID NO:28, SEQ ID NO:39, or SEQ ID NO:50. In a specific embodiment, provided herein is a polynucleotide that encodes an anti-BCMA antibody, BCMA-binding antibody fragment, or polypeptide that comprises the light chain variable sequence of SEQ ID NO:1 and the heavy chain variable sequence of SEQ ID NO:6, SEQ ID NO:17, SEQ ID NO:28, SEQ ID NO:39, or SEQ ID NO:50.

In another aspect, provided herein are polynucleotide vectors comprising the polynucleotides provided herein. In a specific embodiment, the vector is an expression vector. In another specific embodiment, the vector is a retroviral vector or a lentiviral vector.

In another aspect, provided herein is a cell comprising any of the polynucleotides provided herein, or expressing any of the anti-BCMA antibodies, BCMA-binding fragments thereof, or polypeptides provided herein. In a specific embodiment, the cell comprises any of the vectors provided herein.

In another aspect, provided herein is a method of producing a polypeptide, comprising causing any of the cells provided herein to express a polynucleotide provided herein thereby producing said polypeptide; and isolating said polypeptide. Further provided herein is a method of producing an anti-BCMA antibody, or BCMA binding fragment thereof, comprising causing any of the cells provided herein to express a polynucleotide provided herein, thereby producing said antibody or fragment thereof; and isolating said antibody or fragment thereof.

In another aspect, provided herein is a method of depleting BCMA-expressing cells in a patient in need thereof, comprising administering to the patient a therapeutically effective amount of any of the anti-BCMA antibodies, BCMA binding fragment thereof, or polypeptides, provided herein. Further provided herein is a method of depleting BCMA-expressing cells in a patient in need thereof, comprising administering to the patient a therapeutically effective amount of any of the anti-BCMA antibodies, BCMA binding fragment thereof, or polypeptides, provided herein. Further provided herein is a method of treating a disorder caused by BCMA-expressing cells, e.g., BCMA-expressing plasma cells, in a patient in need thereof, comprising administering to the patient a therapeutically effective amount of the anti-BCMA antibodies, BCMA binding fragment thereof, or polypeptides provided herein. Further provided herein is a method of treating a B cell-related disorder, associated with BCMA expression, in a patient in need thereof, comprising administering to the patient a therapeutically effective amount of the any of the anti-BCMA antibodies, BCMA binding fragment thereof, or polypeptides, provided herein. In specific embodiments, the B cell-related disorder is multiple myeloma, plasmacytoma, Hodgkin lymphoma, a non-Hodgkins lymphoma, follicular lymphoma, small non-cleaved cell lymphoma, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, diffuse large B-cell lymphoma (DLBCL), indolent lymphoma, lymphoplasmacytic lymphoma, immunoblastic lymphoma, primary mediastinal B cell lymphoma, pulmonary B cell angiocentric lymphoma, small lymphocytic lymphoma, chronic lymphocytic leukemia, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas disease, Grave's disease, Wegener's granulomatosis, poly-arteritis nodosa, Sjogren syndrome, pemphigus vulgaris, scleroderma, multiple sclerosis, anti-phospholipid syndrome, ANCA associated vasculitis, Goodpasture's disease, Kawasaki disease, autoimmune hemolytic anemia, systemic lupus erythematosus, rapidly progressive glomerulonephritis, heavy-chain disease, primary or immunocyte-associated amyloidosis, cutaneous lupus erythematosus, monoclonal gammopathy of undetermined significance, or glioblastoma.

In a further aspect, provided herein are chimeric antigen receptors (CARs) that comprise any of the heavy or light chain CDR sequences provided herein, or any of the heavy or light chain variable sequences provided herein. In one embodiment, the CAR comprises said heavy chain CDR1, CDR2 and CDR3 sequences, and/or said light chain CDR1, CDR2 and CDR3 sequences in an extracellular BCMA-binding domain. In another embodiment, the CAR comprises said light chain sequence and/or said heavy chain sequence in an extracellular BCMA-binding domain. In another embodiment, the CAR comprises, or additionally comprises, one or more of a transmembrane domain, a primary signaling domain, and/or a costimulatory domain. Further provided herein are cells, e.g., immune cells, that express any of the CARs provided herein. In more specific embodiments, the cells are T cells, natural killer cells (NK cells), or natural killer T cells (NKT cells). Further provided herein is a method of depleting BCMA-expressing cells, e.g., plasma cells, in a patient in need thereof, comprising administering to the patient a therapeutically effective amount of cells expressing an anti-BCMA CAR provided herein. A method of treating a B cell-related disorder associated with BCMA expression in a patient in need thereof, comprising administering to the patient a therapeutically effective amount of the cell of any of the embodiments provided herein. In a specific embodiment of any of the methods involving a cell expressing an anti-BCMA CAR provided herein, the B cell-related disorder is multiple myeloma, plasmacytoma, Hodgkin lymphoma, a non-Hodgkins lymphoma, follicular lymphoma, small non-cleaved cell lymphoma, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, diffuse large B-cell lymphoma (DLBCL), indolent lymphoma, lymphoplasmacytic lymphoma, immunoblastic lymphoma, primary mediastinal B cell lymphoma, pulmonary B cell angiocentric lymphoma, small lymphocytic lymphoma, chronic lymphocytic leukemia, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas disease, Grave's disease, Wegener's granulomatosis, poly-arteritis *nodosa*, Sjogren syndrome, pemphigus vulgaris, scleroderma, multiple sclerosis, anti-phospholipid syndrome, ANCA associated vasculitis, Goodpasture's disease, Kawasaki disease, autoimmune hemolytic anemia, systemic lupus erythematosus, rapidly progressive glomerulonephritis, heavy-chain disease, primary or immunocyte-associated amyloidosis, cutaneous lupus erythematosus, monoclonal gammopathy of undetermined significance, or glioblastoma.

5. FIGURES

FIGS. 2A-2F represent histograms showing that the human IgG antibodies, 320262, 319966, 320111, 319883 and 320199, bind C6 cells expressing human BCMA.

FIGS. 3A-3F show histograms demonstrating that the human IgG antibodies, 320262, 319966, 320111, 319883 and 320199, did not bind Hek293 cells expressing the TNF receptor family member, TNFRSF12A.

FIGS. 4A-4F present histograms documenting that the human IgG antibodies, 320262, 319966, 320111, 319883 and 320199 bind NCIH929 human multiple myeloma cells that endogenously express BCMA.

Figure 5B:
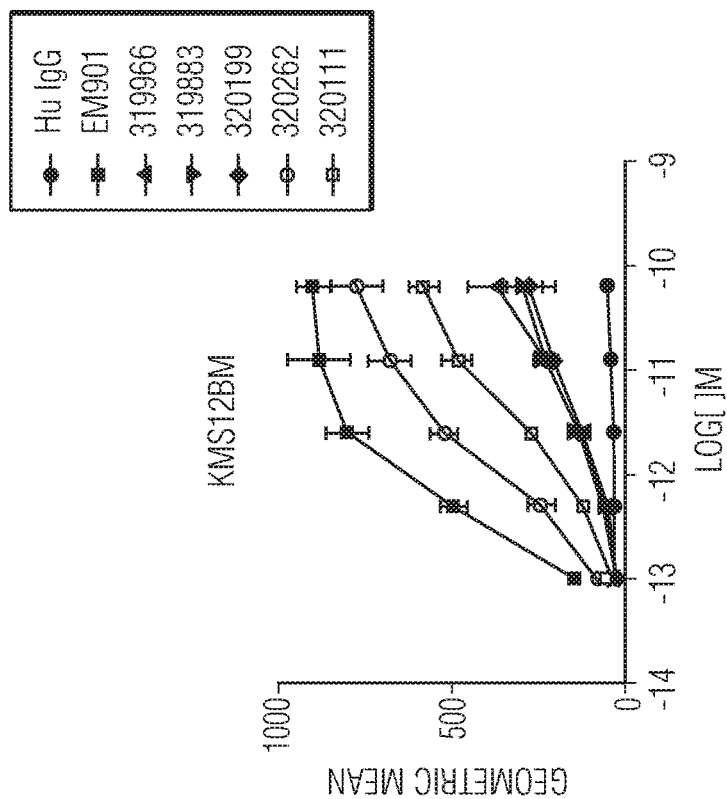
Figure 5A:
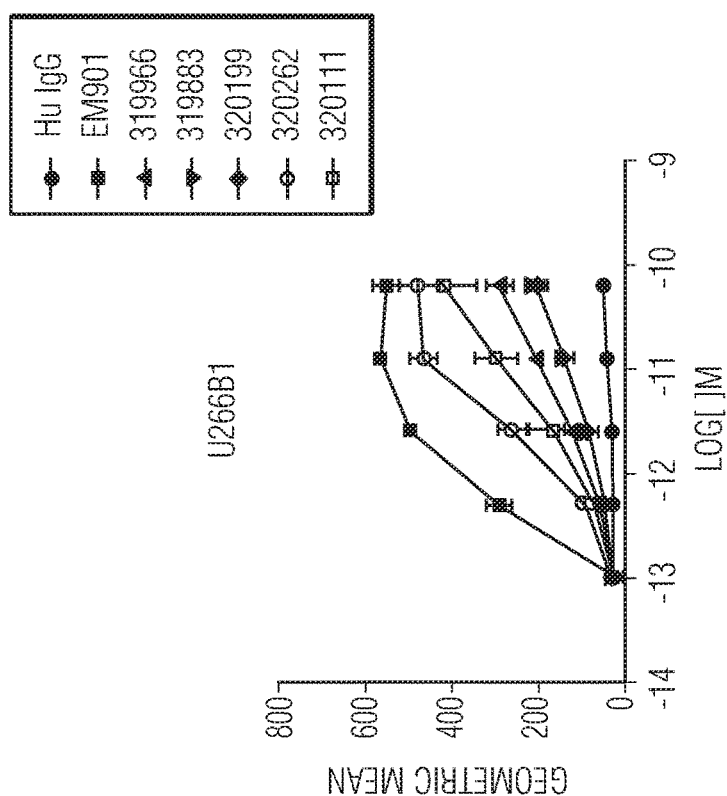
Figures 5C, 5D:
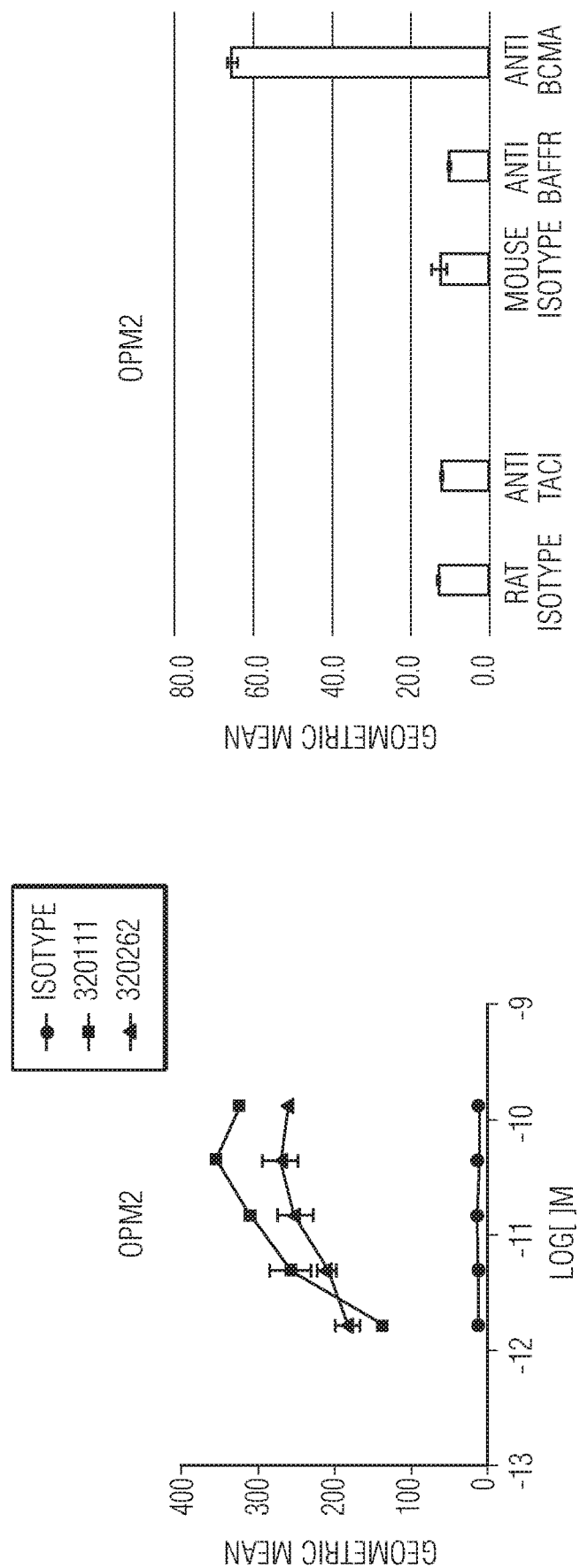

FIGS. 5A-5B present dose-response curves for binding of human IgG antibodies, 320262, 319966, 320111, 319883 and 320199, to BCMA-positive U266B1 (FIG. 5A) and KMS12BM (FIG. 5B) human multiple myeloma cells. FIG. 5D and FIG. 5F also present bar graphs depicting the expression profiles of TNF receptor family members, BCMA, TACI and BAFF in OPM2 (FIG. 5D) and NUDHL1 (FIG. 5F) cells utilizing commercially-available antibodies. Finally, FIGS. 5C and 5E illustrate dose-response curves for 320111 and 320262 binding to BCMA$^+$/TACI$^-$/BAFFR$^-$ OPM2 (FIG. 5C), but not BCMA$^-$/TACI$^+$/BAFFR$^+$ NUDHL1 (FIG. 5E) cells.

6. DETAILED DESCRIPTION

Provided herein are polypeptides, e.g., BCMA-binding polypeptides, that comprise specific CDR1, CDR2 and CDR3 sequences, and BCMA-binding antibodies, antibody fragments, and polypeptides that comprise such CDR1, CDR2 and CDR3 sequences. Also provided herein are methods of using such antibodies, antibody fragments, and polypeptides for therapeutic uses, e.g., for the treatment of subjects having a plasma cell- or B cell-related disease or disorder.

As used herein, "CDR" means Complementarity Determining Region, the specific sequences of an antibody heavy chain or light chain that mediate binding between an antibody and the antigen or epitope to which the antibody is directed; amino acid residues of an antibody which are (usually three or four short regions of extreme sequence variability) within the V-region domain of an immunoglobulin which form the antigen-binding site and are the main determinants of antigen specificity. The sequence of a CDR may be determined or numbered by, for example, the Kabat system (see Kabat, et al., 1983. Sequence of Proteins of Immunological Interest. National Institutes of Health, Bethesda, Md.); the Chothia system (see Chothia &, Lesk, "Canonical Structures for the Hypervariable Regions of Immunoglobulins," *J. Mol. Biol.* 196, 901-917 (1987)); or the IMGT system (see Lefranc et al., "IMGT Unique Numbering for Immunoglobulin and Cell Receptor Variable Domains and Ig superfamily V-like domains," *Dev. Comp. Immunol.* 27, 55-77 (2003)). See also Abhinandan & Martin, "Analysis and Improvements to Kabat and Structurally Correct Numbering of Antibody Variable Domains," *Mol. Immunol.* 45:3832 (2008).

6.1. Polypeptides

Provided herein is a polypeptide that comprises specific heavy chain CDR1, CDR2 and CDR3 sequences. In specific embodiments, such polypeptides are capable of binding BCMA, either alone or in combination with a polypeptide comprising specific light chain CDR1, CDR2 and CDR3 sequences.

In a first embodiment, provided herein is a polypeptide that comprises the CDR1, CDR2 and/or CDR3 sequences of SEQ ID NOS:7, 8 and 9, respectively. Further provided herein is a polypeptide that comprises the CDR1, CDR2 and/or CDR3 sequences of SEQ ID NOS:10, 11 and 12, respectively. Further provided herein is a polypeptide that comprises the CDR1, CDR2 and/or CDR3 sequences of SEQ ID NOS:13, 14 and 15, respectively. In a specific embodiment of any of these embodiments, the polypeptide comprises the heavy chain variable region sequence of SEQ ID NO:2. In a specific embodiment of any of these embodiments, the polypeptide is an Fab fragment that comprises the heavy chain variable region sequence of SEQ ID NO:6. In another specific embodiment of any of these embodiments, the polypeptide is an F(ab')2 fragment that comprises the heavy chain variable region sequence of SEQ ID NO:6.

In another embodiment, provided herein is a polypeptide that comprises the CDR1, CDR2 and/or CDR3 sequences of SEQ ID NOS:18, 19 and 20, respectively. Further provided herein is a polypeptide that comprises the CDR1, CDR2 and/or CDR3 sequences of SEQ ID NOS:21, 22 and 23, respectively. Further provided herein is a polypeptide that comprises the CDR1, CDR2 and/or CDR3 sequences of SEQ ID NOS:24, 25 and 26, respectively. In a specific embodiment of any of these embodiments, the polypeptide comprises the heavy chain variable region sequence of SEQ ID NO:17. In a specific embodiment of any of these embodiments, the polypeptide is an Fab fragment that comprises the heavy chain variable region sequence of SEQ ID NO:17. In another specific embodiment of any of these embodiments, the polypeptide is an F(ab')2 fragment that comprises the heavy chain variable region sequence of SEQ ID NO:17.

In another embodiment, provided herein is a polypeptide that comprises the CDR1, CDR2 and/or CDR3 sequences of SEQ ID NOS:29, 30 and 31, respectively. Further provided herein is a polypeptide that comprises the CDR1, CDR2 and/or CDR3 sequences of SEQ ID NOS:32, 33 and 34, respectively. Further provided herein is a polypeptide that comprises the CDR1, CDR2 and/or CDR3 sequences of SEQ ID NOS:35, 36 and 37, respectively. In a specific embodiment of any of these embodiments, the polypeptide comprises the heavy chain variable region sequence of SEQ ID NO:28. In a specific embodiment of any of these embodiments, the polypeptide is an Fab fragment that comprises the heavy chain variable region sequence of SEQ ID NO:28. In another specific embodiment of any of these embodiments, the polypeptide is an F(ab')2 fragment that comprises the heavy chain variable region sequence of SEQ ID NO:28.

In another embodiment, provided herein is a polypeptide that comprises the CDR1, CDR2 and/or CDR3 sequences of SEQ ID NOS:40, 41 and 42, respectively. Further provided herein is a polypeptide that comprises the CDR1, CDR2 and/or CDR3 sequences of SEQ ID NOS:43, 44 and 45, respectively. Further provided herein is a polypeptide that comprises the CDR1, CDR2 and/or CDR3 sequences of SEQ ID NOS:46, 47 and 48, respectively. In a specific embodiment of any of these embodiments, the polypeptide comprises the heavy chain variable region sequence of SEQ ID NO:39. In a specific embodiment of any of these embodiments, the polypeptide is an Fab fragment that comprises the heavy chain variable region sequence of SEQ ID NO:39. In another specific embodiment of any of these embodiments, the polypeptide is an F(ab')2 fragment that comprises the heavy chain variable region sequence of SEQ ID NO:39.

In another embodiment, provided herein is a polypeptide that comprises the CDR1, CDR2 and/or CDR3 sequences of SEQ ID NOS:51, 52 and 53, respectively. Further provided herein is a polypeptide that comprises the CDR1, CDR2 and/or CDR3 sequences of SEQ ID NOS:54, 55 and 56, respectively. Further provided herein is a polypeptide that comprises the CDR1, CDR2 and/or CDR3 sequences of SEQ ID NOS:57, 58 and 59, respectively. In a specific embodiment of any of these embodiments, the polypeptide comprises the heavy chain variable region sequence of SEQ ID NO:50. In a specific embodiment of any of these embodiments, the polypeptide is an Fab fragment that comprises the heavy chain variable region sequence of SEQ ID NO:50. In another specific embodiment of any of these embodiments, the polypeptide is an F(ab')2 fragment that comprises the heavy chain variable region sequence of SEQ ID NO:50.

Also provided herein is an antibody that comprises specific light chain CDR1, CDR2 and CDR3 sequences. In specific embodiments, such antibodies are capable of binding BCMA, either alone or in combination with heavy chain CDR1, CDR2 and CDR3 sequences. In a first embodiment, provided herein is an antibody that comprises the CDR1, CDR2 and/or CDR3 sequences of SEQ ID NOS:2, 3 and 4, respectively. In a specific embodiment of any of these embodiments, the antibodies comprises the light chain variable region sequence of SEQ ID NO:1. In a specific embodiment of any of these embodiments, the antibodies is an Fab fragment that comprises the light chain variable region sequence of SEQ ID NO:1. In another specific embodiment, the antibody is an F(ab')2 fragment that comprises the light chain variable region sequence of SEQ ID NO:1

Provided herein is an antibody that comprises specific heavy chain CDR1, CDR2 and CDR3 sequences. In specific embodiments, such polypeptides are capable of binding BCMA, either alone or in combination with a polypeptide comprising specific light chain CDR1, CDR2 and CDR3 sequences.

In a first embodiment, provided herein is an antibody that comprises the CDR1, CDR2 and/or CDR3 sequences of SEQ ID NOS:7, 8 and 9, respectively. Further provided herein is an antibody that comprises the CDR1, CDR2 and/or CDR3 sequences of SEQ ID NOS:10, 11 and 12, respectively. Further provided herein is an antibody that comprises the CDR1, CDR2 and/or CDR3 sequences of SEQ ID NOS:13, 14 and 15, respectively. In a specific embodiment of any of these embodiments, the antibody comprises the heavy chain variable region sequence of SEQ ID NO:2. In a specific embodiment of any of these embodiments, the antibody is an Fab fragment that comprises the heavy chain variable region sequence of SEQ ID NO:6. In another specific embodiment, the antibody is an F(ab')2 fragment that comprises the heavy chain variable region sequence of SEQ ID NO:6.

In another embodiment, provided herein is an antibody that comprises the CDR1, CDR2 and/or CDR3 sequences of SEQ ID NOS:18, 19 and 20, respectively. Further provided herein is an antibody that comprises the CDR1, CDR2 and/or CDR3 sequences of SEQ ID NOS:21, 22 and 23, respectively. Further provided herein is an antibody that comprises the CDR1, CDR2 and/or CDR3 sequences of SEQ ID NOS:24, 25 and 26, respectively. In a specific embodiment of any of these embodiments, the antibody comprises the heavy chain variable region sequence of SEQ ID NO:17. In a specific embodiment of any of these embodiments, the antibody is an Fab fragment that comprises the heavy chain variable region sequence of SEQ ID NO:17. In another specific embodiment of any of these embodiments, the antibody is an F(ab')2 fragment that comprises the heavy chain variable region sequence of SEQ ID NO:17.

In another embodiment, provided herein is an antibody that comprises the CDR1, CDR2 and/or CDR3 sequences of SEQ ID NOS:29, 30 and 31, respectively. Further provided herein is an antibody that comprises the CDR1, CDR2 and/or CDR3 sequences of SEQ ID NOS:32, 33 and 34, respectively. Further provided herein is an antibody that comprises the CDR1, CDR2 and/or CDR3 sequences of SEQ ID NOS:35, 36 and 37, respectively. In a specific embodiment of any of these embodiments, the antibody comprises the heavy chain variable region sequence of SEQ ID NO:28. In a specific embodiment of any of these embodiments, the antibody is an Fab fragment that comprises the heavy chain variable region sequence of SEQ ID NO:28. In another specific embodiment of any of these embodiments, the antibody is an F(ab')2 fragment that comprises the heavy chain variable region sequence of SEQ ID NO:28.

In another embodiment, provided herein is an antibody that comprises the CDR1, CDR2 and/or CDR3 sequences of SEQ ID NOS:40, 41 and 42, respectively. Further provided herein is an antibody that comprises the CDR1, CDR2 and/or CDR3 sequences of SEQ ID NOS:43, 44 and 45, respectively. Further provided herein is an antibody that comprises the CDR1, CDR2 and/or CDR3 sequences of SEQ ID NOS:46, 47 and 48, respectively. In a specific embodiment of any of these embodiments, the antibody comprises the heavy chain variable region sequence of SEQ ID NO:39. In a specific embodiment of any of these embodiments, the antibody is an Fab fragment that comprises the heavy chain variable region sequence of SEQ ID NO:39. In another specific embodiment of any of these embodiments, the antibody is an F(ab')2 fragment that comprises the heavy chain variable region sequence of SEQ ID NO:39.

In another embodiment, provided herein is an antibody that comprises the CDR1, CDR2 and/or CDR3 sequences of SEQ ID NOS:51, 52 and 53, respectively. Further provided herein is an antibody that comprises the CDR1, CDR2 and/or CDR3 sequences of SEQ ID NOS:54, 55 and 56, respectively. Further provided herein is an antibody that comprises the CDR1, CDR2 and/or CDR3 sequences of SEQ ID NOS:57, 58 and 59, respectively. In a specific embodiment of any of these embodiments, the antibody comprises the heavy chain variable region sequence of SEQ ID NO:50. In a specific embodiment of any of these embodiments, the antibody is an Fab fragment that comprises the heavy chain variable region sequence of SEQ ID NO:50. In another specific embodiment of any of these embodiments, the antibody is an F(ab')2 fragment that comprises the heavy chain variable region sequence of SEQ ID NO:50.

Also provided herein is a polypeptide that comprises specific light chain CDR1, CDR2 and CDR3 sequences. In specific embodiments, such polypeptides are capable of binding BCMA, either alone or in combination with a polypeptide comprising specific CDR1, CDR2 and CDR3 sequences. In a first embodiment, provided herein is a polypeptide that comprises the CDR1, CDR2 and/or CDR3 sequences of SEQ ID NOS:2, 3 and 4, respectively. In a specific embodiment of any of these embodiments, the polypeptide comprises the light chain variable region sequence of SEQ ID NO:1. In a specific embodiment of any of these embodiments, the polypeptide is an Fab fragment that comprises the light chain variable region sequence of SEQ ID NO:1. In another specific embodiment of any of these embodiments, the polypeptide is an F(ab')2 fragment that comprises the light chain variable region sequence of SEQ ID NO:1.

Also provided herein is an antibody that comprises specific light chain CDR1, CDR2 and CDR3 sequences. In a first embodiment, provided herein is an antibody that comprises the CDR1, CDR2 and/or CDR3 sequences of SEQ ID NOS:2, 3 and 4, respectively. In a specific embodiment of any of these embodiments, the antibody comprises the light chain variable region sequence of SEQ ID NO:1. In a specific embodiment of any of these embodiments, the antibody is an Fab fragment that comprises the light chain variable region sequence of SEQ ID NO:1. In another specific embodiment of any of these embodiments, the antibody is an F(ab')2 fragment that comprises the light chain variable region sequence of SEQ ID NO:1.

In more specific embodiments of any of the above antibodies or BCMA-binding fragments thereof, the antibody or BCMA-binding fragment thereof comprises a light chain variable domain amino acid sequence at least 80%, at least 85%, at least 90%, at least 95%, at least 96%, at least 97%, at least 98%, at least 99%, or 100% identical to SEQ ID NO:1 and a heavy chain variable domain amino acid sequence at least 80%, at least 85%, at least 90%, at least 95%, at least 96%, at least 97%, at least 98%, at least 99%, or 100% identical to SEQ ID NO:6, SEQ ID NO:17, SEQ ID NO:28, SEQ ID NO:39, or SEQ ID NO:50.

In a more specific embodiment of any of the above antibodies or BCMA-binding fragments thereof, the antibody or BCMA-binding fragment thereof comprises the light chain variable domain amino acid sequence of SEQ ID NO:1, or a light chain variable domain amino acid sequence at least 80%, at least 85%, at least 90%, at least 95%, at least 96%, at least 97%, at least 98%, or at least 99% identical to SEQ ID NO:1. In other more specific embodiments of any of the above antibodies or BCMA-binding fragments thereof, the antibody or BCMA-binding fragment thereof comprises the heavy chain variable domain amino acid sequence of SEQ ID NO:6, SEQ ID NO:17, SEQ ID NO:28, SEQ ID NO:39, or SEQ ID NO:50, or a heavy chain variable domain amino acid sequence at least 80%, at least 85%, at least 90%, at least 95%, at least 96%, at least 97%, at least 98%, or at least 99% identical to SEQ ID NO:6, SEQ ID NO:18, SEQ ID NO:28, SEQ ID NO:39, or SEQ ID NO:50. In another more specific embodiment of any of the above antibodies or BCMA-binding fragments thereof, the antibody or BCMA-binding fragment thereof comprises a light chain variable domain amino acid sequence at least 80%, at least 85%, at least 90%, at least 95%, at least 96%, at least 97%, at least 98%, at least 99%, or 100% identical to SEQ ID NO:1 and a heavy chain variable domain amino acid sequence at least 80%, at least 85%, at least 90%, at least 95%, at least 96%, at least 97%, at least 98%, at least 99%, or 100% identical to SEQ ID NO:6, SEQ ID NO:17, SEQ ID NO:28, SEQ ID NO:39, or SEQ ID NO:50.

In a more specific embodiment of any of the above antibodies or BCMA-binding fragments thereof, the antibody or BCMA-binding fragment thereof comprises a light chain variable domain amino acid sequence that comprises the amino acid sequence of SEQ ID NO:2, SEQ ID NO:3 and SEQ ID NO:4, and is at least 80%, at least 85%, at least 90%, at least 95%, at least 96%, at least 97%, at least 98%, or at least 99% identical to SEQ ID NO:1. In other more specific embodiments of any of the above antibodies or BCMA-binding fragments thereof, the antibody or BCMA-binding fragment thereof comprises a heavy chain variable domain amino acid sequence of SEQ ID NOS:7-9, 10-12 or 13-15, and is at least 80%, at least 85%, at least 90%, at least 95%, at least 96%, at least 97%, at least 98%, or at least 99% identical to SEQ ID NO:6; the antibody or BCMA-binding fragment thereof comprises a heavy chain variable domain amino acid sequence of SEQ ID NOS:18-20, 21-23, or 24-26, and is at least 80%, at least 85%, at least 90%, at least 95%, at least 96%, at least 97%, at least 98%, or at least 99% identical to SEQ ID NO:17; the antibody or BCMA-binding fragment thereof comprises a heavy chain variable domain amino acid sequence of SEQ ID NOS:29-31, 32-34 or 35-37, and is at least 80%, at least 85%, at least 90%, at least 95%, at least 96%, at least 97%, at least 98%, or at least 99% identical to SEQ ID NO:28; the antibody or BCMA-binding fragment thereof comprises a heavy chain variable domain amino acid sequence of SEQ ID NOS:40-42, 43-45, or 46-48, and is at least 80%, at least 85%, at least 90%, at least 95%, at least 96%, at least 97%, at least 98%, or at least 99% identical to SEQ ID NO:39; the antibody or BCMA-binding fragment thereof comprises a heavy chain variable domain amino acid sequence of SEQ ID NOS:51-53, 54-56, or 57-59, and is at least 80%, at least 85%, at least 90%, at least 95%, at least 96%, at least 97%, at least 98%, or at least 99% identical to SEQ ID NO:50.

6.2. Antibodies

Further provided herein are antibodies that are, or comprise, the CDR sequences or the heavy or light chain variable sequences provided herein.

The term "antibody" as used herein means any naturally-occurring or artificially-constructed configuration of an antigen-binding polypeptide comprising one, two or three light chain CDRs, and one, two or three heavy chain CDRs, wherein the polypeptide is capable of binding to the antigen.

In certain embodiments, the antibody according to the invention is an antibody with an Fc part or without an Fc part. In certain embodiments, the antibodies provided herein are IgG antibodies, e.g., IgG1, IgG2, IgG3 or IgG4 antibodies. In certain embodiments, the antibodies are IgA antibodies, IgE antibodies, IgD antibodies, or IgM antibodies. In certain embodiments, the antibodies are monoclonal antibodies, e.g., monoclonal IgG antibodies.

In some embodiments, any of the antibodies provided herein comprises an Fc variant of a wild-type human IgG Fc region, wherein said antibody exhibits a reduced affinity to the human FcγRIIIA and/or FcγRIIA and/or FcγRI compared to an antibody comprising the wild-type IgG Fc region.

In certain embodiments, said antibodies are artificially-produced fully-human antibodies, e.g., antibodies produced by a mouse or rat genetically modified to produce human antibodies, e.g., the OMNIRAT or OMNIMOUSE (Ligand Pharmaceuticals). Such antibodies are not naturally-occurring but have human framework and constant regions. Because human BCMA is a self-antigen, the human body will not produce antibodies to human BCMA. Human anti-BCMA antibodies may be those having variable and constant regions corresponding substantially to human germline immunoglobulin sequences known in the art, including, for example, those described by Kabat et al. The human antibodies of the invention may include amino acid residues not encoded by human germline immunoglobulin sequences (e.g., mutations introduced by random or site-specific mutagenesis in vitro or by somatic mutation in vivo), for example in the CDRs, and in particular CDR3. The human anti-BCMA antibodies provided herein can have at least one, two, three, four, five, or more positions replaced with an amino acid residue that is not encoded by the human germline immunoglobulin sequence.

In certain embodiments, the antibodies provided herein are monoclonal antibodies. The term "monoclonal antibody" as used herein refers to an antibody obtained from a population of substantially homogeneous antibodies, that is, the individual antibodies comprising the population are identical except for possible mutations and/or post-translation modifications (e.g., isomerizations, amidations) that may be present in minor amounts. The term may be used to refer to such a homogeneous population of antibodies. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on an antigen. In addition to their specificity, the monoclonal antibodies are advantageous in that they may be synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, monoclonal anti-BCMA antibodies as provided herein may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991), for example.

In certain embodiments, the antibodies provided herein, e.g., monoclonal antibodies are "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies. Preferably, such chimeric antibodies exhibit the desired biological activity, e.g., binding to BCMA (U.S. Pat. No. 4,816,567; Morrison et al., Proc. Natl. Acad. Sci. USA, 81:6851-6855 (1984)). In certain embodiments, chimeric antibodies provided herein include "primitized" antibodies comprising variable domain antigen-binding sequences derived from a non-human primate (e.g., cynomolgus monkey, ape, etc.) and human constant region sequences.

In certain embodiments, the BCMA-binding antibodies herein are monovalent. In other embodiments, the BCMA-binding antibodies provided herein are multivalent, e.g. bivalent, trivalent, or tetravalent. In certain embodiments, the BCMA-binding antibodies provided herein are monospecific. In other embodiments, the BCMA-binding antibodies provided herein are multispecific, e.g. bispecific, trispecific, etc. In certain embodiments, the BCMA-binding antibodies provided herein, which are multivalent, bind two or more epitopes of BCMA.

In certain other embodiments, antibodies, e.g., monoclonal antibodies, provided herein can be humanized antibodies that may be produced using recombinant DNA techniques known in the art. A variety of approaches for making chimeric antibodies have been described. See e.g., Morrison et al., Proc. Natl. Acad. Sci. USA, 81:6851 (1985); Takeda et al., Nature 314:452 (1985), Cabilly et al., U.S. Pat. No. 4,816,567; Boss et al., U.S. Pat. No. 4,816,397; Tanaguchi et al., EP 0171496; EP 0173494, GB 2177096.

In other embodiments, the antibody provided herein is a bispecific antibody; that is, it targets a second antigen in addition to BCMA. A "bispecific" or "bifunctional" antibody or immunoglobulin is an artificial hybrid antibody or immunoglobulin having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990). Numerous methods known to those skilled in the art are available for obtaining antibodies or antigen-binding fragments thereof. For example, antibodies can be produced using recombinant DNA methods (see, e.g., U.S. Pat. No. 4,816,567). A wide variety of recombinant bispecific antibody formats have been developed in the recent past (see e.g. Kontermann RE, mAbs 4:2, (2012) 1-16). In specific embodiments, the antibody is a diabody, a bispecific antibody, a bispecific antibody with knobs-into-holes technology, a bispecific antibody with CrossMAB technology e.g. wherein the VL and VH or CH1 and CL of one or more of the Fab fragments is exchanged, a bispecific Fab2, and/or a bispecific (mab)2, or the like. In a specific embodiment, the anti-BCMA Fab comprises the CrossMAB technology. In another specific embodiment, said second antigen is CD19.

In other specific embodiments, the antibody is bispecific T-cell engager. In a more specific embodiment, the second antigen targeted by the T cell engager is CD3. In other specific embodiments, the antibody is an bispecific NK cell engager. In a more specific embodiment, the second antigen targeted by the NK cell engager is NKG2D.

In certain embodiments, the bispecific antibody comprises not more than two Fab fragments of an anti-BCMA antibody and not more than one Fab fragment of a second antibody, e.g. not more than one Fab fragment of an anti-CD3 antibody, ("2+1"), optionally with not more than one Fc part.

In other embodiments, provided herein are BCMA-binding antibody fragments, e.g., a single chain antibodies, Fab fragments or F'(ab)2 fragments.

Further provided herein are BCMA-binding antibodies in other configurations, e.g., said antibody is or comprises a triomab, kih IgG with common light chain, CrossMAb, e.g. wherein the VL and VH or CH1 and CL of one or more of the Fab fragments is exchanged, ortho-Fab IgG, DVD-Ig, 2 in 1-IgG, IgG-scFv, sdFv2-Fc, bi-nanobody, tandAb, dual-affinity retargeting antibody (DART) (e.g., by Creative Biolabs), DART-Fc, scFv-HSA-scFv (where HSA=human serum albumin), dock-and-lock (DNL)-Fab3, ImmTAC, DAF, HSA body, IgG-fynomer, and ART-Ig.

6.3. Antibody-Drug Conjugates

In another aspect, in certain embodiments, each or any of the antibodies or BCMA-binding fragments thereof may be conjugated to a drug, e.g. a toxin or toxic moiety, protein, polysaccharide or small molecule, to form an antibody-drug conjugate. In one embodiment of the invention, the drug is, e.g., one or more of an anti-apoptotic agent, a mitotic inhibitor, an anti-tumor antibiotic, an immunomodulating agent, a nucleic acid for gene therapy, an alkylating agent, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In certain embodiments, the mitotic inhibitor is a dolastatin, an auristatin, a maytansinoid, and a plant alkaloid. In certain embodiments, the drug is a dolastatin, an auristatin, a maytansinoid, and a plant alkaloid. An example of an auristatin is monomethylaurisatin F (MMAF) or monomethyauristatin E (MMAE). Examples of maytansinoids include, but are not limited to, DM1, DM2, DM3, and DM4. In certain embodiments, the anti-tumor antibiotic is selected from the group consisting of an actinomycine, an anthracycline, a calicheamicin, and a duocarmycin. In certain embodiments, the actinomycine is a pyrrolobenzodiazepine (PBD).

In certain embodiments in which the drug is a maytansinoid, the maytansinoid is a thiol-containing maytansinoid, produced, for example, according to the processes disclosed in U.S. Pat. No. 6,333,410. In a specific embodiment, the maytansinoid is DM-1 (N2-deacetyl-N2-(3-mercapto-1-oxopropyl)-maytansine). DM-1 is 3- to 10-fold more cytotoxic than maytansine, and may be converted into a pro-drug by linking it via disulfide bond(s) to an anti-BCMA antibody or BCMA-binding fragment thereof as provided herein. Certain of these conjugates (sometimes called "tumor activated prodrugs" (TAPs)) are not cytotoxic in the bloodstream, as they are activated upon associating with target cells and internalized, thereby releasing the drug. In other specific embodiments, the maytansinoids comprise a side chain that contains a sterically hindered thiol bond such as, but not limited to, maytansinoids N2-deacetyl-N2-(4-mercapto-1-oxopentyl)-maytansine, also referred to as "DM3," and N2-deacetyl-N2-(4-methyl-4-mercapto-1-oxopentyl)-maytansine, also referred to as "DM4." DM4 differs from DM1 and DM3 in that it bears methyl groups at its αC. This results in a steric hindrance when DM4 is attached via a linker in particular, but not limited to, a linker comprising a disulfide bond, to a targeting agent such as nBT062. A wide variety of maytansinoids bearing a sterically hindered thiol group (possessing one or two substituents, in particular alkyls substituents, such as the methyl substituents of DM4) are disclosed U.S. Pat. App. Pubn. 2004/0235840, which is incorporated herein in its entirety by reference. Other effector molecules comprising substitutents such as alkyl groups at positions that result in a steric hindrance when the effector is attached to a targeting agent via a linker may be used. In certain specific embodiments this hindrance induces a chemical modification such as alkylation of the free drug to increase its overall stability, which allows the drug to not only induce cell death or continuous cell cycle arrest in BCMA-expressing tumor cells but, optionally, also to affect auxiliary cells that, e.g., support or protect the tumor from drugs, in particular cells of the tumor stroma and the tumor vasculature and which generally do not express BCMA to diminish or lose their supporting or protecting function. DNA alkylating agents may also be used as effector molecules and include, but are not limited to, CC-1065 analogues or derivatives. CC-1065 is a potent antitumor-antibiotic isolated from cultures of Streptomyces zelensis and has been shown to be exceptionally cytotoxic in vitro (U.S. Pat. No. 4,169,888).

In certain other specific embodiments, the drug is a taxane, e.g., a taxane that comprises one or more thiol or disulfide groups. Taxanes inhibit the depolymerization of tubulin, resulting in an increase in the rate of microtubule assembly and cell death. Taxanes that may be used in antibody-drug conjugates with the anti-BCMA antibodies or BCMA binding fragments thereof presented herein, for example, disclosed in U.S. Pat. Nos. 6,436,931; 6,340,701; 6,706,708 and United States Patent Publications 2004/0087649; 2004/0024049 and 2003/0004210. Other taxanes that may be used are disclosed, for example, in U.S. Pat. Nos. 6,002,023, 5,998,656, 5,892,063, 5,763,477, 5,705, 508, 5,703,247, 5,367,086, and 6,596,757.

In certain embodiments, the drug is pomalidomide (4-amino-2-[(3RS)-(2,6-dioxopiperidin-3-yl)-1H-isoindole-1,3(2H)-dione). In another specific embodiment, the drug is thalidomide ((RS)-2-(2,6-dioxopiperidin-3-yl)-1H-isoindole-1,3(2H)-dione). In another specific embodiment, the drug is lenalidomide (3-(4-amino-1-oxo-1,3-dihydro-2H-isoindol-2-yl)piperidine-2,6-dione). In another specific embodiment, the drug is 3-[4-(4-morpholin-4-ylmethyl-benzyloxy)-1-oxo-1,3-dihydro-Isoindol-2-yl]-piperidine-2,6-dione. In another specific embodiment, the cereblon-binding compound used in accordance with the methods described herein is 3-(4-((4-((4-(2,4-difluorophenyl)piperazin-1-yl)methyl)benzyl)oxy)-1-oxoisoindolin-2-yl)piperidine-2,6-dione. See, e.g., U.S. Patent Application Publication No. 2014/0162282 for disclosure related to these compounds, which is incorporated by reference herein in its entirety.

Compounds for the methods provided herein include, but are not limited to, the immunomodulatory compounds (Celgene Corporation), a group of compounds that can be useful to treat several types of human diseases, including certain cancers.

As used herein and unless otherwise indicated, the term "immunomodulatory compound" can encompass certain small organic molecules that inhibit LPS induced monocyte TNF-.alpha., IL-1B, 1L-12, IL-6, MIP-1.alpha., MCP-1, GM-CSF, G-CSF, and COX-2 production. These compounds can be prepared synthetically, or can be obtained commercially.

In certain embodiments, the drug includes the tetra substituted 2-(2,6-dioxopiperidin-3-yl)-1-oxoisoindolines described in U.S. Pat. No. 5,798,368; 1-oxo and 1,3-dioxo-2-(2,6-dioxopiperidin-3-yl)isoindolines (e.g., 4-methyl derivatives of thalidomide), substituted 2-(2,6-dioxopiperidin-3-yl)phthalimides and substituted 2-(2,6-dioxopiperidin-3-yl)-1-oxoisoindoles including, but not limited to, those disclosed in U.S. Pat. Nos. 5,635,517, 6,281,230, 6,316,471, 6,403,613, 6,476,052 and 6,555,554; Publication No. WO 02/059106). The entireties of each of the patents and patent applications identified herein are incorporated by reference.

Various compounds disclosed herein contain one or more chiral centers, and can exist as racemic mixtures of enantiomers or mixtures of diastereomers. Thus, also provided herein is the use of stereomerically pure forms of such compounds, as well as the use of mixtures of those forms. For example, mixtures comprising equal or unequal amounts of the enantiomers of a particular immunomodulatory compounds may be used. These isomers may be asymmetrically synthesized or resolved using standard techniques such as chiral columns or chiral resolving agents. See, e.g., Jacques, J., et al., Enantiomers, Racemates and Resolutions (Wiley-Interscience, New York, 1981); Wilen, S. H., et al., Tetrahedron 33:2725 (1977); Eliel, E. L., Stereochemistry of Carbon Compounds (McGraw-Hill, N Y, 1962); and Wilen, S. H., Tables of Resolving Agents and Optical Resolutions p. 268 (E. L. Eliel, Ed., Univ. of Notre Dame Press, Notre Dame, Ind., 1972).

Immunomodulatory compounds provided herein include, but are not limited to, 1-oxo- and 1,3 dioxo-2-(2,6-dioxopiperidin-3-yl) isoindolines substituted with amino in the benzo ring as described in U.S. Pat. No. 5,635,517 which is incorporated herein by reference.

These compounds have the structure I:

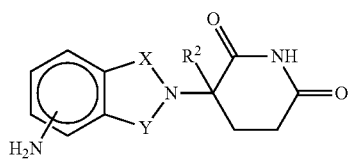

in which one of X and Y is C=O, the other of X and Y is C=O or $CH_2$, and $R^2$ is hydrogen or lower alkyl, in particular methyl. Specific immunomodulatory compounds include, but are not limited to:

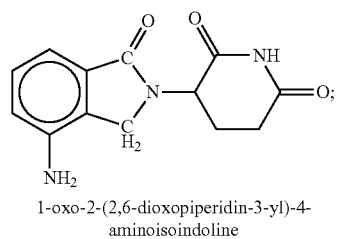

1-oxo-2-(2,6-dioxopiperidin-3-yl)-4-aminoisoindoline

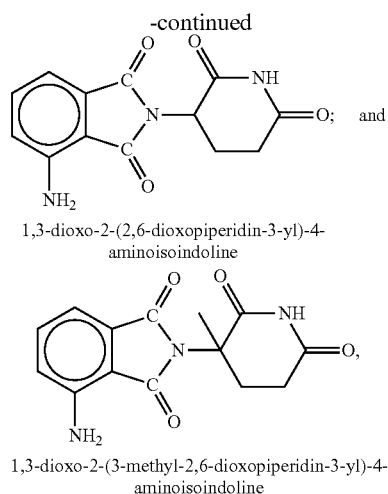

1,3-dioxo-2-(2,6-dioxopiperidin-3-yl)-4-aminoisoindoline 1,3-dioxo-2-(3-methyl-2,6-dioxopiperidin-3-yl)-4-aminoisoindoline and optically pure isomers thereof.

The compounds can be obtained via standard, synthetic methods (see e.g., U.S. Pat. No. 5,635,517, incorporated herein by reference). The compounds are also available from Celgene Corporation, Warren, N.J.

Other drugs, useful in the compositions described herein, belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein by reference. Representative compounds are of formula:

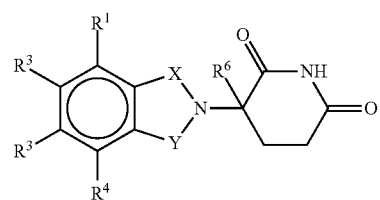

in which: one of X and Y is C=O and the other of X and Y is C=O or $CH_2$; (i) each of $R^1$, $R^2$, $R^3$, and $R^4$, independently of the others, is halo, alkyl of 1 to 4 carbon atoms, or alkoxy of 1 to 4 carbon atoms or (ii) one of $R^1$, $R^2$, $R^3$, and $R^4$ is $-NHR^5$ and the remaining of $R^1$, $R^2$, $R^3$, and $R^4$ are hydrogen; $R^5$ is hydrogen or alkyl of 1 to 8 carbon atoms; $R^6$ is hydrogen, alkyl of 1 to 8 carbon atoms, benzyl, or halo; provided that $R^6$ is other than hydrogen if X and Y are C=O and (i) each of $R^1$, $R^2$, $R^3$, and $R^4$ is fluoro or (ii) one of $R^1$, $R^2$, $R^3$, or $R^4$ is amino.

Compounds representative of this class are of the formulas:

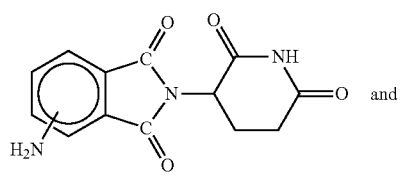

-continued

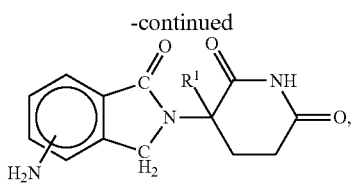

wherein $R^1$ is hydrogen or methyl. In a separate embodiment, provided herein is the use of enantiomerically pure forms (e.g. optically pure (R) or (S) enantiomers) of these compounds.

Other specific immunomodulatory compounds are the tetra substituted 2-(2,6-dioxopiperidin-3-yl)-1-oxoisoindolines described in U.S. Pat. No. 5,798,368, which is incorporated herein by reference. Representative compounds are of formula:

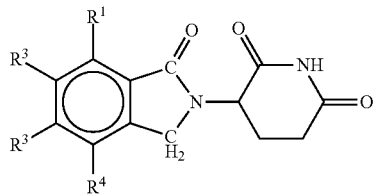

wherein each of $R^1$, $R^2$, $R^3$, and $R^4$, independently of the others, is halo, alkyl of 1 to 4 carbon atoms, or alkoxy of 1 to 4 carbon atoms.

Other specific immunomodulatory compounds are 1-oxo and 1,3-dioxo-2-(2,6-dioxopiperidin-3-yl)isoindolines disclosed in U.S. Pat. No. 6,403,613, which is incorporated herein by reference. Representative compounds are of formula:

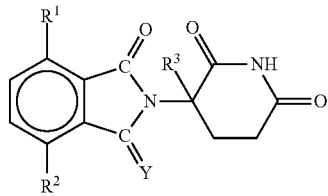

in which
Y is oxygen or $H_2$,
a first of $R^1$ and $R^2$ is halo, alkyl, alkoxy, alkylamino, dialkylamino, cyano, or carbamoyl, the second of $R^1$ and $R^2$, independently of the first, is hydrogen, halo, alkyl, alkoxy, alkylamino, dialkylamino, cyano, or carbamoyl, and $R^3$ is hydrogen, alkyl, or benzyl.

Specific examples of the compounds are of formula:

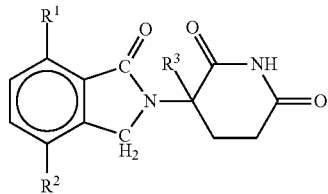

wherein a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl. Specific examples include, but are not limited to, 1-oxo-2-(2,6-dioxopiperidin-3-yl)-4-methylisoindoline.

Other representative compounds are of formula:

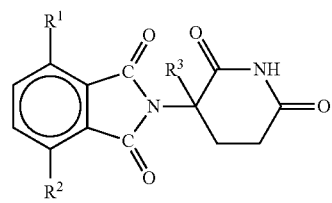

wherein: a first of $R^1$ and $R^2$ is halo, alkyl of from 1 to 4 carbon atoms, alkoxy of from 1 to 4 carbon atoms, dialkylamino in which each alkyl is of from 1 to 4 carbon atoms, cyano, or carbamoyl; the second of $R^1$ and $R^2$, independently of the first, is hydrogen, halo, alkyl of from 1 to 4 carbon atoms, alkoxy of from 1 to 4 carbon atoms, alkylamino in which alkyl is of from 1 to 4 carbon atoms, dialkylamino in which each alkyl is of from 1 to 4 carbon atoms, cyano, or carbamoyl; and $R^3$ is hydrogen, alkyl of from 1 to 4 carbon atoms, or benzyl.

Other specific compounds provided herein are of formula:

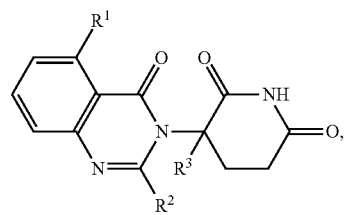

and pharmaceutically acceptable salts, solvates, and stereoisomers thereof, wherein:
$R^1$ is: hydrogen; halo; —$(CH_2)_n$OH; $(C_1\text{-}C_6)$alkyl, optionally substituted with one or more halo;
$(C_1\text{-}C_6)$alkoxy, optionally substituted with one or more halo; or
—$(CH_2)_n$NHR$^a$, wherein R$^a$ is:
hydrogen;
$(C_1\text{-}C_6)$alkyl, optionally substituted with one or more halo;
—$(CH_2)_n$-(6 to 10 membered aryl);
—C(O)—$(CH_2)_n$-(6 to 10 membered aryl) or —C(O)—$(CH_2)_n$-(6 to 10 membered heteroaryl), wherein the aryl or heteroaryl is optionally substituted with one or more of: halo; —$SCF_3$; $(C_1\text{-}C_6)$ alkyl, itself optionally substituted with one or more halo; or $(C_1\text{-}C_6)$alkoxy, itself optionally substituted with one or more halo;
—C(O)—$(C_1\text{-}C_8)$alkyl, wherein the alkyl is optionally substituted with one or more halo;
—C(O)—$(CH_2)_n$—$(C_3\text{-}C_{10}$-cycloalkyl);

—C(O)—(CH$_2$)$_n$—NR$^b$R$^c$, wherein R$^b$ and R$^c$ are each independently: hydrogen;
(C$_1$-C$_6$)alkyl, optionally substituted with one or more halo;
(C$_1$-C$_6$)alkoxy, optionally substituted with one or more halo; or 6 to 10 membered aryl, optionally substituted with one or more of: halo;
(C$_1$-C$_6$)alkyl, itself optionally substituted with one or more halo; or
(C$_1$-C$_6$)alkoxy, itself optionally substituted with one or more halo;
—C(O)—(CH$_2$)$_n$—O—(C$_1$-C$_6$)alkyl; or
—C(O)—(CH$_2$)$_n$—O—(CH$_2$)$_n$-(6 to 10 membered aryl);
R$^2$ is: hydrogen; —(CH$_2$)$_n$OH; phenyl; —O—(C$_1$-C$_6$)alkyl; or (C$_1$-C$_6$)alkyl, optionally substituted with one or more halo;
R$_3$ is: hydrogen; or (C$_1$-C$_6$)alkyl, optionally substituted with one or more halo; and
n is 0, 1, or 2.

Specific examples include, but are not limited to, 3-(5-amino-2-methyl-4-oxo-4H-quinazolin-3-yl)-piperidine-2,6-dione ("Compound A"), which has the following structure:

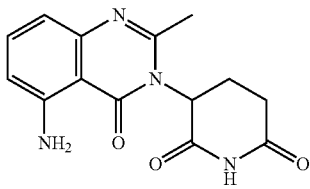 [SMILES: Cc1nc2cccc(N)c2c(=O)n1C1CCC(=O)NC1=O]

or an enantiomer or a mixture of enantiomers thereof or a pharmaceutically acceptable salt, solvate, hydrate, co-crystal, clathrate, or polymorph thereof.

Compound A can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound A is in a crystalline form described in U.S. Provisional Pat. App. No. 61/451,806, filed Mar. 11, 2011, which is incorporated herein by reference in its entirety. In some embodiments, the hydrochloride salt of Compound A is used in the methods provided herein. Methods of treating, preventing and/or managing cancers and other diseases using Compound A are described in U.S. Pat. No. 8,802,685, which is incorporated herein by reference in its entirety.

Other specific compounds provided herein are of formula:

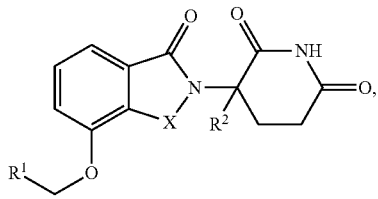

or a pharmaceutically acceptable salt, solvate or stereoisomer thereof, wherein:
X is C=O or CH$_2$;
R$^1$ is Y—R3;
R$^2$ is H or (C$_1$-C$_6$)alkyl;

Y is: 6 to 10 membered aryl, heteroaryl or heterocycle, each of which may be optionally substituted with one or more halogen; or a bond;
R$^3$ is: —(CH$_2$)$_n$-aryl, —O—(CH$_2$)$_n$-aryl or —(CH$_2$)$_n$—O-aryl, wherein the aryl is optionally substituted with one or more of: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen;
—(CH$_2$)$_n$-heterocycle, —O—(CH$_2$)$_n$-heterocycle or —(CH$_2$)$_n$—O-heterocycle, wherein the heterocycle is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; or
—(CH$_2$)n-heteroaryl, —O—(CH$_2$)$_n$-heteroaryl or —(CH$_2$)$_n$—O-heteroaryl, wherein the heteroaryl is optionally substituted with one or more: (C$_1$-C$_6$)alkyl, itself optionally substituted with one or more halogen; (C$_1$-C$_6$)alkoxy, itself substituted with one or more halogen; oxo; amino; carboxyl; cyano; hydroxyl; halogen; deuterium; 6 to 10 membered aryl or heteroaryl, optionally substituted with one or more (C$_1$-C$_6$)alkyl, (C$_1$-C$_6$)alkoxy or halogen; —CONH$_2$; or —COO—(C$_1$-C$_6$)alkyl, wherein the alkyl may be optionally substituted with one or more halogen; and n is 0, 1, 2 or 3.

Specific examples include, but are not limited to, 3-(4-((4-(morpholinomethyl)benzyl)oxy)-1-oxoisoindolin-2-yl)piperidine-2,-6-dione. In one embodiment, the compound is the (S) stereoisomer of 3-(4-((4-(morpholinomethyl)benzyl)oxy)-1-oxoisoindolin-2-yl)piperidine-2,-6-dione ("Compound B") e.g., for use in the methods described herein. Racemic 3-(4-((4-(morpholinomethyl)benzyl)oxy)-1-oxoisoindolin-2-yl)piperidine-2,6-dione and methods of preparing the same have been reported in U.S. Patent Publication No. 2011/0196150, which is incorporated herein by reference in its entirety. Compound B has the following structure:

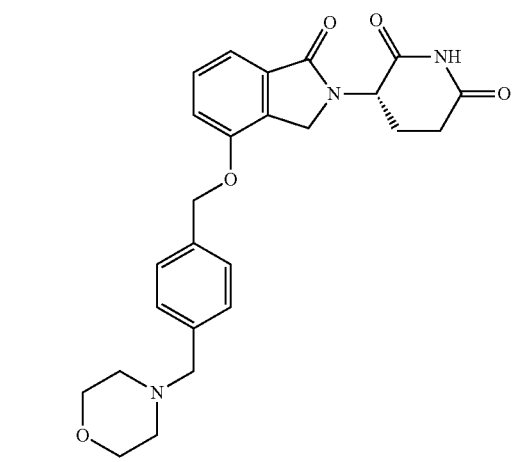 [SMILES: O=C1CC[C@H](N2Cc3c(OCc4ccc(CN5CCOCC5)cc4)cccc3C2=O)C(=O)N1]

All of the compounds described can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques. Additional information on immunomodulatory compounds, their preparation, and use can be found, for example, in U.S. Patent Application Publication Nos. US20060188475, US20060205787, and US20070049618, each of which is incorporated by reference herein in its entirety.

If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

6.4. Chimeric Antigen Receptors

In certain embodiments, any of the anti-BCMA antibodies, or BCMA-binding portions thereof, is incorporated into a chimeric antigen receptor, e.g., as the BCMA targeting domain or as part of a BCMA targeting domain. In specific embodiments, the CAR comprises a BCMA-binding antibody fragment as provided herein, e.g., a single chain Fv fragment or an Fab fragment.

In certain embodiments, chimeric antigen receptors (CARs) are artificial membrane-bound proteins that direct a T lymphocyte or natural killer (NK) cell to an antigen, e.g., BCMA, and stimulate the T lymphocyte or NK cell to kill a cell displaying the antigen, e.g., BCMA. See, e.g., Eshhar, U.S. Pat. No. 7,741,465. At a minimum, the CARs provided herein comprise an extracellular domain that binds to BCMA; a transmembrane domain, and an intracellular (cytoplasmic) signaling domain that transmits a primary activation signal to an immune cell. All other conditions being satisfied, when the CAR is expressed on the surface of, e.g., a T lymphocyte, and the extracellular domain of the CAR binds to BCMA, the intracellular signaling domain transmits a signal to the T lymphocyte to activate and/or proliferate, and, if BCMA is present on a cell surface, to kill the cell expressing the BCMA.

Because T lymphocytes require at least two signals, a primary activation signal and a costimulatory signal, in order to fully activate, typically CARs also comprise a costimulatory domain such that binding of the extracellular domain to BCMA on a cell surface results in transmission of both a primary activation signal and a costimulatory signal.

In certain embodiments, the intracellular domain of the CAR is or comprises an intracellular domain or motif of a protein that is expressed by T lymphocytes and triggers activation and/or proliferation of said T lymphocytes. Such a domain or motif is able to transmit a primary antigen-binding signal that is necessary for the activation of a T lymphocyte in response to the antigen's binding to the CAR's extracellular portion. Typically, this domain or motif comprises, or is, an ITAM (immunoreceptor tyrosine-based activation motif). ITAM-containing polypeptides suitable for CARs include, for example, the zeta CD3 chain (CD3ζ) or ITAM-containing portions thereof. In a specific embodiment, the intracellular domain is a CD3ζ intracellular signaling domain. In other specific embodiments, the intracellular domain is from a lymphocyte receptor chain, a TCR/CD3 complex protein, an Fc receptor subunit or an IL-2 receptor subunit. In certain embodiments, the primary signaling domain is, or comprises, a signaling domain from TCRζ, FcRγ, FcRβ, CD3γ, CD3δ, CD3ε, CD5, CD22, CD79a, CD79b, CD278, FcεRI, DAP10, DAP12, or CD66d.

In certain embodiments, the CAR additionally comprises one or more co-stimulatory domains or motifs, e.g., as part of the intracellular domain of the polypeptide. The one or more co-stimulatory domains or motifs can be, or comprise, one or more of a co-stimulatory CD27 polypeptide sequence, a co-stimulatory CD28 polypeptide sequence, a co-stimulatory OX40 (CD134) polypeptide sequence, a co-stimulatory 4-1BB (CD137) polypeptide sequence, or a co-stimulatory inducible T-cell costimulatory (ICOS) polypeptide sequence, or other costimulatory domain or motif. In certain other embodiments, the costimulatory domain is or comprises a functional signaling domain derived from one or more of a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, CD2, CD7, CD27, CD30, CD40, CDS, ICAM-1, LFA-1(CD11a/CD18), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, or PAG/Cbp The transmembrane region can be any transmembrane region that can be incorporated into a functional CAR, typically a transmembrane region from a CD4 or a CD8 molecule. In certain embodiments, the transmembrane domain of the CAR is from an immune system protein that normally transmits an inhibitory signal to such immune system cells, e.g., a transmembrane domain from CTLA4 (Cytotoxic T-Lymphocyte Antigen 4 or Cytotoxic T-Lymphocyte Associated protein 4) or PD-1 (Programmed Death-1).

In certain embodiments, any of the T lymphocytes provided herein, which comprise a plurality of cell death polypeptides, comprise a transmembrane domain from CTLA4 or PD-1 (Programmed Cell Death 1) In a specific embodiment, a T lymphocyte expressing said polypeptide, or any of such polypeptides described herein, is activated or stimulated to proliferate when said polypeptide binds to said antigen. In a specific embodiment, the polypeptide, when expressed on the surface of a T lymphocyte, directs the T lymphocyte to kill a cell expressing said antigen.

In specific embodiments of any of the polypeptides herein, in which the transmembrane domain of the polypeptide is from CTLA4, the CTLA4 transmembrane domain is from a mammalian CTLA4, e.g., human, primate, or rodent, e.g., murine CTLA4. Preferably, the transmembrane domain does not comprise amino acids from the intracellular domain, extracellular domain, or either intracellular or extracellular domain of CTLA4 or PD-1. Specific, non-limiting examples of CTLA4 or PD-1 transmembrane domain sequences are provided below.

In a specific embodiment, the CTLA4 transmembrane domain is the polypeptide sequence encoded by exon 3 of a human CTLA4 gene. In another specific embodiment, the CTLA4 transmembrane domain is or comprises the amino acid sequence PEPCPDSDFLLWILAAVSSGLFFYSFLL-TAVSLSKM (in three-letter code, Pro-Glu-Pro-Cys-Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu-Ser-Lys-Met) (SEQ ID NO:61). In another specific embodiment, the CTLA4 transmembrane domain is or comprises the polypeptide sequence encoded by nucleotides 610-722 of GenBank Accession No. NM_005214.4. In another specific embodiment, the CTLA4 transmembrane domain is or comprises the amino acid sequence PDSD-FLLWILAAVSSGLFFYSFLLTAVSL (in three-letter code, Pro-Asp-Ser-Asp-Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val-Ser-Leu) (SEQ ID NO:62). In another specific embodiment, the CTLA4 transmembrane domain is or comprises the polypeptide sequence encoded by nucleotides 636-699 of GenBank Accession No. NM_005214.4. In another specific embodiment, the CTLA4 transmembrane domain is or comprises the amino acid sequence FLLWI-LAAVSSGLFFYSFLLTAV (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr-Ala-Val) (SEQ ID NO:63). See, e.g., Ensembl protein reference no. ENSP00000303939.3. In another specific embodiment, the CTLA4 transmembrane domain is or comprises the polypeptide sequence FLLWI-LAAVSSGLFFYSFLLT (in three-letter code, Phe-Leu-Leu-Trp-Ile-Leu-Ala-Ala-Val-Ser-Ser-Gly-Leu-Phe-Phe-Tyr-Ser-Phe-Leu-Leu-Thr) (SEQ ID NO:64), see, e.g., UNIPROT Accession No. P16410. In another specific embodiment, the CTLA4 transmembrane domain is or comprises the polypeptide sequence FLLWILVA-VSLGLFFYSFLVSAVSLS (in three-letter code, Phe-Leu-Leu-Trp-Ile-Leu-Val-Ala-Val-Ser-Leu-Gly-Leu-Phe-Phe-Tyr-Ser-Phe-Leu-Val-Ser-Ala-Val-Ser-Leu-Ser) (SEQ ID NO:65). See, e.g., Shin et al., Blood 119:5678-5687 (2012). In another specific embodiment, the PD-1 transmembrane domain is or comprises the amino acid sequence TLVVGVVGGLLGSLVLLVWVLAVICSRAA (in three-letter code, Thr-Leu-Val-Val-Gly-Val-Val-Gly-Gly-Leu-Leu-Gly-Ser-Leu-Val-Leu-Leu-Val-Trp-Val-Leu-Ala-Val-Ile-Cys-Ser-Arg-Ala-Ala) (SEQ ID NO:66). See Finger et al., Gene 197(1-2):177-187 (1997). In another specific embodiment, the PD-1 transmembrane domain is or comprises the amino acid sequence VGVVGGLLGSLVLL-VWVLAVI (in three-letter code, Val-Gly-Val-Val-Gly-Gly-Leu-Leu-Gly-Ser-Leu-Val-Leu-Leu-Val-Trp-Val-Leu-Ala-Val-Ile) (SEQ ID NO:67). See, e.g., UNIPROT Accession No. Q15116. In another specific embodiment, the PD-1 transmembrane domain is or comprises the amino acid sequence FQTLVVGVVGGLLGSLVLLVWVLAVI (in three-letter code, Phe-Glu-Thr-Leu-Val-Val-Gly-Val-Val-Gly-Gly-Leu-Leu-Gly-Ser-Leu-Val-Leu-Leu-Val-Trp-Val-Leu-Ala-Val-Ile) (SEQ ID NO:68). See, e.g., GenBank Accession No. NM_005018.2.

In certain embodiments, a nucleotide sequence that encodes one of the transmembrane polypeptides disclosed herein comprises a nucleotide sequence that encodes any of the amino acid sequences disclosed in SEQ ID NO:61, SEQ ID NO:62, SEQ ID NO:63, SEQ ID NO:64, SEQ ID NO:65, SEQ ID NO:66, SEQ ID NO:67 or SEQ ID NO:68. In another specific embodiment, the PD-1 transmembrane domain is or comprises at least 10, 11, 12, 13, 14, 15, 16, 17, 18, 19, 20 or 21 consecutive amino acids disclosed in SEQ ID NO:61, SEQ ID NO:62, SEQ ID NO:63, SEQ ID NO:64, SEQ ID NO:65, SEQ ID NO:66, SEQ ID NO:67 or SEQ ID NO:68. In certain embodiments, a nucleotide sequence that encodes one of the polypeptides disclosed herein comprises a nucleotide sequence that encodes at least 10, 11, 12, 13, 14, 15, 16, 17, 18, 19, 20 or 21 consecutive amino acids disclosed in SEQ ID NO:61, SEQ ID NO:62, SEQ ID NO:63, SEQ ID NO:64, SEQ ID NO:65, SEQ ID NO:66, SEQ ID NO:67 or SEQ ID NO:68. In constructing the polypeptide, e.g. CAR, in certain embodiments, human sequences may be combined with non-human sequences. For example, a polypeptide, e.g. CAR comprising human extracellular and intracellular domain amino acid sequences may comprise a transmembrane domain from a non-human species; e.g., may comprise a murine CTLA4 transmembrane domain or a murine PD-1 transmembrane domain. In a more specific embodiment, the polypeptide, e.g. CAR, comprises human amino acid sequences for the extracellular and intracellular domains, and comprises a transmembrane domain having, or consisting of, the amino acid sequence of SEQ ID NO:65.

6.5. Pharmaceutical Compositions

In another aspect, provided herein are pharmaceutical compositions comprising any of the anti-BCMA antibodies or BCMA-binding fragments thereof. In certain embodiments, the pharmaceutical compositions comprise a pharmaceutically acceptable vehicle.

In certain embodiments, formulations of the anti-BCMA antibodies or BCMA binding fragments thereof provided herein are prepared for storage and use by combining a purified binding agent of the present invention with a pharmaceutically acceptable vehicle (e.g., a carrier or excipient). Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (See, e.g., Remington: The Science and Practice of Pharmacy, 22' Edition, 2012, Pharmaceutical Press, London).

The pharmaceutical compositions provided herein can be formulated for administration in any number of ways for either local or systemic treatment. Pharmaceutical formulations provided herein can be formulated for topical administration, e.g., by epidermal or transdermal patches, ointments, lotions, creams, or gels; or in the form of drops, suppositories, sprays, liquids and powders; for pulmonary administration by inhalation or insufflation, including by nebulizer, or intratracheal or intranasal administration; or parenteral administration, including intravenous, intraarterial, intratumoral, subcutaneous, intraperitoneal, intramuscular (e.g., injection or infusion), or intracranial (e.g., intrathecal or intraventricular) administration.

The therapeutic formulation of the anti-BCMA antibodies or BCMA binding fragments thereof, presented herein, can be in unit dosage form. Such formulations include tablets, pills, capsules, powders, granules, solutions or suspensions in water or non-aqueous media, or suppositories, or plastic blood bags or the like suitable for, e.g., single-dose intravenous, or intraarterial administration.

In certain embodiments, the anti-BCMA antibodies or BCMA binding fragments thereof, presented herein, are entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in Remington: The Science and Practice of Pharmacy, 22' Edition, 2012, Pharmaceutical Press, London.

In certain embodiments, the pharmaceutical formulations provided herein include one or more anti-BCMA antibodies or BCMA binding fragments thereof as provided herein, complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

6.6. Polynucleotides and Methods of Producing Polypeptides and Antibodies

In another aspect, provided herein are polynucleotides, e.g., polynucleotide sequences, that encode any of the anti-BCMA antibodies or BCMA binding fragments thereof, including heavy or light chains, and/or CDR sequences for each. In certain embodiments, provided herein are polynucleotides comprising polynucleotides that encode a polypeptide (or a fragment of a polypeptide) that specifically binds BCMA. The term "polynucleotides that encode a polypeptide" encompasses a polynucleotide that includes only coding sequences for the polypeptide as well as a polynucleotide which includes additional coding and/or non-coding sequences. For example, in some embodiments, the invention provides a polynucleotide comprising a polynucleotide sequence that encodes an antibody to human BCMA or encodes a fragment of such an antibody (e.g., a fragment comprising the BCMA binding site). The polynucleotides of the invention can be in the form of RNA or in the form of DNA. In specific embodiments, the DNA can be, e.g., cDNA, genomic DNA, and synthetic DNA; and can be double-stranded or single-stranded, and if single stranded can be the coding strand or non-coding (anti-sense) strand.

In specific embodiments, the polynucleotides provided herein encode an antibody light chain variable region comprising, consisting essentially or, or consisting of the nucleotide sequence of SEQ ID NO:5.

In other specific embodiments, the polynucleotides provided herein encode an antibody heavy chain variable region chain comprising, consisting essentially or, or consisting of the nucleotide sequence of SEQ ID NO:16, SEQ ID NO:27, SEQ ID NO:38, SEQ ID NO:49, or SEQ ID NO:60.

In other specific embodiments, the polynucleotides provided herein encode an antibody light chain variable region comprising, consisting essentially or, or consisting of the nucleotide sequence of SEQ ID NO:5, and encode an antibody heavy chain variable region chain comprising, consisting essentially or, or consisting of the nucleotide sequence of SEQ ID NO:16. In other specific embodiments, the polynucleotides provided herein encode an antibody light chain variable region comprising, consisting essentially or, or consisting of the nucleotide sequence of SEQ ID NO:5, and encode an antibody heavy chain variable region chain comprising, consisting essentially or, or consisting of the nucleotide sequence of SEQ ID NO:27. In other specific embodiments, the polynucleotides provided herein encode an antibody light chain variable region comprising, consisting essentially or, or consisting of the nucleotide sequence of SEQ ID NO:5, and encode an antibody heavy chain variable region chain comprising, consisting essentially or, or consisting of the nucleotide sequence of SEQ ID NO:38. In other specific embodiments, the polynucleotides provided herein encode an antibody light chain variable region comprising, consisting essentially or, or consisting of the nucleotide sequence of SEQ ID NO:5, and encode an antibody heavy chain variable region chain comprising, consisting essentially or, or consisting of the nucleotide sequence of SEQ ID NO:49. In other specific embodiments, the polynucleotides provided herein encode an antibody light chain variable region comprising, consisting essentially or, or consisting of the nucleotide sequence of SEQ ID NO:5, and encode an antibody heavy chain variable region chain comprising, consisting essentially or, or consisting of the nucleotide sequence of SEQ ID NO:60.

Any of the polynucleotides provided herein may be comprised within, and/or expressed by, a polynucleotide vector. In certain embodiments, the vector is comprised within a host cell. Such a host cell, after transformation or transfection with the vector provided herein, expresses, or is capable of expressing, the BCMA antibody-encoding polynucleotide sequences provided herein. In certain embodiments, the polynucleotides provided herein are is operatively linked with one or more control sequences in the vector so as to facilitate expression of the BCMA-binding antibody.

The term "vector" as used herein means a nucleic acid molecule used as a vehicle to transfer genetic material into a cell, and encompasses, without limitation, plasmids, viral genomes (including replication-incompetent viral genomes and viral genomes in multiple segments), cosmids and artificial chromosomes. In general, engineered vectors comprise an origin of replication, a multiple cloning site and a selectable marker. The vector itself is generally a nucleotide sequence, commonly a DNA sequence, that comprises an insert (transgene, e.g., any of the BCMA antibody-encoding sequences described herein) and a larger sequence that serves as the backbone of the vector. Vectors may encompass additional features besides the transgene insert and a backbone: promoter, genetic marker, antibiotic resistance, reporter gene, targeting sequence, protein purification tag. Vectors called expression vectors enable expression of the transgene in the target cell, and generally have control sequences such as a promoter sequence that drives expression of the transgene. Insertion of a vector into the target cell is usually called "transformation" for bacterial cells, and "transfection" for eukaryotic cells; insertion of a viral vector into a mammalian cell is also referred to as "transduction".

As used herein, the term "host cell" refers to a cell into which a polynucleotide encoding a BCMA-binding antibody provided herein is introduced by way of transformation, transfection and the like. The term refers not only to the particular cells that are transfected, transformed or transduced, but to the progeny such cells. Because certain modifications may occur in succeeding generations due to either mutation or environmental influences, such progeny may not be identical to parent cells, but are still included within the scope of the term as used herein.

As used herein, the term "expression" includes any step involved in the production of a binding molecule of the invention including, but not limited to, transcription (e.g., from a polynucleotide provided herein or a polynucleotide encoding a BCMA-binding antibody or BCMA-binding fragment thereof provided herein), and, in certain embodiments, post-transcriptional modification, translation, post-translational modification, and secretion of e.g., a BCMA-binding antibody or BCMA-binding fragment thereof provided herein.

The term "control sequences" refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize, and a vector may comprise, promoters, polyadenylation signals, and enhancers.

As used herein, a nucleic acid or polynucleotide is "operably linked" when it is placed into a functional relationship with another nucleic acid sequence. For example, a promoter nucleic acid sequence is operably linked to a nucleic acid sequence encoding a BCMA-binding antibody or BCMA-binding fragment thereof if the promoter drives expression of the BCMA-binding antibody or BCMA-binding fragment thereof; or, as another example, a nucleic acid sequence for a presequence or secretory leader is operably linked to a nucleic acid encoding a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences that are linked are contiguous, and, in the case of a secretory leader, contiguous and in the same reading frame. However, enhancers do not have to be contiguous. Linking may be accomplished by, e.g., ligation at convenient restriction sites. If such sites do not exist, the synthetic oligonucleotide adaptors or linkers are used in accordance with conventional practice.

The terms "host cell," "target cell" or "recipient cell" include any individual cell or cell culture that can be or has/have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, macaque or human. Suitable host cells include prokaryotes and eukaryotic host cells including yeasts, fungi, insect cells and mammalian cells.

The antibodies or fragments thereof may be produced in bacteria. After expression, the binding molecule of the invention, preferably the binding molecule is isolated from the *E. coli* cell paste in a soluble fraction and can be purified through, e.g., affinity chromatography and/or size exclusion. Final purification can be carried out similar to the process for purifying antibody expressed e.g., in CHO cells.

In addition to prokaryotes, eukaryotic microbes such as filamentous fungi or yeast are suitable cloning or expression hosts for the binding molecule of the invention. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*, *Kluyveromyces* hosts such as, e.g., *K. lactis*, *K. fragilis* (ATCC 12424), *K. bulgaricus* (ATCC 16045), *K. wickeramii* (ATCC 24178), *K. waltii* (ATCC 56500), *K. drosophilarum* (ATCC 36906), *K. thermotolerans*, and *K. marxianus*; *Yarrowia* (EP 402 226); *Pichia pastoris* (EP 183 070); *Candida*; *Trichoderma reesia* (EP 244 234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated binding molecule of the invention, preferably antibody derived binding molecules are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, *Arabidopsis* or tobacco can also be utilized as hosts. Cloning and expression vectors useful in the production of proteins in plant cell culture are known to those of skill in the art. See, e.g. Hiatt et al., *Nature* (1989) 342: 76-78, Owen et al. (1992) *Bio/Technology* 10: 790-794, Artsaenko et al. (1995) *The Plant J.* 8: 745-750, and Fecker et al. (1996) *Plant Mol. Biol.* 32: 979-986.

Propagation of vertebrate cells in culture (tissue culture), and expression of proteins therefrom, has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77: 4216 (1980)); mouse sertoli cells (TM4, Mather, *Biol. Reprod.* 23: 243-251 (1980)); monkey kidney cells (CV1 ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, 1413 8065); mouse mammary tumor (MMT 060562, ATCC CCLS 1); TRI cells (Mather et al., *Annals N.Y. Acad. Sci.* 383:44-68 (1982)); MRC 5 cells; FS4 cells; and a human hepatoma line (Hep G2).

When using recombinant techniques, the BCMA-binding antibodies or fragments thereof provided herein can be produced intracellularly, in the periplasmic space, or directly secreted into the medium. If the binding molecule is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The BCMA antibodies or BCMA-binding fragments thereof, prepared from the host cells, can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the binding molecule of the invention comprises a $CH_3$ domain, the Bakerbond ABXmresin (J. T. Baker, Phillipsburg, N.J.) may be used for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromato-focusing, SDS-PAGE, and ammonium sulfate precipitation, according to standard procedures, may be used depending on the antibody to be recovered.

In another aspect, processes are provided for producing binding molecules of the invention, said processes comprising culturing a host cell defined herein under conditions allowing the expression of the binding molecule and recovering the produced binding molecule from the culture.

The term "culturing" refers to the in vitro maintenance, differentiation, growth, proliferation and/or propagation of cells under suitable conditions in a medium.

6.7. Methods of Use

In another aspect, provided herein are methods of use of the anti-BCMA antibodies or BCMA binding fragments thereof, e.g., methods of treatment using such antibodies or antibody fragments.

In certain embodiments, provided herein is a method of treating a subject having a BCMA-related disease or disorder, comprising administering a therapeutically effective amount of one or more of the anti-BCMA antibodies, or BCMA-binding fragments thereof, to the subject. Also provided herein is a method of treating a subject having a plasma cell-related disease or disorder, comprising administering a therapeutically effective amount of one or more of the anti-BCMA antibodies, or BCMA-binding fragments thereof, to the subject. Also provided herein is a method of treating a subject having a B cell-related disease or disorder, comprising administering a therapeutically effective amount of one or more of the anti-BCMA antibodies, or BCMA-binding fragments thereof, to the subject. In specific embodiments, the BCMA-related disorder is multiple myeloma, plasmacytoma, plasma cell leukemia, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance, and smoldering multiple myeloma.

Also provided herein is a method of suppressing the growth of multiple myeloma cells, comprising contacting the multiple myeloma cells with one or more of the anti-BCMA antibodies, or BCMA-binding fragments thereof, provided herein. Further provided herein is a method of reducing the rate of growth of multiple myeloma cells, comprising contacting the multiple myeloma cells with one or more of the anti-BCMA antibodies, or BCMA-binding fragments thereof, provided herein.

In any of the methods, e.g., methods of treatment, provided herein, the antibody or BCMA-binding fragment thereof is a naked antibody or fragment, that is, the antibody or fragment has not been modified to include a toxic moiety. In any of the methods, e.g., methods of treatment, provided herein, the antibody or BCMA-binding fragment thereof is part of an antibody-drug-conjugate (ADC), e.g., an ADC as described in Section 5.3, above.

In any of the methods of treatment provided herein, the anti-BCMA antibodies or BCMA binding fragments thereof are provided or administered in a therapeutically effective amount. In various embodiments, the therapeutically effective amount is from $1 \times 10^5$ to $5 \times 10^5$, $5 \times 10^5$ to $1 \times 10^6$, $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$ nanomoles of said antibodies or fragments. In various other embodiments, the therapeutically effective amount is from $1 \times 10^5$ to $5 \times 10^5$, $5 \times 10^5$ to $1 \times 10^6$, $1 \times 10^6$ to $5 \times 10^6$, $5 \times 10^6$ to $1 \times 10^7$, $1 \times 10^7$ to $5 \times 10^7$, $5 \times 10^7$ to $1 \times 10^8$, $1 \times 10^8$ to $5 \times 10^8$, $5 \times 10^8$ to $1 \times 10^9$ nanomoles of said antibodies or fragments.

The anti-BCMA antibodies or BCMA-binding fragments may be administered to a patient in need thereof at any dosing schedule deemed suitable by attending physicians or clinicians, e.g., once every 1, 2, 3, 4, 5, 6 or 7 days, or once every 1, 2, 3, 4, 5, 6, 7, 8, 9 or 10 weeks. The anti-BCMA antibodies or BCMA-binding fragments thereof may be administered for a period of time, e.g., 1, 2, 3, or 4 weeks, followed by a rest with no administration of the antibody or antibody fragment. Such an administration-rest cycle may be repeated 2, 3, 4 or 5 times.

In certain embodiments, a patient to whom the BCMA antibodies or BCMA-binding fragments thereof are administered has previously received 1, 2, 3 or more lines of therapy the previous lines of therapy can involve administration of one or more of lenalidomide (REVLIMID), pomalidomide (POMALYST), thalidomide (THALOMID), bortezomib (VELCADE), dexamethasone, cyclophosphamide, doxorubicin (ADRIAMYCIN, RUBEX), carfilzomib (KRYPOLIS), iaxizomib (NINLARO), cisplatin (PLATINOL), doxorubicin (ADRIAMYCIN), etoposide (ETOPOPHOS), an anti-CD38 antibody such as daratumumab (DARZALEX); panobinostat; or elotuzumab (EMPLICITI). In specific embodiments, such patients have received therapy with bortezomib, lenalidomide and dexamethasone (RVD); bortezomib, cyclophosphamide and dexamethasone (BCD); bortezomib, doxorubicin and dexamethasone; carfilzomib, lenalidomide and dexamethasone (CRD); ixazomib, lenalidomide and dexamethasone; bortezomib and dexamethasone; bortezomib, thalidomide and dexamethasone; lenalidomide and dexamethasone; dexamethasone, thalidomide, cisplatin, doxorubicin, cyclophosphamide, etoposide and bortezomib (VTD-PACE); lenalidomide and low-dose dexamethasone; bortezomib, cyclophosphamide and dexamethasone; carfilzomib and dexamethasone; lenalidomide alone; bortezomib alone; daratumumab alone; bortezomib, lenalidomide and dexamethasone; daratumumab, bortezomib and dexamethasone; daratumumab, lenalidomide and dexamethasone; elotuzumab, lenalidomide, and dexamethasone; elotuzumab, lenalidomide and dexamethasone; bendamustine, bortezomib and dexamethasone; bendamustine, lenalidomide, and dexamethasone; pomalidomide and dexamethasone; pomalidomide, bortezomib and dexamethasone; pomalidomide, carfilzomib and dexamethasone; bortezomib and liposomal doxorubicin; cyclophosphamide, lenalidomide, and dexamethasone; elotuzumab, bortezomib and dexamethasone; ixazomib and dexamethasone; panobinostat, bortezomib and dexamethasone; panobinostat and carfilzomib; or pomalidomide, cyclophosphamide and dexamethasone.

Administration of the BCMA antibodies or BCMA-binding fragments thereof to a patient in need thereof can be accompanied by administration of one or more additional therapies. For certain cancers, e.g., multiple myeloma, the one or more additional therapies may be one or more of lenalidomide, pomalidomide, thalidomide, bortezomib, dexamethasone, cyclophosphamide, doxorubicin, carfilzomib, iaxizomib, cisplatin, doxorubicin, etoposide, an anti-CD38 antibody such as daratumumab; panobinostat; and/or elotuzumab, either alone, in one of the combinations listed above, or in any other combination.

In certain embodiments, a patient in need thereof is administered one or more of the anti-BCMA antibodies provided herein in combination with one or more of the compounds disclosed in Section 5.3, above, e.g., in combination with lenalidomide or pomalidomide.

In certain other embodiments, a patient in need thereof is administered one or more of the anti-BCMA antibodies provided herein in combination with one or more of the following compounds.

Exemplary compounds include but are not limited to N-{[2-(2,6-dioxo(3-piperidyl)-1,3-dioxoisoindolin-4-yl] methyl}cyclopropyl-carboxamide; 3-[2-(2,6-dioxo-piperidin-3-yl)-1,3-dioxo-2,3-dihydro-1H-isoindol-4-ylmethyl]-1,1-dimethyl-urea; (−)-3-(3,4-Dimethoxy-phenyl)-3-(1-oxo-1,3-dihydro-isoindol-2-yl)-propionamide; (+)-3-(3,4-Dimethoxy-phenyl)-3-(1-oxo-1,3-dihydro-isoindol-2-yl)-pro-pionamide; (−)-{2-[1-(3-ethoxy-4-methoxyphenyl)-2-methylsulfonylethyl]-4-a-cetylaminoisoindoline-1,3-dione}; (+)-{2-[1-(3-ethoxy-4-methoxyphenyl)-2-methylsulfonylethyl]-4-acetylamino-isoindoline-1,3-dione}; Difluoromethoxy SelCIDs; 1-phthalimido-1-(3,4-diethoxyphenyl)ethane; 3-(3,4-dimethoxyphenyl)-3-(3,5-dimethoxyphenyl)acrylo nitrile; 1-oxo-2-(2,6-dioxopiperidin-3-yl)-4-aminoisoindoline; 1,3-dioxo-2-(2,6-dioxopiperidin-3-yl)-4-aminoisoindoline; 4-amino-2-(3-methyl-2,6-dioxo-piperidine-3-yl)-isoindole-1,3-dione; 3-(3-acetoamidophthalimido)-3-(3-ethoxy-4-methoxyphenyl)-N-hydroxypropion-amide; 1-oxo-2-(2,6-dioxopiperidin-3-yl)-4-methylisoindoline; Cyclopropyl-N-{2-[(1S)-1-(3-ethoxy-4-methoxyphenyl)-2-(methylsulfonyl)ethyl]-3-oxoisoindoline-4-yl}carboxamide; Substituted 2-(3-hydroxy-2,6-dioxopiperidin-5-yl)isoindoline; N-[2-(2,6-Dioxo-piperidin-3-yl)-1,3-dioxo-2,3-dihydro-1H-isoindol-5-ylmethyl]-4-trifluoromethoxybenzamide; (S)-4-chloro-N-((2-(3-methyl-2,6-dioxopiperidin-3-yl)-1,3-dioxoisoindolin-5-yl)methyl)benzamide; Pyridine-2-carboxylic acid [2-[(3S)-3-methyl-2,6-dioxo-piperidin-3-yl]-1,3-dioxo-2,3-dihydro-1H-isoi-ndol-5-ylmethyl]-amide; (S)—N-((2-(3-methyl-2,6-dioxopiperidin-3-yl)-1,3-dioxoisoindolin-5-yl)methyl)-4-(trifluoromethyl)benzamide; 3-(2, 5-dimethyl-4-oxo-4H-quinazolin-3-yl)-piperidine-2,6-dione, and the like.

In certain embodiments, a patient in need thereof is administered one or more of the anti-BCMA antibodies provided herein in combination with one or more cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl)isoindolines such as those described in U.S. Pat. Nos. 5,874,448 and 5,955,476; 1-oxo and 1,3-dioxoisoindolines substituted in the 4- or 5-position of the indoline ring (e.g., 4-(4-amino-1,3-dioxoisoindoline-2-yl)-4-carbamoylbutanoic acid) described in U.S. Pat. No. 6,380,239; isoindoline-1-one and isoindoline-1,3-dione substituted in the 2-position with 2,6-dioxo-3-hydroxypiperidin-5-yl (e.g., 2-(2,6-dioxo-3-hydroxy-5-fluoropiperidin-5-yl)-4-aminoisoindolin-1-one) described in U.S. Pat. No. 6,458,810; a class of non-polypeptide cyclic amides disclosed in U.S. Pat. Nos. 5,698,579 and 5,877,200; and isoindoleimide compounds such as those described in U.S. Patent Publication No. 2003/0045552, U.S. Patent Publication No. 2003/0096841, and International Application No. PCT/US01/50401 (International Publication No. WO 02/059106). US Patent Publication No. 2006/0205787 describes 4-amino-2-(3-methyl-2,6-dioxopiperidin-3-yl)-isoindole-1,3-dione compositions. U.S. Patent Publication No. 2007/0049618 describes isoindoleimide compounds.

In certain embodiments, a patient in need thereof is administered one or more of the anti-BCMA antibodies provided herein in combination with one or more members of a class of isoindoleimides disclosed in U.S. Pat. No. 7,091,353, U.S. Patent Publication No. 2003/0045552, and International Application No. PCT/US01/50401 (International Publication No. WO 02/059106), each of which are incorporated herein by reference. Representative compounds are of formula II:

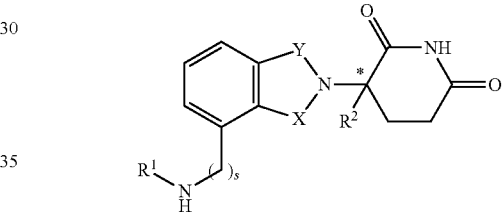

and pharmaceutically acceptable salts, hydrates, solvates, clathrates, enantiomers, diastereomers, racemates, and mixtures of stereoisomers thereof, wherein: one of X and Y is C=O and the other is $CH_2$ or C=O; $R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^3$, $C(S)NR^3R^3$ or $(C_1-C_8)$alkyl-$O(CO)R^5$; $R^2$ is H, F, benzyl, $(C_1-C_8)$alkyl, $(C_2-C_8)$alkenyl, or $(C_2-C_8)$alkynyl; $R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$; $R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl; $R^5$ is $(C_1-C_8)$alkyl, $(C_2-C_8)$alkenyl, $(C_2-C_8)$alkynyl, benzyl, aryl, or $(C_2-C_5)$heteroaryl; each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to form a heterocycloalkyl group; n is 0 or 1; and * represents a chiral-carbon center.

In specific compounds of formula II, when n is 0 then $R^1$ is $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(O)OR^4$, $(C_1-C_8)$alkyl-N (R⁶)₂, (C₁-C₈)alkyl-OR⁵, (C₁-C₈)alkyl-C(O)OR⁵, C(S)NHR³, or (C₁-C₈)alkyl-O(CO)R⁵;

R² is H or (C₁-C₈)alkyl; and R³ is (C₁-C₈)alkyl, (C₃-C₇)cycloalkyl, (C₂-C₈)alkenyl, (C₂-C₈)alkynyl, benzyl, aryl, (C₀-C₄)alkyl-(C₁-C₆)heterocycloalkyl, (C₀-C₄)alkyl-(C₂-C₅)heteroaryl, (C₅-C₈)alkyl-N(R⁶)₂; (C₀-C₈)alkyl-NH—C(O)O—R⁵; (C₁-C₈)alkyl-OR⁵, (C₁-C₈)alkyl-C(O)OR⁵, (C₁-C₈)alkyl-O(CO)R⁵, or C(O)OR⁵; and the other variables have the same definitions.

In other specific compounds of formula II, R² is H or (C₁-C₄)alkyl.

In other specific compounds of formula II, R¹ is (C₁-C₈) alkyl or benzyl.

In other specific compounds of formula II, R¹ is H, (C₁-C₈)alkyl, benzyl, CH₂OCH₃, CH₂CH₂OCH₃, or

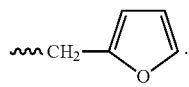

In another embodiment of the compounds of formula II, R¹ is

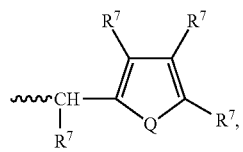

wherein Q is O or S, and each occurrence of R⁷ is independently H, (C₁-C₈)alkyl, (C₃-C₇)cycloalkyl, (C₂-C₈)alkenyl, (C₂-C₈)alkynyl, benzyl, aryl, halogen, (C₀-C₄)alkyl-(C₁-C₆)heterocycloalkyl, (C₀-C₄)alkyl-(C₂-C₅)heteroaryl, (C₀-C₈)alkyl-N(R⁶)₂, (C₁-C₈)alkyl-OR⁵, (C₁-C₈)alkyl-C(O)OR⁵, (C₁-C₈)alkyl-O(CO)R⁵, or C(O)OR⁵, or adjacent occurrences of R⁷ can be taken together to form a bicyclic alkyl or aryl ring.

In other specific compounds of formula II, R¹ is C(O)R₃.

In other specific compounds of formula II, R³ is (C₀-C₄)alkyl-(C₂-C₅)heteroaryl, (C₁-C₈)alkyl, aryl, or (C₀-C₄)alkyl-OR⁵.

In other specific compounds of formula II, heteroaryl is pyridyl, furyl, or thienyl.

In other specific compounds of formula II, R¹ is C(O)OR⁴.

In other specific compounds of formula II, the H of C(O)NHC(O) can be replaced with (C₁-C₄)alkyl, aryl, or benzyl.

Further examples of the compounds in this class include, but are not limited to: [2-(2,6-dioxo-piperidin-3-yl)-1,3-dioxo-2,3-dihydro-1H-isoindol-4-ylmethy-1]-amide; (2-(2,6-dioxo-piperidin-3-yl)-1,3-dioxo-2,3-dihydro-1H-isoindol-4-ylmethyl)-carbamic acid tert-butyl ester; 4-(aminomethyl)-2-(2,6-dioxo(3-piperidyl))-isoindoline-1,3-dione; N-(2-(2,6-dioxo-piperidin-3-yl)-1,3-dioxo-2,3-dihydro-1H-isoindol-4-ylmethyl)-acetamide; N-{(2-(2,6-dioxo(3-piperidyl))-1,3-dioxoisoindolin-4-yl)methyl}cyclopropyl-carboxamide; 2-chloro-N-{(2-(2,6-dioxo(3-piperidyl))-1,3-dioxoisoindolin-4-yl)methyl}acetamide; N-(2-(2,6-dioxo(3-piperidyl))-1,3-dioxoisoindolin-4-yl)-3-pyridylcarboxamide; 3-{1-oxo-4-(benzylamino)isoindolin-2-yl}piperidine-2,6-dione; 2-(2,6-dioxo(3-piperidyl))-4-(benzylamino)isoindoline-1,3-dione; N-{(2-(2,6-dioxo(3-piperidyl))-1,3-dioxoisoindolin-4-yl)methyl}propanamide; N-{(2-(2,6-dioxo(3-piperidyl))-1,3-dioxoisoindolin-4-yl)methyl}-3-pyridylcarboxamide; N-{(2-(2,6-dioxo(3-piperidyl))-1,3-dioxoisoindolin-4-yl)methyl} heptanamide; N-{(2-(2,6-dioxo(3-piperidyl))-1,3-dioxoisoindolin-4-yl)methyl}-2-furylcarboxamide; {N-(2-(2,6-dioxo(3-piperidyl))-1,3-dioxoisoindolin-4-yl)carbamoyl}methyl acetate; N-(2-(2,6-dioxo(3-piperidyl))-1,3-dioxoisoindolin-4-yl)pentanamide; N-(2-(2,6-dioxo(3-piperidyl))-1,3-dioxoisoindolin-4-yl)-2-thienylcarboxamide; N-{[2-(2,6-dioxo(3-piperidyl))-1,3-dioxoisoindolin-4-yl]methyl} (butyl-amino)carboxamide; N-{[2-(2,6-dioxo(3-piperidyl))-1,3-dioxoisoindolin-4-yl]methyl} (octylamino)carboxamide; and N-{[2-(2,6-dioxo(3-piperidyl))-1,3-dioxoisoindolin-4-yl]methyl}(benzylamino)carboxamide.

In certain other embodiments, a patient in need thereof is administered one or more of the anti-BCMA antibodies provided herein in combination with one or more members of a class of isoindole-imides disclosed in U.S. Patent Application Publication No. US 2002/0045643, International Publication No. WO 98/54170, and U.S. Pat. No. 6,395,754, each of which is incorporated herein by reference. Representative compounds are of formula III:

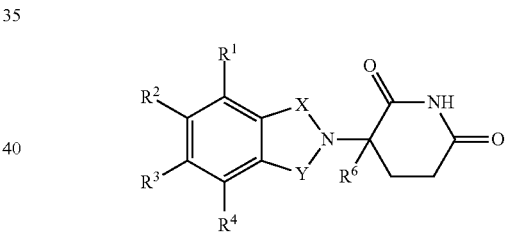

and pharmaceutically acceptable salts, hydrates, solvates, clathrates, enantiomers, diastereomers, racemates, and mixtures of stereoisomers thereof, wherein: one of X and Y is C=O and the other is CH₂ or C=O;

R is H or CH₂OCOR';

(i) each of R¹, R², R³, or R⁴, independently of the others, is halo, alkyl of 1 to 4 carbon atoms, or alkoxy of 1 to 4 carbon atoms or (ii) one of R¹, R², R³, or R⁴ is nitro or —NHR⁵ and the remaining of R¹, R², R³, or R⁴ are hydrogen; R⁵ is hydrogen or alkyl of 1 to 8 carbons R⁶ hydrogen, alkyl of 1 to 8 carbon atoms, benzo, chloro, or fluoro;

R' is R⁷—CHR¹⁰—N(R⁸R⁹);

R⁷ is m-phenylene or p-phenylene or —(CₙH₂ₙ)— in which n has a value of 0 to 4; each of R⁸ and R⁹ taken independently of the other is hydrogen or alkyl of 1 to 8 carbon atoms, or R⁸ and R⁹ taken together are tetramethylene, pentamethylene, hexamethylene, or —CH₂CH₂X₁CH₂CH₂— in which X₁ is —O—, —S—, or —NH—; R¹⁰ is hydrogen, alkyl of to 8 carbon atoms, or phenyl; and

* represents a chiral-carbon center.

Other representative compounds are of formula:

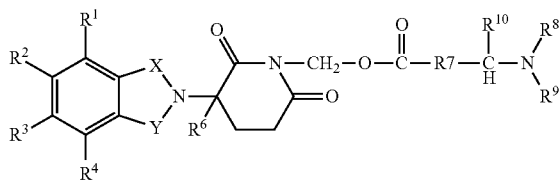

wherein: one of X and Y is C=O and the other of X and Y is C=O or CH$_2$;
(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen or alkyl of 1 to 8 carbon atoms;
R$^6$ is hydrogen, alkyl of 1 to 8 carbon atoms, benzo, chloro, or fluoro;
R$^7$ is m-phenylene or p-phenylene or —(C$_n$H$_{2n}$)— in which n has a value of 0 to 4;
each of R$^8$ and R$^9$ taken independently of the other is hydrogen or alkyl of 1 to 8 carbon atoms,
or R$^8$ and R$^9$ taken together are tetramethylene, pentamethylene, hexamethylene, or —CH$_2$CH$_2$X$_1$CH$_2$CH$_2$— in which X$_1$ is —O—, —S—, or —NH—; and
R$^{10}$ is hydrogen, alkyl of to 8 carbon atoms, or phenyl.

Other representative compounds are of formula:

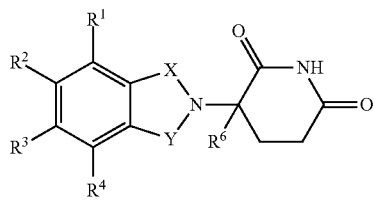

in which
one of X and Y is C=O and the other of X and Y is C=O or CH$_2$;
each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is nitro or protected amino and the remaining of R$^1$, R$^2$, R$^3$, and R$^4$ are hydrogen; and
R$^6$ is hydrogen, alkyl of 1 to 8 carbon atoms, benzo, chloro, or fluoro.

Other representative compounds are of formula:

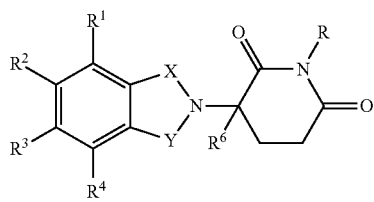

in which:
one of X and Y is C=O and the other of X and Y is C=O or CH$_2$;
(i) each of R$^1$, R$^2$, R$^3$, and R$^4$, independently of the others, is halo, alkyl of 1 to 4 carbon atoms, or alkoxy of 1 to 4 carbon atoms or (ii) one of R$^1$, R$^2$, R$^3$, and R$^4$ is —NHR$^5$ and the remaining of R$^1$, R$^2$, R$^3$, and R$^4$ are hydrogen;
R$^5$ is hydrogen, alkyl of 1 to 8 carbon atoms, or CO—R$^7$—CH(R$^{10}$)NR$^8$R$^9$ in which each of R$^7$, R$^8$, R$^9$, and R$^{10}$ is as herein defined; and
R$^6$ is alkyl of 1 to 8 carbon atoms, benzo, chloro, or fluoro.

Specific examples of the compounds are of formula

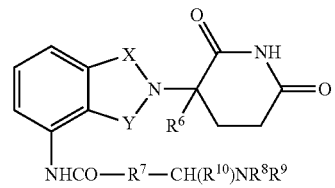

one of X and Y is C=O and the other of X and Y is C=O or CH$_2$;
R$^6$ is hydrogen, alkyl of 1 to 8 carbon atoms, benzyl, chloro, or fluoro;
R$^7$ is m-phenylene, p-phenylene or —(C$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$_1$CH$_2$CH$_2$— in which X$_1$ is —O—, —S— or —NH—; and
R$^{10}$ is hydrogen, alkyl of 1 to 8 carbon atoms, or phenyl.

Other specific immunomodulatory compounds are 1-oxo-2-(2,6-dioxo-3-fluoropiperidin-3 yl) isoindolines and 1,3-dioxo-2-(2,6-dioxo-3-fluoropiperidine-3-yl)isoindolines such as those described in U.S. Pat. Nos. 5,874,448 and 5,955,476, each of which is incorporated herein by reference. Representative compounds are of formula:

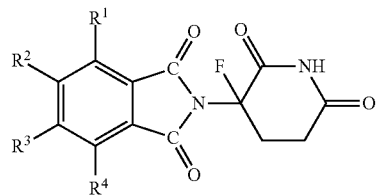

wherein: Y is oxygen or H2 and each of R$^1$, R$^2$, R$^3$, and R$^4$, independently of the others, is hydrogen, halo, alkyl of 1 to 4 carbon atoms, alkoxy of 1 to 4 carbon atoms, or amino.

Other specific immunomodulatory compounds disclosed herein are 1-oxo and 1,3-dioxoisoindolines substituted in the 4- or 5-position of the indoline ring described in U.S. Pat. Nos. 6,380,239 and 7,244,759, both of which are incorporated herein by reference. Representative compounds are of formula:

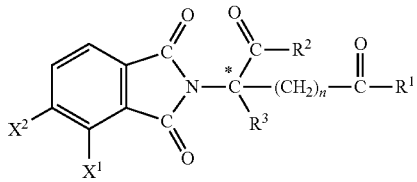

in which the carbon atom designated C* constitutes a center of chirality (when n is not zero and $R^1$ is not the same as $R^2$); one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is hydrogen, alkyl of one to six carbons, halo, or haloalkyl; Z is hydrogen, aryl, alkyl of one to six carbons, formyl, or acyl of one to six carbons; and n has a value of 0, 1, or 2; provided that if $X^1$ is amino, and n is 1 or 2, then $R^1$ and $R^2$ are not both hydroxy; and the salts thereof.

Further representative compounds are of formula:

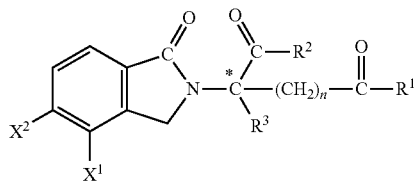

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl or an alkyl or acyl of one to six carbons; and n has a value of 0, 1, or 2.

Specific examples include, but are not limited to, 2-(4-amino-1-oxo-1,3-dihydro-isoindol-2-yl)-4-carbamoyl-butyric acid and 4-(4-amino-1-oxo-1,3-dihydro-isoindol-2-yl)-4-carbamoyl-butyric acid, which have the following structures, respectively, and pharmaceutically acceptable salts, solvates, prodrugs, and stereoisomers thereof:

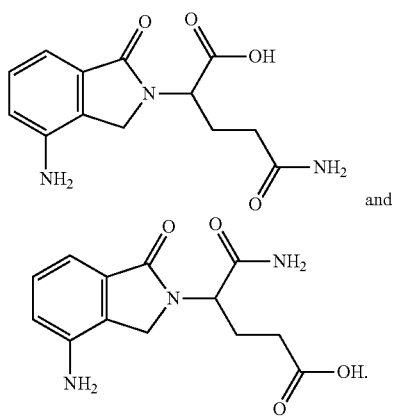

Other representative compounds are of formula:

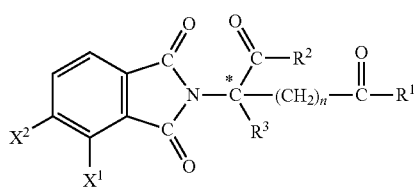

in which the carbon atom designated C* constitutes a center of chirality when n is not zero and $R^1$ is not $R^2$; one of $X^1$ and $X^2$ is amino, nitro, alkyl of one to six carbons, or NH—Z, and the other of $X^1$ or $X^2$ is hydrogen; each of $R^1$ and $R^2$ independent of the other, is hydroxy or NH—Z; $R^3$ is alkyl of one to six carbons, halo, or hydrogen; Z is hydrogen, aryl, or an alkyl or acyl of one to six carbons; and n has a value of 0, 1, or 2; and the salts thereof.

Specific examples include, but are not limited to, 4-carbamoyl-4-{4-[(furan-2-yl-methyl)-amino]-1,3-dioxo-1,3-dihydro-isoind-ol-2-yl}-butyric acid, 4-carbamoyl-2-{4-[(furan-2-yl-methyl)-amino]-1,3-dioxo-1,3-dihydro-isoindol-2-yl}-butyric acid, 2-{4-[(furan-2-yl-methyl)-amino]-1,3-dioxo-1,3-dihydro-isoindol-2-yl}-4-phenylcarbamoyl-butyric acid, and 2-{4-[(furan-2-yl-methyl)-amino]-1,3-dioxo-1,3-dihydro-isoindol-2-yl}-pentanedioic acid, which have the following structures, respectively, and pharmaceutically acceptable salts, solvate, prodrugs, and stereoisomers thereof:

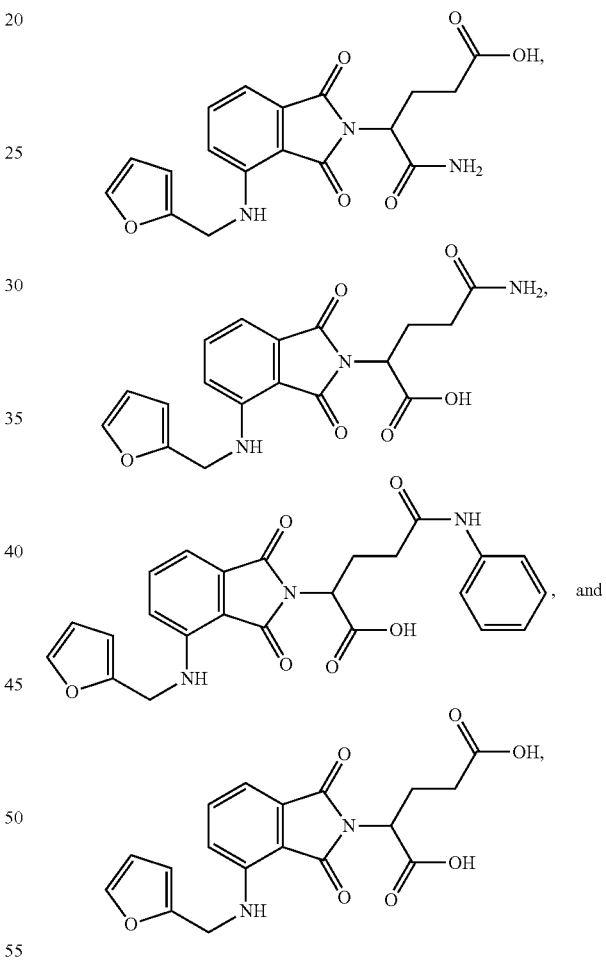

Other specific examples of the compounds are of formula:

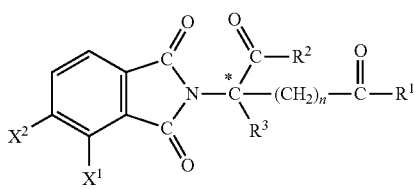

wherein:
one of $X^1$ and $X^2$ is nitro, or NH—Z, and the other of $X^1$ or $X^2$ is hydrogen;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Other representative compounds are of formula:

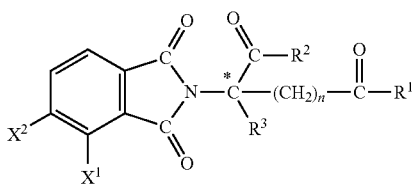

wherein:
one of $X^1$ and $X^2$ is alkyl of one to six carbons;
each of $R^1$ and $R^2$, independent of the other, is hydroxy or NH—Z;
$R^3$ is alkyl of one to six carbons, halo, or hydrogen;
Z is hydrogen, phenyl, an acyl of one to six carbons, or an alkyl of one to six carbons; and
n has a value of 0, 1, or 2; and
if —$COR^2$ and —$(CH_2)_nCOR^1$ are different, the carbon atom designated C* constitutes a center of chirality.

Still other specific immunomodulatory compounds are isoindoline-1-one and isoindoline-1,3-dione substituted in the 2-position with 2,6-dioxo-3-hydroxypiperidin-5-yl described in U.S. Pat. No. 6,458,810, which is incorporated herein by reference.

Representative compounds are of formula:

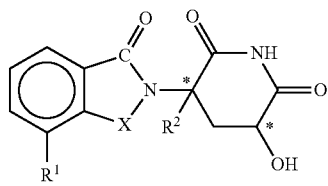

wherein:
the carbon atoms designated * constitute centers of chirality;
X is —C(O)— or —$CH_2$—;
$R^1$ is alkyl of 1 to 8 carbon atoms or —$NHR^3$;
$R^2$ is hydrogen, alkyl of 1 to 8 carbon atoms, or halogen; and
$R^3$ is hydrogen,
alkyl of 1 to 8 carbon atoms, unsubstituted or substituted with alkoxy of 1 to 8 carbon atoms,
halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms,
benzyl, unsubstituted or substituted with alkyl of 1 to 8 carbon atoms, alkoxy of 1 to 8 carbon atoms, halo, amino, or alkylamino of 1 to 4 carbon atoms, or —$COR^4$ in which $R^4$ is hydrogen,
alkyl of 1 to 8 carbon atoms, unsubstituted or substituted with alkoxy of 1 to 8 carbon atoms, halo, amino, or alkylamino of 1 to 4 carbon atoms,
cycloalkyl of 3 to 18 carbon atoms,
phenyl, unsubstituted or substituted with alkyl of 1 to 8 carbon atoms, alkoxy of 1 to 8 carbon atoms, halo, amino, or alkylamino of 1 to 4 carbon atoms, or
benzyl, unsubstituted or substituted with alkyl of 1 to 8 carbon atoms, alkoxy of 1 to 8 carbon atoms, halo, amino, or alkylamino of 1 to 4 carbon atoms.

7. EXAMPLES

The following materials and methods were employed in the experiments described in Examples 1-3.

Cell Culturing: Hek293 cells were grown in DMEM (ThermoFisher) supplemented with 10% fetal bovine serum (FBS). C6 cells were maintained Ham's F12 Nutrient Mixture (ThermoFisher) supplemented with 10% FBS. NCIH929, U266B1, KMS12BM, OPM2 and NUDHL1 cells were cultivated in RPMI-1640 medium supplemented with 10% FBS.

Plasmids: cDNA encoding full-length human BCMA (UniProtKB-Q02223; TNFRSF17) was cloned into the expression vector SF #10008 and transfected into C6 cells. The full-length cDNA encoding human TNFRSF12A (TWEAKR; NP_057723.1) was subcloned into pCDNA3.1 (+) expression vector that was subsequently transfected into Hek293 cells. Transfectants were selected using puromycin or neomycin and clonal populations generated and screened by flow cytometry.

FACS Analysis: FACs antibodies used in this study include: 1) LS-C106982-100 Mouse Monoclonal to Human TNFRSF12A-R-Phycoerythrin (PE) (LifeSpan BioSciences, Inc.); 2) EM901 has been previously characterized as a BCMA-binding antibody (Mab42; International Application Number WO2017/021450); 3) Ebiosciences anti-human IgG Fcγ-specific, labeled with PE; 4) Human IgG isotype control; 5) Anti-TACI antibody [1A1] (Abcam); 6) BAFF Receptor antibody 8A7 (ThermoFisher); 7) BCMA antibody 19F2 (BioLegend). Each cell type (75,000 cells/well) was incubated with primary antibodies in FACs buffer (PBS containing 0.2% BSA) for 25 min in a 96 well plate. Cells were washed once with FACs buffer and incubated with 1:100 dilution secondary antibody for 25 min. After washing once, cells were fixed for 10 min with 1% paraformaldehyde, washed with FACs buffer and resuspended in 100 μL FACs buffer. Labeled cells were analyzed using an Attune NxT Flow Cytometer and data processed using FlowJo 10.0.8r1 (FLOWJO LLC), according to the manufacturer's instructions.

7.1. Example 1

B-cell maturation antigen (BCMA), also known as tumor necrosis factor receptor superfamily member 17 (TNFRSF17), is a protein that is indicated in many different types of cancer.

Anti-BCMA antibody generation: Antibodies against human BCMA were derived from immunizations in Omni-Flic (Ligand Pharmaceuticals)×RAT5Lew animals performed at Aldevron Freiburg (Freiburg, Germany) with multiple applications of a DNA vector comprising of BCMA-(a.a.1-54) and recombinant human BCMA extracellular domain protein (aa. 1-54) purchased from AcroBiosystem (Newark, Del. 19711). Lymph nodes from immunoreactive animals were harvested and total RNA extracted from primary lymphocytes at Teneobio, Inc. (Palo Alto, Calif.). The IgG variable regions were amplified in each sample before paired-end next generation sequencing was performed, followed by rank analysis to quantitate expression level for each unique human IgG variable region. Highly expressed IgG sequence lineages were selected for cloning into the pTT5 expression vectors (NRC Toronto, Ontario, Canada) for protein expression.

Expression of anti-BCMA antibodies: The previously described five $V_H$ regions, along with a panel of putative BCMA reactive $V_H$'s, were each cotransfected with a single common $V_L$ in in a standard IgG1/Kappa antibody format. All antibody sequences were subcloned into the pTT5 mammalian protein expression vector (NRC-CNRC, Ottawa, Ontario, Canada). The antibodies were transiently transfected into Expi293 or ExpiCHO-S cells (Thermo Fisher Scientific, Waltham, Mass.) in 24 deep well plates (Cat. #P-DW-10ML-24-C-S, Axygen, Tewksbury, Mass.) according to manufacturer's protocols. For each antibody, a DNA ratio of 1:1 LC:HC was used for expression at 0.5 µg/mL DNA/mL expression media, and cultures were shaken at 500 RPM using a 3 mM orbit shaking platform at 37° C. with a 5% $CO_2$ atmosphere. After six to seven days of transfection, the plates were clarified by centrifugation (3724 RCF, 4° C., 30 minutes) and the supernatants were transferred to new multi-well plates, assessed for titer using protein A biosensors on the Octet Red 384 (Pall ForteBio, Freemont, Calif.) and screened for activity.

Upon identification of hits, the anti-BCMA lead molecules were transiently transfected in ExpiCHO-S cells at a 60 mL scale in Erlenmeyer 250 mL flasks (Cat #:431144, Corning, Tewksbury, Mass.) per manufacturer instructions, and agitated at 37° C. at 120 RPM on a shaking platform with a 25 mM orbit. After one week of culture, supernatants were harvested by centrifugation (3724 RCF, 4° C., 30 minutes) followed by filtration (Cat. #89220-720, VWR, Radnor, Pa.), and subsequently purified.

Purification of anti-BCMA antibodies: Filtered supernatants were purified using 5 mL Mab Select Sure Lx resin (Cat #29157185, GE healthcare) on an AKTA Pure chromatography system (Cat #29046694, GE Healthcare). These samples were eluted off the column using Sodium Citrate, pH 3.0 and neutralized to pH 5.5 with 3M Tris-HCl. The final samples were dialyzed into our universal buffer (10 mM Sodium Acetate pH 5.2 and 9% (w/v) Sucrose). The concentration and purity (assessment of aggregation) were measured by utilizing an SEC column (Cat #PL 1580-3301, Agilent USA).

Surface plasmon resonance binding assays for anti-BCMA antibodies: Running buffer used in this assay was HBS-EP (150 mM NaCl, 10 mM Hepes pH7.4, 3 mM EDTA and 0.005% Surfactant P20). For non-avidity measurements, antibodies 320199 and 319883 were captured on a protein A chip (GE Healthcare) at a concentration of 2 µg/mL, while recombinant Hu-BCMA from Acro Biosystems (BCA-H522y) as well as Fc-cleaved Cyno-BCMA were flowed over starting at a top concentration of 50 nM with subsequent 3 fold dilutions to 0.6 nM (50 nM, 16.66 nM, 5.55 nM, 1.85 nM, 0.6 nM and 0 nM). Assays were performed at 25° C. and 37° C. with a flow rate of 10 µL.

Figure 1A:
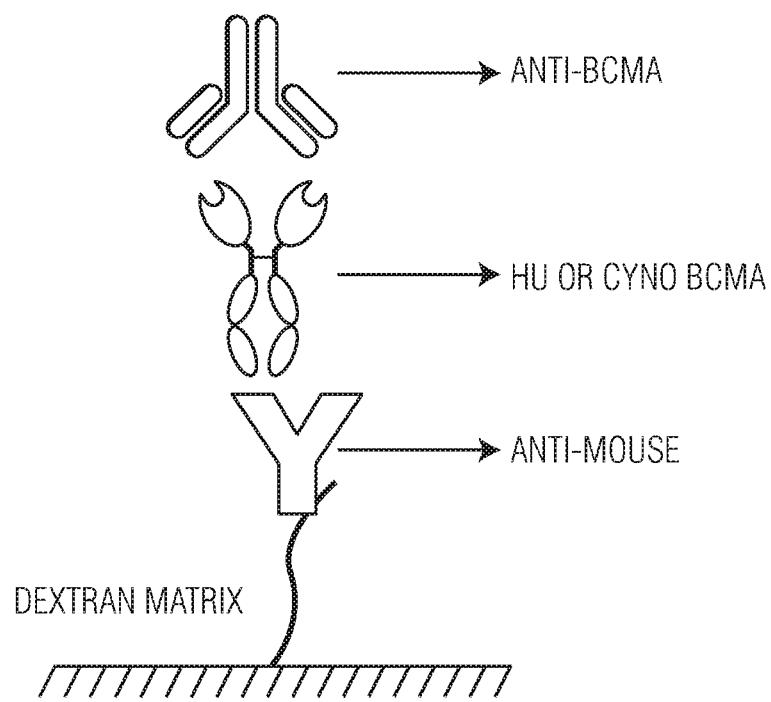
FIGS. 1A-1B are schematic illustrations of avidity (FIG. 1A) and non-avidity (FIG. 1B) binding.
Figure 1B:
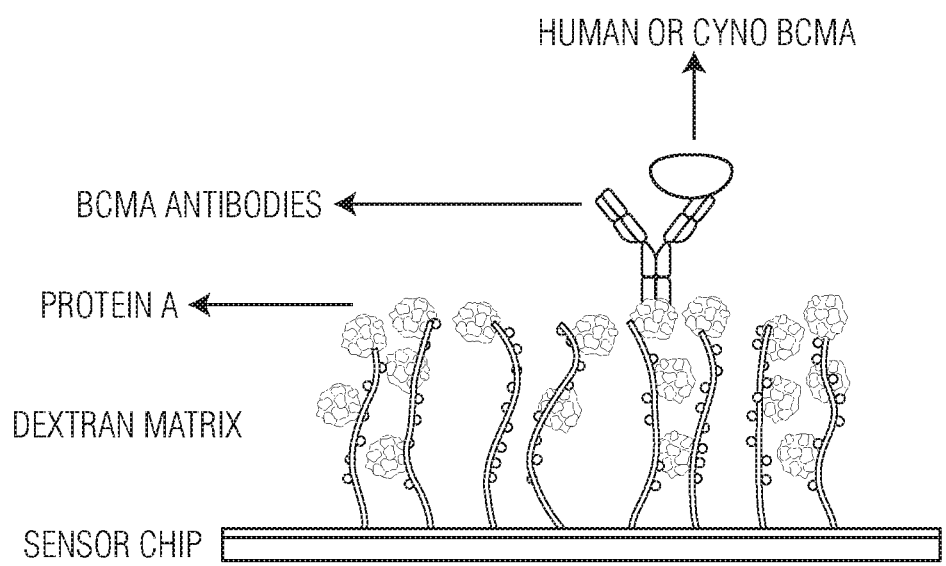
Figure 3F:
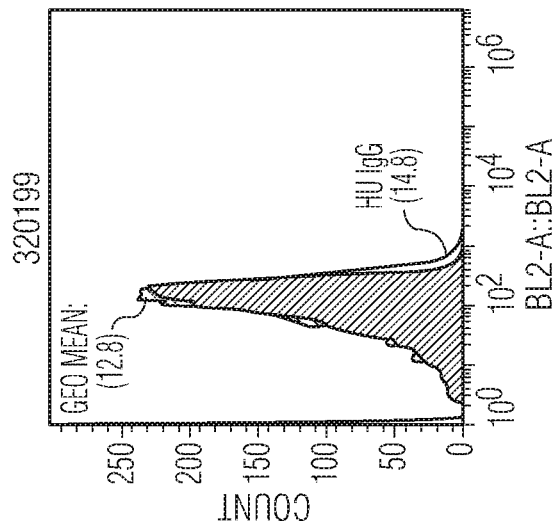
Figure 3E:
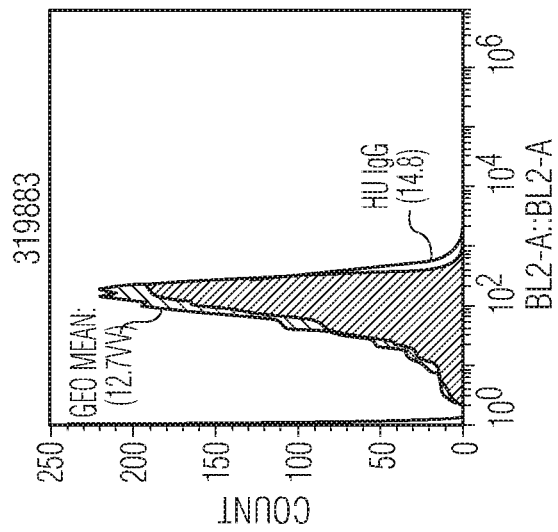
Figure 3D:
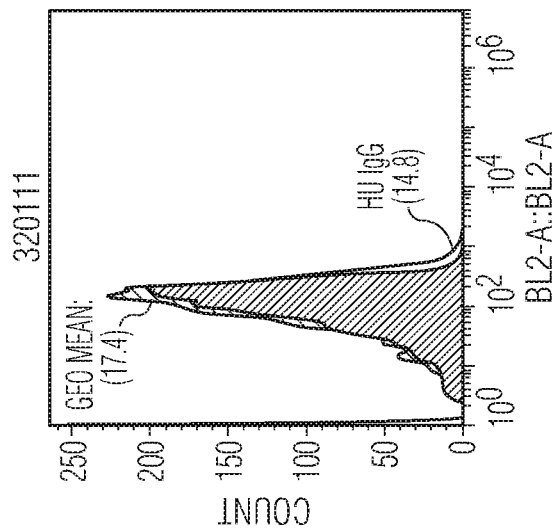
Figure 4A:
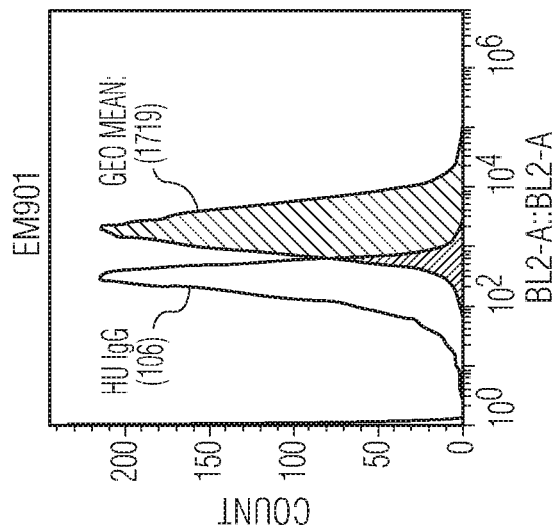
Figure 4B:
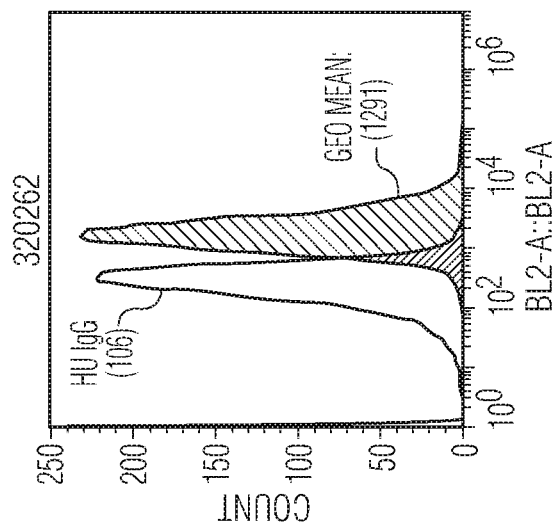
Figure 4C:
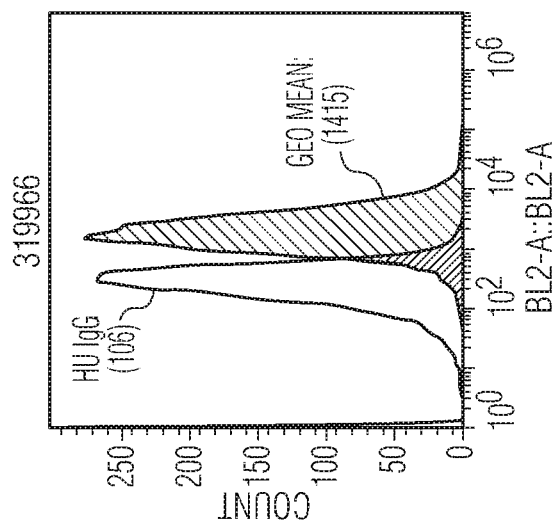
Figure 4F:
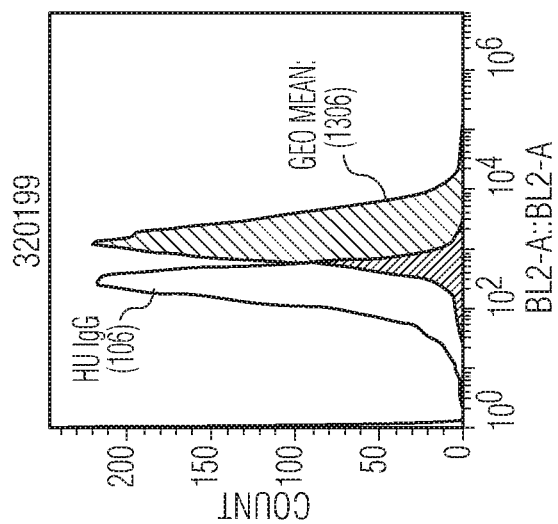
Figure 4E:
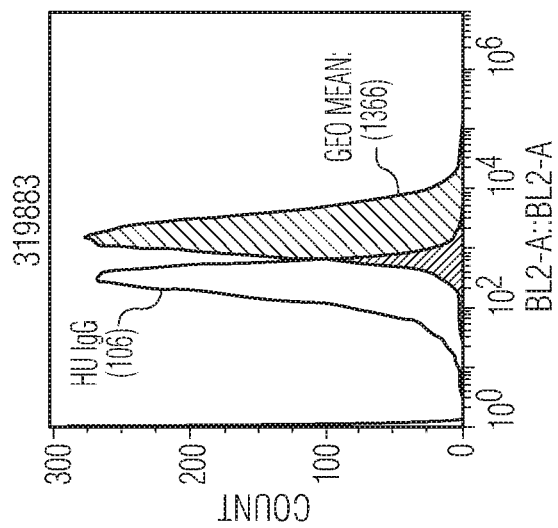
Figure 4D:
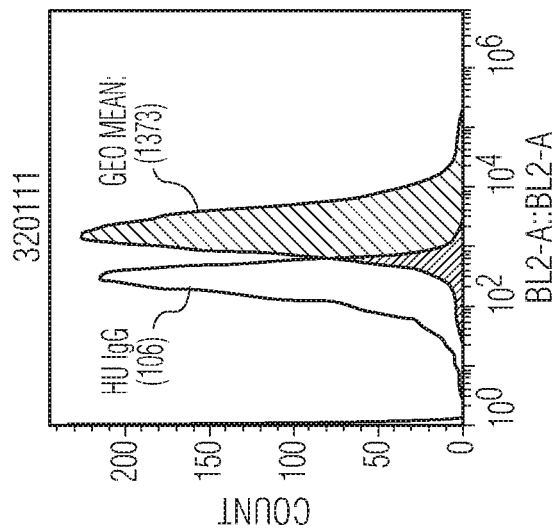

Six BCMA clones from Teniobio (320199, 319883, 319952, 320262, 319966, 320111) were tested for binding to Human-BCMA, Cyno-BCMA and Cyno-TACI (Transmembrane Activator and CAML Interactor) expressed in 293 cells with a Murine Fc tag using a Biacore-8K instrument (GE Healthcare). Avidity (Figure. 1A) and non-avidity (Figure. 1B) measurements were tested.

For avidity measurements, antigens were captured on an anti-mouse surface at a concentration of 2 µg/mL, while antibodies were flowed over with a starting top concentration of 50 nM followed by subsequent 3-fold dilutions to 0.6 nM (50 nM, 16.66 nM, 5.55 nM, 1.85 nM, 0.6 nM and 0 nM). Assays were performed at 25° C. with a flow rate of 10 µL/min for capture, 30 µL/min for 3 minutes of association and 5 minutes of dissociation. The surface was regenerated after each minute for capture followed by 30 µL/min for 3 minutes of association and 5 minutes of dissociation. The surface was regenerated after each cycle with 10 mM Glycine pH 1.5 for 1 minute. The running buffer used in this assay was HBS-EP (150 mM NaCl, 10 mM Hepes pH7.4, 3 mM EDTA and 0.005% Surfactant P20).

Data analysis was done utilizing the Biacore 8K Analysis software (GE Healthcare) by looking at double referenced data and using the 1:1 Langmuir model for fits. An anti-BCMA antibody from EngMab was used as a positive control, while an anti-RSV1-IgG1 was used as a negative control.

Immunohistochemistry: DAB single color immunohistochemistry (IHC) staining of binders in either human or rabbit IgG backbone with normal human and rabbit (Abcam, ab172730) IgG as isotype controls, was performed on the Bond-III Autostainer (Leica Microsystems) with Bond polymer refine detection kit (Leica, DS9800). Formalin-fixed, paraffin-embedded (FFPE) sections (4 µm) of cell pellets were antigen-unmasked with epitope retrieval solution 1 (Leica, AR9961) for 20 minutes at 100° C., and blocked with peroxide blocking agent for 5 minutes. Sections were incubated with binders at appropriate dilutions for 15 minutes. For binders in human IgG backbone, a secondary rabbit anti human IgG antibody (Abcam, ab2410, 1:100) was applied for 8 minutes. This step was not needed for binders in rabbit IgG backbone. Sections were then incubated in polymer for 8 minutes, developed in DAB for 10 minutes, counterstained with hematoxylin for 5 minutes, coverslipped with Sakura Finetek.

7.2. BCMA Antibody Binding Studies. Example 2

This example demonstrates that the human IgGs, 320262, 319966, 320111, 319883 and 320199 recognize C6 cells expressing the human BCMA protein. C6 cells stably-transfected with human BCMA or mock-transfected C6 cells were incubated with 0.4 µg/ml of EM901, 320262, 319966, 320111, 319883 or 320199. The reactivity of each antibody was monitored by FACs. EM901, an antibody that previously has been demonstrated to detect BCMA (patent number WO2017021450), robustly bound C6-BCMA transfectants, confirming BCMA expression by these cells. Relative to non-transfected C6 cells (left histogram (blue) curve in each frame), histograms corresponding with 320262, 319966, 320111, 319883 and 320199 (right histogram (red) curve in each frame) exhibited substantial rightward shifts (FIGS. 2B-2F). These results indicate that 320262, 319966, 320111, 319883 and 320199 react with cell surface-expressed human BCMA. Geometric mean values quantifying these binding interactions are included (FIGS. 2A-2F).

7.3. BCMA Antibody Binding Studies. Example 3

This example shows that 320262, 319966, 320111, 319883 and 320199 do not bind Hek293 cells expressing full-length human TNFRSF12A/TWEAKR, a member of the TNF receptor family that is related to BCMA. Hek293 cells stably transfected with human TNFRSF12A were incubated with 0.4 ug/ml of human IgG isotype control, 320262, 319966, 320111, 319883 or 320199. The reactivity of each antibody was monitored by FACs. An anti-TNFRSF12A antibody stained Hek293-TNFRSF12A cells, indicative of TNFRSF12A expression. Relative to isotype control (blue histogram), rightward shifts of histograms corresponding with 320262, 319966, 320111, 319883 and 320199 (shown in red) could not be detected (FIGS. 3B-3F). These results indicate that 320262, 319966, 320111, 319883 and 320199 did not exhibit significant binding activity toward human TNFRSF12A. Geometric means quantifying these binding interactions are shown (FIGS. 3A-3F). 7.4. BCMA Antibody Binding Studies. Example 4

This example demonstrates that 320262, 319966, 320111, 319883 and 320199 recognize NCIH929 multiple myeloma cells, that endogenously-express human BCMA. NCIH929 cells were incubated with 1.0 ug/ml of human IgG isotype control, EM901, 320262, 319966, 320111, 319883 or 320199. The reactivity of each mAb was monitored by FACs. The EM901 antibody, that recognizes BCMA, robustly bound NCIH929 cells. Relative to isotype control (left histogram (blue) curve in each frame), histograms corresponding with 320262, 319966, 320111, 319883 and 320199 (right histogram (red) curve in each frame) exhibited substantial rightward shifts (FIGS. 4B-4F). These results indicate that 320262, 319966, 320111, 319883 and 320199 reacted with NCIH929 cells. Geometric means quantifying these binding interactions are shown (FIGS. 4A-4F).

7.5 BCMA Antibody Binding Studies. Example 5

This example demonstrates that 320262, 319966, 320111, 319883 and 320199 recognize BCMA multiple myeloma cells, U266B1 and KMS12BM incubated with 0.016-10 ug/ml of human IgG isotype control, EM901, 320262, 319966, 320111, 319883 or 320199, as indicated in FIGS. 5A-5B. The reactivity of each mAb was monitored by FACs. EM901, 320262, 319966, 320111, 319883 and 320199 bound U266B1 and KMS12BM relative to isotype control in a dose-responsive fashion (FIGS. 5A-5B). Additionally, 320262 and 320111 recognized OPM2 multiple myeloma cells that express BCMA, but not TACI or BAFF receptor, other TNF receptor family members related to BCMA (dose-response curve and bar graph, FIGS. 5C-5D). In contrast, 320262 and 320111 did not bind NUDHL1 cells that are BCMA$^-$/TACI$^+$/BAFFR$^+$ (dose-response curve and bar graph, FIGS. 5E-5F). These results indicate that 320262, 319966, 320111, 319883 and 320199 exhibit BCMA-dependent, dose-responsive cell-binding. Geometric means quantifying these binding interactions are shown (FIGS. 5A-5F).

| SEQ ID NO. | ITEM | SEQUENCE |
|---|---|---|
| 1 | Common Light Chain VL | EIVMTQSPATLSVSPGERATLSCRASQSVSSNLAWYQQKPGQAPRLLIYGASTRATGIPARFSGSG SGTEFTLTISSLQSEDFAVYYCQQYNNWPWTFGQGTKVEIK |
| 2 | cLC CDR1 (Kabat, Chothia, IMGT) | RASQSVSSNLA |
| 3 | cLC CDR2 (Kabat, Chothia, IMGT) | GASTRAT |
| 4 | cLC CDR3 (Kabat, Chothia, IMGT) | QQYNNWPWT |
| 5 | cLC | GAAATTGTGATGACTCAGTCGCCCGCCACCCTGTCCGTGTCTCCGGGAGAGCGGGCCACTCTGAGC TGTCGCGCGTCACAGTCGGTGTCCTCCAACCTCGCCTGGTACCAGCAGAAGCCTGGACAGGCCCCA AGACTGCTGATCTACGGCGCCTCCACCCGGGCCACCGGGATTCCTGCCCGGTTCTCCGGCTCCGGT TCCGGCACTGAGTTCACCCTGACCATCAGCTCACTGCAGTCCGAGGACTTCGCCGTGTACTACTGC CAGCAGTACAACAACTGGCCGTGGACCTTTGGCCAAGGAACCAAGGTCGAAATCAAG |
| 6 | 320111 VH | QLPLQESGPGLVKPSETLSLTCTVSGGSIRSSSYYWGWIRQPPGKGLEWIGTIYYSGSTYYNPSLK SRVTISVDTSKNQLSLKLSSVTAADTAVYYCARPYYDSSGYYYYWGQGTLVTVSS |
| 7 | 320111 VH CDR1 Kabat | SSSYYWG |
| 8 | 320111 VH CDR2 Kabat | TIYYSGTYYNPSLKS |
| 9 | 320111 VH CDR3 Kabat | PYYDSSGYYYY |
| 10 | 320111 VH CDR1 Chothia | GGSIRSSSY |
| 11 | 320111 VH CDR2 Chothia | YYSGS |

| SEQ ID NO. | ITEM | SEQUENCE |
|---|---|---|
| 12 | 320111 VH CDR3 Chothia | PYYDSSGYYYY |
| 13 | 320111 VH CDR1 IMGT | GGSIRSSSYYWG |
| 14 | 320111 VH CDR2 IMGT | TIYYSGSTYYNPSLKS |
| 15 | 320111 VH CDR3 IMGT | PYYDSSGYYYY |
| 16 | 320111 VH | CAGCTGCCGCTGCAGGAGTCGGGCCCAGGACTGGTGAAGCCTTCGGAGACCCTGTCCCTCACCTGC ACTGTTTCTGGTGGCTCCATCAGGAGTAGTAGTTACTACTGGGGCTGGATCCGGCAGCCCCCAGGG AAGGGGCTGGAGTGGATTGGGACTATCTATTATAGTGGGAGCACCTACTACAACCCGTCCCTCAAG AGTCGAGTCACCATATCCGTAGACACGTCCAAGAACCAGCTCTCCCTGAAGCTGAGCTCTGTGACC GCCGCAGACACGGCTGTGTATTACTGTGCGAGACCTTACTATGATAGTAGTGGTTATTACTACTAC TGGGGCCAGGGCACCCTGGTCACCGTCTCCTCA |
| 17 | 320199 VH | QLQLQESGPGLVKPSETLSLTCTVSGGSISSSNSYWGWIRQSPGRGLEWIGRIYYSGITHYNPSLK SRVTISVDTSKNQFSLKLSSVTAADTAVYYCASPYKWNDGNFFGWGQGTLVTVSS |
| 18 | 320199 VH CDR1 Kabat | SSNSYWG |
| 19 | 320199 VH CDR2 Kabat | RIYYSGITHYNPSLKS |
| 20 | 320199 VH CDR3 Kabat | PYKWNDGNFFG |
| 21 | 320199 VH CDR1 Chothia | GGSISSSNS |
| 22 | 320199 VH CDR2 Chothia | YYSGI |
| 23 | 320199 VH CDR3 Chothia | PYKWNDGNFFG |
| 24 | 320199 VH CDR1 IMGT | GGSISSSNSYWG |
| 25 | 320199 VH CDR2 IMGT | RIYYSGITHYNPSLKS |
| 26 | 320199 VH CDR3 IMGT | PYKWNDGNFFG |
| 27 | 320199 VH | CAGCTGCAGCTGCAGGAGTCGGGCCCAGGACTGGTGAAGCCTTCGGAGACCCTGTCCCTCACCTGC ACTGTCTCTGGTGGCTCCATCAGCAGTAGTAATTCCTACTGGGGCTGGATCCGCCAGTCCCCAGGG AGGGGGCTGGAGTGGATTGGGAGGATCTATTATAGTGGATCACCCACTACAACCCGTCCCTCAAG AGTCGAGTCACCATATCCGTAGACACGTCCAAGAACCAGTTCTCCCTGAAGCTGAGCTCTGTGACC GCCGCAGACACGGCTGTGTATTACTGTGCGAGTCCGTATAAGTGGAACGACGGGAATTTTTTTGGT TGGGGCCAGGGCACCCTGGTCACCGTCTCCTCA |
| 28 | 320262 VH | QLQLQESGPGLVKPSETLSLTCTVSGGSISNYYWGWIRQPPGKGLEWIGNIYYSGRTYYTPSLK SRVTISEDTSKNQFSLKVRSVTVADTGVYYCARPDYYGSGTIAWGQGTLVTVSS |
| 29 | 320262 VH CDR1 Kabat | NSNYYWG |
| 30 | 320262 VH CDR2 Kabat | NIYYSGRTYYTPSLKS |
| 31 | 320262 VH CDR3 Kabat | PDYYGSGTIA |
| 32 | 320262 VH CDR1 Chothia | GGSISNSY |

-continued

| SEQ ID NO. | ITEM | SEQUENCE |
|---|---|---|
| 33 | 320262 VH CDR2 Chothia | YYSGR |
| 34 | 320262 VH CDR3 Chothia | PDYYGSGTIA |
| 35 | 320262 VH CDR1 IMGT | GGSISNSNYYWG |
| 36 | 320262 VH CDR2 IMGT | NIYYSGRTYYTPSLKS |
| 37 | 320262 VH CDR3 IMGT | PDYYGSGTIA |
| 38 | 320262 VH | CAGCTGCAGCTACAGGAGTCGGGCCCAGGACTGGTGAAGCCTTCGGAGACCCTGTCCCTCACCTGC<br>ACTGTCTCTGGTGGCTCCATCAGCAATAGTAATTATTACTGGGGCTGGATCCGCCAGCCCCCAGGA<br>AAGGGGCTGGAGTGGATTGGGAATATCTATTATAGTGGGAGAACCTATTACACCCCGTCCCTCAAG<br>AGTCGCGTCACCATATCCGAAGCACGTCCAAGAACCAGTTCTCCCTGAAGGTGAGGTCTGTGACC<br>GTCGCAGACACGGGTGTGTATTACTGTGCGAGACCGGATTACTATGGTTCGGGGACTATCGCGTGG<br>GGCCAGGGCACCCTGGTCACCGTCTCCTCA |
| 39 | 319883 VH | QLQLQESGPGLVKPSDTLSLTCTVSGGSISSSNSYWGWIRQSPGRGLEWIGRIYYSGITHYNPSLK<br>SRVTISVDTSKNQFSLKLSSVTAADTAVYYCASPYKWNDGNFFGWGQGTLVTVSS |
| 40 | 319883 VH CDR1 Kabat | SSNSYWG |
| 41 | 319883 VH CDR2 Kabat | RIYYSGITHYNPSLKS |
| 42 | 319883 VH CDR3 Kabat | PYKWNDGNFFG |
| 43 | 319883 VH CDR1 Chothia | GGSISSSNSY |
| 44 | 319883 VH CDR2 Chothia | YYSGI |
| 45 | 319883 VH CDR3 Chothia | PYKWNDGNFFG |
| 46 | 319883 VH CDR1 IMGT | GGSISSSNSYWG |
| 47 | 319883 VH CDR2 IMGT | RIYYSGITHYNPSLKS |
| 48 | 319883 VH CDR3 IMGT | PYKWNDGNFFG |
| 49 | 319883 VH | CAGCTGCAGCTGCAGGAGTCGGGCCCAGGACTGGTGAAGCCTTCGGACACCCTGTCCCTCACCTGC<br>ACTGTCTCTGGTGGCTCCATCAGCAGTAGTAATTCCTACTGGGGCTGGATCCGCCAGTCCCCAGGG<br>AGGGGGCTGGAGTGGATTGGGAGGATCTATTATAGTGGGATCACCCACTACAACCCGTCCCTCAAG<br>AGTCGAGTCACCATATCCGTAGACACGTCCAAGAACCAGTTCTCCCTGAAGCTGAGCTCTGTGACT<br>GCCGCGGACACGGCTGTGTATTACTGTGCGAGTCCGTATAAGTGGAACGACGGGAATTTTTTTGGT<br>TGGGGCCAGGGCACCCTGGTCACCGTCTCCTCA |
| 50 | 319966 VH | QLQLQESGPGLVKPSETLSLTCTVSGSSISRSNYYWGWIRQPPGKGLEWIGTFYYSGTTYYNPSLK<br>SRVTISEDTSKKQLSLNLRSVTAADTAVYYCARPSGYTTSWGQGTLVTVSS |
| 51 | 319966 VH CDR1 Kabat | RSNYYWG |
| 52 | 319966 VH CDR2 Kabat | TFYYSGTTYYNPSLKS |
| 53 | 319966 VH CDR3 Kabat | PSGYTTS |

| SEQ ID NO. | ITEM | SEQUENCE |
|---|---|---|
| 54 | 319966 VH CDR1 Chothia | GSSISRSNY |
| 55 | 319966 VH CDR2 Chothia | YYSGT |
| 56 | 319966 VH CDR3 Chothi a | PSGYTTS |
| 57 | 319966 VH CDR1 IMGT | GSSISRSNYYWG |
| 58 | 319966 VH CDR2 IMGT | TFYYSGTTYYNPSLKS |
| 59 | 319966 VH CDR3 IMGT | PSGYTTS |
| 60 | 319966 VH | CAGCTGCAGCTGCAGGAGTCGGGCCCAGGACTGGTGAAGCCTTCGGAGACCCTGTCCCTCACCTGC ACTGTCTCTGGAAGCTCCATCAGCAGGAGTAATTACTACTGGGGCTGGATCCGCCAGCCCCCAGGG AAGGGTCTGGAGTGGATTGGGACTTTCTATTATAGTGGGACCACCTACTACAACCCGTCCCTCAAG AGTCGAGTCACCATATCCGAAGACACGTCCAAGAAACAGTTATCCCTGAACCTGAGGTCTGTGACC GCCGCAGACACGGCTGTGTATTACTGTGCGAGACCTTCCGGATATACCACCAGCTGGGGCCAGGGC ACCCTGGTCACCGTCTCCTCA |

What is claimed is:

1. An antibody that binds to B-Cell Maturation Antigen (BCMA), or a BCMA-binding fragment thereof, comprising:
   (A) heavy chain CDR1, CDR2 and CDR3 sequences:
   a. SEQ ID NO: 7, SEQ ID NO: 8 and SEQ ID NO: 9, respectively;
   b. SEQ ID NO: 10, SEQ ID NO: 11 and SEQ ID NO: 12, respectively;
   c. SEQ ID NO: 13, SEQ ID NO: 14 and SEQ ID NO: 15, respectively;
   d. SEQ ID NO: 18, SEQ ID NO: 19 and SEQ ID NO: 20, respectively;
   e. SEQ ID NO: 21, SEQ ID NO: 22 and SEQ ID NO: 23, respectively;
   f. SEQ ID NO: 24, SEQ ID NO: 25 and SEQ ID NO: 26, respectively;
   g. SEQ ID NO: 29, SEQ ID NO: 30 and SEQ ID NO: 31, respectively;
   h. SEQ ID NO: 32, SEQ ID NO: 33 and SEQ ID NO: 34, respectively;
   i. SEQ ID NO: 35, SEQ ID NO: 36 and SEQ ID NO: 37, respectively;
   j. SEQ ID NO: 40, SEQ ID NO: 41 and SEQ ID NO: 42, respectively;
   k. SEQ ID NO: 43, SEQ ID NO: 44 and SEQ ID NO: 45, respectively;
   l. SEQ ID NO: 46, SEQ ID NO: 47 and SEQ ID NO: 48, respectively;
   m. SEQ ID NO: 51, SEQ ID NO: 52 and SEQ ID NO: 53, respectively;
   n. SEQ ID NO: 54, SEQ ID NO: 55 and SEQ ID NO: 56, respectively; or
   o. SEQ ID NO: 57, SEQ ID NO: 58 and SEQ ID NO: 59, respectively; and
   (B) light chain CDR1, CDR2 or CDR3 sequences SEQ ID NO: 2, SEQ ID NO: 3 and SEQ ID NO:4, respectively.

2. The antibody or BCMA-binding fragment of claim 1 which comprises light chain CDR1, CDR2 and CDR3 sequences SEQ ID NO:2, SEQ ID NO:3 and SEQ ID NO:4, respectively.

3. An antibody or a BCMA-binding fragment according to claim 1 comprising a light chain comprising CDR1, CDR2 and CDR3 sequences SEQ ID NO:2, SEQ ID NO:3 and SEQ ID NO:4, respectively, and heavy chain CDR1, CDR2 and CDR3 sequences:
   a. SEQ ID NO:7, SEQ ID NO:8, and SEQ ID NO:9, respectively;
   b. SEQ ID NO:10, SEQ ID NO:11, and SEQ ID NO:12, respectively; or
   c. SEQ ID NO:13, SEQ ID NO:14 and SEQ ID NO:15, respectively.

4. An antibody or BCMA-binding fragment according to claim 1 comprising a light chain comprising CDR1, CDR2 and CDR3 sequences SEQ ID NO:2, SEQ ID NO:3 and SEQ ID NO:4, respectively, and heavy chain CDR1, CDR2 and CDR3 sequences:
   a. SEQ ID NO:18, SEQ ID NO:19 and SEQ ID NO:20, respectively;
   b. SEQ ID NO:21, SEQ ID NO:22 and SEQ ID NO:23, respectively; or
   c. SEQ ID NO:24, SEQ ID NO:25 and SEQ ID NO:26, respectively.

5. An antibody or BCMA-binding fragment according to claim 1 comprising a light chain comprising CDR1, CDR2 and CDR3 sequences SEQ ID NO:2, SEQ ID NO:3 and SEQ ID NO:4, respectively, and heavy chain CDR1, CDR2 and CDR3 sequences:
   a. SEQ ID NO:29, SEQ ID NO:30 and SEQ ID NO:31, respectively;
   b. SEQ ID NO:32, SEQ ID NO:33 and SEQ ID NO:34, respectively; or
   c. SEQ ID NO:35, SEQ ID NO:36 and SEQ ID NO:37, respectively.

6. An antibody or BCMA-binding fragment according to claim 1 comprising a light chain comprising CDR1, CDR2 and CDR3 sequences SEQ ID NO:2, SEQ ID NO:3 and SEQ ID NO:4, respectively, and heavy chain CDR1, CDR2 and CDR3 sequences:
   a. SEQ ID NO:40, SEQ ID NO:41 and SEQ ID NO:42, respectively;
   b. SEQ ID NO:43, SEQ ID NO:44 and SEQ ID NO:45, respectively; or
   c. SEQ ID NO:46, SEQ ID NO:47 and SEQ ID NO:48, respectively.

7. An antibody or BCMA-binding fragment according to claim 1 comprising a light chain comprising CDR1, CDR2 and CDR3 sequences SEQ ID NO:2, SEQ ID NO:3 and SEQ ID NO:4, respectively, and heavy chain CDR1, CDR2 and CDR3 sequences:
   a. SEQ ID NO:51, SEQ ID NO:52 and SEQ ID NO:53, respectively;
   b. SEQ ID NO:54, SEQ ID NO:55 and SEQ ID NO:56, respectively; or
   c. SEQ ID NO:57, SEQ ID NO:58 and SEQ ID NO:59, respectively.

8. The antibody or binding fragment of claim 1 which comprises a light chain variable SEQ ID NO:1.

9. The antibody or binding fragment of claim 1 which comprises a heavy chain variable SEQ ID NO:6, SEQ ID NO:17, SEQ ID NO:28, SEQ ID NO:39, or SEQ ID NO:50.

10. The antibody of claim 1 wherein said antibody is a monoclonal antibody, a chimeric antibody, a diabody, a bispecific antibody, a bispecific Fab$_2$, a bispecific (mab)$_2$, a humanized antibody, an artificially-generated human antibody, bispecific T-cell engager, bispecific NK cell engager, or a single chain antibody.

11. The antibody of claim 1 wherein said antibody is a triomab, knob-in-hole (kih) IgG with common light chain, crossmab, ortho-Fab IgG, DVD-Ig, 2 in 1-IgG, IgG-scFv, sdFv$_2$-Fc, bi-nanobody, tandAb, DART, DART-Fc, scFv-HAS-scFv, or DNL-Fab3.

12. The antibody of claim 1 wherein said antibody is an antibody-drug conjugate.

13. The binding fragment of claim 1 which is a single-chain variable fragment (scFv), Fab fragment, or F(ab')$_2$ fragment.

14. A polypeptide that comprises:
 (A) heavy chain CDR1, CDR2 and CDR3 sequences:
   a. SEQ ID NO: 7, SEQ ID NO: 8 and SEQ ID NO: 9, respectively;
   b. SEQ ID NO: 10, SEQ ID NO: 11 and SEQ ID NO: 12, respectively;
   c. SEQ ID NO: 13, SEQ ID NO: 14 and SEQ ID NO: 15, respectively;
   d. SEQ ID NO: 18, SEQ ID NO: 19 and SEQ ID NO: 20, respectively;
   e. SEQ ID NO: 21, SEQ ID NO: 22 and SEQ ID NO: 23, respectively;
   f. SEQ ID NO: 24, SEQ ID NO: 25 and SEQ ID NO: 26, respectively;
   g. SEQ ID NO: 29, SEQ ID NO: 30 and SEQ ID NO: 31, respectively;
   h. SEQ ID NO: 32, SEQ ID NO: 33 and SEQ ID NO: 34, respectively;
   i. SEQ ID NO: 35, SEQ ID NO: 36 and SEQ ID NO: 37, respectively;
   j. SEQ ID NO: 40, SEQ ID NO: 41 and SEQ ID NO: 42, respectively;
   k. SEQ ID NO: 43, SEQ ID NO: 44 and SEQ ID NO: 45, respectively;
   l. SEQ ID NO: 46, SEQ ID NO: 47 and SEQ ID NO: 48, respectively;
   m. SEQ ID NO: 51, SEQ ID NO: 52 and SEQ ID NO: 53, respectively;
   n. SEQ ID NO: 54, SEQ ID NO: 55 and SEQ ID NO: 56, respectively; or
   o. SEQ ID NO: 57, SEQ ID NO: 58 and SEQ ID NO: 59, respectively; and
 (B) light chain CDR1, CDR2 or CDR3 sequences SEQ ID NO: 2, SEQ ID NO: 3 and SEQ ID NO:4, respectively; and,
 wherein the heavy chain and light chain form an antigen-binding domain which binds BCMA.

15. The polypeptide of claim 14, wherein said polypeptide comprises light chain CDR1, CDR2 and CDR3 sequences of SEQ ID NO:2, SEQ ID NO:3 and SEQ ID NO:4, respectively.

16. A polypeptide according to claim 14 that comprises a light chain variable sequence SEQ ID NO: 1.

17. A polypeptide according to claim 14 that comprises a heavy chain variable sequence SEQ ID NO:6, SEQ ID NO:17, SEQ ID NO:28, SEQ ID NO:39, or SEQ ID NO:50.

18. A method of depleting BCMA-expressing cells in a patient in need thereof comprising administering to the patient a therapeutically effective amount of the antibody or BCMA binding fragment of claim 1.

* * * * *

UNITED STATES PATENT AND TRADEMARK OFFICE
CERTIFICATE OF CORRECTION

| | |
|---|---|
| PATENT NO. | : 11,401,336 B2 |
| APPLICATION NO. | : 16/971925 |
| DATED | : August 2, 2022 |
| INVENTOR(S) | : Mahan Abbasian et al. |

It is certified that error appears in the above-identified patent and that said Letters Patent is hereby corrected as shown below:

In the Claims

Column 81, Claim 11, Line 2, please replace "sdFv$_2$-Fc, bi-nanobody, tandAb, DART, DART-Fc, scFv-" with --scFv$_2$-Fc, bi-nanobody, tandAb, DART, DART-Fc, scFv- --

Signed and Sealed this
Twenty-eighth Day of February, 2023

Katherine Kelly Vidal
*Director of the United States Patent and Trademark Office*

```
                     SEQUENCE LISTING

<160> NUMBER OF SEQ ID NOS: 68

<210> SEQ ID NO 1
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 1

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2
```

Arg Ala Ser Gln Ser Val Ser Ser Asn Leu Ala
1               5                   10

<210> SEQ ID NO 3
<211> LENGTH: 7
<212> TYPE: PRT
<213> ORGANISM: Artificial Sequence
<220> FEATURE:
<223> OTHER INFORMATION: Synthetic peptide

<400> SEQUENCE: 3

Gly Ala Ser Thr Arg Ala Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic peptide

<400> SEQUENCE: 4

Gln Gln Tyr Asn Asn Trp Pro Trp Thr
1               5

<210> SEQ ID NO 5
<211> LENGTH: 321
<212> TYPE: DNA
<213> ORGANISM: Artificial Sequence
<220> FEATURE:
<223> OTHER INFORMATION: Synthetic polynucleotide

<400> SEQUENCE: 5

```
gaaattgtga tgactcagtc gcccgccacc ctgtccgtgt ctccgggaga gcgggccact      60
ctgagctgtc gcgcgtcaca gtcggtgtcc tccaacctcg cctggtacca gcagaagcct     120
ggacaggccc caagactgct gatctacggc gcctccaccc gggccaccgg gattcctgcc     180
cggttctccg gctccggttc cggcactgag ttcaccctga ccatcagctc actgcagtcc     240
gaggacttcg ccgtgtacta ctgccagcag tacaacaact ggccgtggac ctttggccaa     300
ggaaccaagg tcgaaatcaa g                                               321
```

<210> SEQ ID NO 6
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 6

Gln Leu Pro Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Thr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Pro Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ser Ser Ser Tyr Tyr Trp Gly
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Thr Ile Tyr Tyr Ser Gly Ser Thr Tyr Tyr Asn Pro Ser Leu Lys Ser
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

Pro Tyr Tyr Asp Ser Ser Gly Tyr Tyr Tyr
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic peptide

<400> SEQUENCE: 10

Gly Gly Ser Ile Arg Ser Ser Ser Tyr
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide

<400> SEQUENCE: 11

Tyr Tyr Ser Gly Ser
1               5

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Pro Tyr Tyr Asp Ser Ser Gly Tyr Tyr Tyr Tyr
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide

<400> SEQUENCE: 13

Gly Gly Ser Ile Arg Ser Ser Ser Tyr Tyr Trp Gly
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Thr Ile Tyr Tyr Ser Gly Ser Thr Tyr Tyr Asn Pro Ser Leu Lys Ser
1               5                   10                  15

<210> SEQ ID NO 15
<211> LENGTH: 11
<212> TYPE: PRT
<213> ORGANISM: Artificial Sequence
<220> FEATURE:
<223> OTHER INFORMATION: Synthetic peptide

<400> SEQUENCE: 15

Pro Tyr Tyr Asp Ser Ser Gly Tyr Tyr Tyr Tyr
1               5                   10

<210> SEQ ID NO 16
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 16
cagctgccgc tgcaggagtc gggcccagga ctggtgaagc cttcggagac cctgtccctc      60
acctgcactg tttctggtgg ctccatcagg agtagtagtt actactgggg ctggatccgg     120
cagcccccag ggaagggct ggagtggatt gggactatct attatagtgg gagcacctac      180
tacaacccgt ccctcaagag tcgagtcacc atatccgtag acacgtccaa gaaccagctc     240
tccctgaagc tgagctctgt gaccgccgca gacacggctg tgtattactg tgcgagacct     300
tactatgata gtagtggtta ttactactac tggggccagg gcaccctggt caccgtctcc     360
tca                                                                    363

<210> SEQ ID NO 17
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 17

Gln Leu Gln Leu Gln Glu Ser Gly Pro Gly Leu Val Lys Pro Ser Glu

```
                1               5                   10                  15
        Thr Leu Ser Leu Thr Cys Thr Val Ser Gly Gly Ser Ile Ser Ser Ser
                        20                  25                  30
        Asn Ser Tyr Trp Gly Trp Ile Arg Gln Ser Pro Gly Arg Gly Leu Glu
                        35                  40                  45
        Trp Ile Gly Arg Ile Tyr Tyr Ser Gly Ile Thr His Tyr Asn Pro Ser
                50                  55                  60
        Leu Lys Ser Arg Val Thr Ile Ser Val Asp Thr Ser Lys Asn Gln Phe
        65                  70                  75                  80
        Ser Leu Lys Leu Ser Ser Val Thr Ala Ala Asp Thr Ala Val Tyr Tyr
                        85                  90                  95
        Cys Ala Ser Pro Tyr Lys Trp Asn Asp Gly Asn Phe Phe Gly Trp Gly
                        100                 105                 110
        Gln Gly Thr Leu Val Thr Val Ser Ser
                        115                 120
```

<210> SEQ ID NO 18
<211> LENGTH: 7
<212> TYPE: PRT
<213> ORGANISM: Artificial Sequence
<220> FEATURE:
<223> OTHER INFORMATION: Synthetic peptide

<400> SEQUENCE: 18

```
        Ser Ser Asn Ser Tyr Trp Gly
        1               5
```

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide

<400> SEQUENCE: 19

```
        Arg Ile Tyr Tyr Ser Gly Ile Thr His Tyr Asn Pro Ser Leu Lys Ser
        1               5                   10                  15
```

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

```
        Pro Tyr Lys Trp Asn Asp Gly Asn Phe Phe Gly
        1               5                   10
```

<210> SEQ ID NO 21
<211> LENGTH: 9
<212> TYPE: PRT
<213> ORGANISM: Artificial Sequence
<220> FEATURE:
<223> OTHER INFORMATION: Synthetic peptide

<400> SEQUENCE: 21

```
        Gly Gly Ser Ile Ser Ser Ser Asn Ser
        1               5
```

<210> SEQ ID NO 22
<211> LENGTH: 5
<212> TYPE: PRT

```
<213> ORGANISM: Artificial Sequence
<220> FEATURE:
<223> OTHER INFORMATION: Synthetic peptide

<400> SEQUENCE: 22

Tyr Tyr Ser Gly Ile
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide

<400> SEQUENCE: 23

Pro Tyr Lys Trp Asn Asp Gly Asn Phe Phe Gly
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic peptide

<400> SEQUENCE: 24

Gly Gly Ser Ile Ser Ser Ser Asn Ser Tyr Trp Gly
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Synthetic peptide

<400> SEQUENCE: 25

Arg Ile Tyr Tyr Ser Gly Ile Thr His Tyr Asn Pro Ser Leu Lys Ser
1               5                   10                  15

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Pro Tyr Lys Trp Asn Asp Gly Asn Phe Phe Gly
1               5                   10

<210> SEQ ID NO 27
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 27
cagctgcagc tgcaggagtc gggcccagga ctggtgaagc cttcggagac cctgtccctc      60
acctgcactg tctctggtgg ctccatcagc agtagtaatt cctactgggg ctggatccgc     120
cagtccccag ggaggggct ggagtggatt gggaggatct attatagtgg gatcacccac     180
tacaacccgt ccctcaagag tcgagtcacc atatccgtag acacgtccaa gaaccagttc     240
```

```
tccctgaagc tgagctctgt gaccgccgca gacacggctg tgtattactg tgcgagtccg   300
tataagtgga acgacgggaa ttttttttggt tggggccagg gcaccctggt caccgtctcc   360
tca                                                                  363
```

```
<210> SEQ ID NO 28
<211> LENGTH: 120
<212> TYPE: PRT
<213> ORGANISM: Artificial Sequence
<220> FEATURE:
<223> OTHER INFORMATION: Synthetic polypeptide

<400> SEQUENCE: 28
```

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Ser
            20                  25                  30

Asn Tyr Tyr Trp Gly Trp Ile Arg Gln Pro Pro Gly Lys Gly Leu Glu
        35                  40                  45

Trp Ile Gly Asn Ile Tyr Tyr Ser Gly Arg Thr Tyr Tyr Thr Pro Ser
    50                  55                  60

Leu Lys Ser Arg Val Thr Ile Ser Glu Asp Thr Ser Lys Asn Gln Phe
65                  70                  75                  80

Ser Leu Lys Val Arg Ser Val Thr Val Ala Asp Thr Gly Val Tyr Tyr
                85                  90                  95

Cys Ala Arg Pro Asp Tyr Tyr Gly Ser Gly Thr Ile Ala Trp Gly Gln
            100                 105                 110

Gly Thr Leu Val Thr Val Ser Ser
        115                 120
```

```
<210> SEQ ID NO 29
<211> LENGTH: 7
<212> TYPE: PRT
<213> ORGANISM: Artificial Sequence
<220> FEATURE:
<223> OTHER INFORMATION: Synthetic peptide

<400> SEQUENCE: 29
```

```
Asn Ser Asn Tyr Tyr Trp Gly
1               5
```

```
<210> SEQ ID NO 30
<211> LENGTH: 16
<212> TYPE: PRT
<213> ORGANISM: Artificial Sequence
<220> FEATURE:
<223> OTHER INFORMATION: Synthetic peptide

<400> SEQUENCE: 30
```

```
Asn Ile Tyr Tyr Ser Gly Arg Thr Tyr Tyr Thr Pro Ser Leu Lys Ser
1               5                   10                  15
```

```
<210> SEQ ID NO 31
<211> LENGTH: 10
<212> TYPE: PRT
<213> ORGANISM: Artificial Sequence
<220> FEATURE:
<223> OTHER INFORMATION: Synthetic peptide

<400> SEQUENCE: 31
```

```
Pro Asp Tyr Tyr Gly Ser Gly Thr Ile Ala
1               5                   10
```

```
<210> SEQ ID NO 32
<211> LENGTH: 9
<212> TYPE: PRT
<213> ORGANISM: Artificial Sequence
<220> FEATURE:
<223> OTHER INFORMATION: Synthetic peptide

<400> SEQUENCE: 32

Gly Gly Ser Ile Ser Asn Ser Asn Tyr
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic peptide

<400> SEQUENCE: 33

Tyr Tyr Ser Gly Arg
1               5

<210> SEQ ID NO 34
<211> LENGTH: 10
<212> TYPE: PRT
<213> ORGANISM: Artificial Sequence
<220> FEATURE:
<223> OTHER INFORMATION: Synthetic peptide

<400> SEQUENCE: 34

Pro Asp Tyr Tyr Gly Ser Gly Thr Ile Ala
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic peptide

<400> SEQUENCE: 35

Gly Gly Ser Ile Ser Asn Ser Asn Tyr Tyr Trp Gly
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Synthetic peptide

<400> SEQUENCE: 36

Asn Ile Tyr Tyr Ser Gly Arg Thr Tyr Tyr Thr Pro Ser Leu Lys Ser
1               5                   10                  15

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide

<400> SEQUENCE: 37

Pro Asp Tyr Tyr Gly Ser Gly Thr Ile Ala
1               5                   10
```

<210> SEQ ID NO 38
<211> LENGTH: 360
<212> TYPE: DNA
<213> ORGANISM: Artificial Sequence
<220> FEATURE:
<223> OTHER INFORMATION: Synthetic polynucleotide

<400> SEQUENCE: 38

```
cagctgcagc tacaggagtc gggcccagga ctggtgaagc cttcggagac cctgtccctc      60
acctgcactg tctctggtgg ctccatcagc aatagtaatt attactgggg ctggatccgc     120
cagcccccag gaaaggggct ggagtggatt gggaatatct attatagtgg gagaacctat     180
tacaccccgt ccctcaagag tcgcgtcacc atatccgaag acacgtccaa gaaccagttc     240
tccctgaagg tgaggtctgt gaccgtcgca gacacgggtg tgtattactg tgcgagaccg     300
gattactatg gttcggggac tatcgcgtgg ggccagggca ccctggtcac cgtctcctca     360
```

<210> SEQ ID NO 39
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 39

Gln Leu Gln Leu Gln Glu Ser Gly Pro Gly Leu Val Lys Pro Ser Asp
1               5                   10                  15

Thr Leu Ser Leu Thr Cys Thr Val Ser Gly Gly Ser Ile Ser Ser
            20                  25                  30

Asn Ser Tyr Trp Gly Trp Ile Arg Gln Ser Pro Gly Arg Gly Leu Glu
        35                  40                  45

Trp Ile Gly Arg Ile Tyr Tyr Ser Gly Ile Thr His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Ser Pro Tyr Lys Trp Asn Asp Gly Asn Phe Phe Gly Trp Gly
            100                 105                 110

Gln Gly Thr Leu Val Thr Val Ser Ser
        115                 120

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Ser Ser Asn Ser Tyr Trp Gly
1               5

<210> SEQ ID NO 41
<211> LENGTH: 16
<212> TYPE: PRT
<213> ORGANISM: Artificial Sequence
<220> FEATURE:
<223> OTHER INFORMATION: Synthetic peptide

<400> SEQUENCE: 41

Arg Ile Tyr Tyr Ser Gly Ile Thr His Tyr Asn Pro Ser Leu Lys Ser

```
<210> SEQ ID NO 42
<211> LENGTH: 11
<212> TYPE: PRT
<213> ORGANISM: Artificial Sequence
<220> FEATURE:
<223> OTHER INFORMATION: Synthetic peptide

<400> SEQUENCE: 42

Pro Tyr Lys Trp Asn Asp Gly Asn Phe Phe Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide

<400> SEQUENCE: 43

Gly Gly Ser Ile Ser Ser Ser Asn Ser Tyr
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Tyr Tyr Ser Gly Ile
1               5

<210> SEQ ID NO 45
<211> LENGTH: 11
<212> TYPE: PRT
<213> ORGANISM: Artificial Sequence
<220> FEATURE:
<223> OTHER INFORMATION: Synthetic peptide

<400> SEQUENCE: 45

Pro Tyr Lys Trp Asn Asp Gly Asn Phe Phe Gly
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Synthetic peptide

<400> SEQUENCE: 46

Gly Gly Ser Ile Ser Ser Ser Asn Ser Tyr Trp Gly
1               5                   10

<210> SEQ ID NO 47
<211> LENGTH: 16
<212> TYPE: PRT
<213> ORGANISM: Artificial Sequence
<220> FEATURE:
<223> OTHER INFORMATION: Synthetic peptide

<400> SEQUENCE: 47

Arg Ile Tyr Tyr Ser Gly Ile Thr His Tyr Asn Pro Ser Leu Lys Ser
1               5                   10                  15
```

<210> SEQ ID NO 48
<211> LENGTH: 11
<212> TYPE: PRT
<213> ORGANISM: Artificial Sequence
<220> FEATURE:
<223> OTHER INFORMATION: Synthetic peptide

<400> SEQUENCE: 48

Pro Tyr Lys Trp Asn Asp Gly Asn Phe Phe Gly
1               5                   10

<210> SEQ ID NO 49
<211> LENGTH: 363
<212> TYPE: DNA
<213> ORGANISM: Artificial Sequence
<220> FEATURE:
<223> OTHER INFORMATION: Synthetic polynucleotide

<400> SEQUENCE: 49
cagctgcagc tgcaggagtc gggcccagga ctggtgaagc cttcggacac cctgtccctc      60
acctgcactg tctctggtgg ctccatcagc agtagtaatt cctactgggg ctggatccgc     120
cagtccccag ggagggggct ggagtggatt gggaggatct attatagtgg gatcacccac     180
tacaacccgt ccctcaagag tcgagtcacc atatccgtag acacgtccaa gaaccagttc     240
tccctgaagc tgagctctgt gactgccgcg gacacggctg tgtattactg tgcgagtccg     300
tataagtgga cgacgggaa ttttttttggt tggggccagg gcaccctggt caccgtctcc     360
tca                                                                   363

<210> SEQ ID NO 50
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 50

Gln Leu Gln Leu Gln Glu Ser Gly Pro Gly Leu Val Lys Pro Ser Glu
1               5                   10                  15

Thr Leu Ser Leu Thr Cys Thr Val Ser Gly Ser Ser Ile Ser Arg Ser
            20                  25                  30

Asn Tyr Tyr Trp Gly Trp Ile Arg Gln Pro Pro Gly Lys Gly Leu Glu
        35                  40                  45

Trp Ile Gly Thr Phe Tyr Tyr Ser Gly Thr Thr Tyr Tyr Asn Pro Ser
    50                  55                  60

Leu Lys Ser Arg Val Thr Ile Ser Glu Asp Thr Ser Lys Lys Gln Leu
65                  70                  75                  80

Ser Leu Asn Leu Arg Ser Val Thr Ala Ala Asp Thr Ala Val Tyr Tyr
                85                  90                  95

Cys Ala Arg Pro Ser Gly Tyr Thr Thr Ser Trp Gly Gln Gly Thr Leu
            100                 105                 110

Val Thr Val Ser Ser
        115

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 51

Arg Ser Asn Tyr Tyr Trp Gly
1               5

<210> SEQ ID NO 52
<211> LENGTH: 16
<212> TYPE: PRT
<213> ORGANISM: Artificial Sequence
<220> FEATURE:
<223> OTHER INFORMATION: Synthetic peptide

<400> SEQUENCE: 52

Thr Phe Tyr Tyr Ser Gly Thr Thr Tyr Tyr Asn Pro Ser Leu Lys Ser
1               5                   10                  15

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Pro Ser Gly Tyr Thr Thr Ser
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Gly Ser Ser Ile Ser Arg Ser Asn Tyr
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic peptide

<400> SEQUENCE: 55

Tyr Tyr Ser Gly Thr
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Pro Ser Gly Tyr Thr Thr Ser
1               5

<210> SEQ ID NO 57
<211> LENGTH: 12
<212> TYPE: PRT
<213> ORGANISM: Artificial Sequence
<220> FEATURE:
<223> OTHER INFORMATION: Synthetic peptide
```

<400> SEQUENCE: 57

Gly Ser Ser Ile Ser Arg Ser Asn Tyr Tyr Trp Gly
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Synthetic peptide

<400> SEQUENCE: 58

Thr Phe Tyr Tyr Ser Gly Thr Thr Tyr Tyr Asn Pro Ser Leu Lys Ser
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Pro Ser Gly Tyr Thr Thr Ser
1               5

<210> SEQ ID NO 60
<211> LENGTH: 351
<212> TYPE: DNA
<213> ORGANISM: Artificial Sequence
<220> FEATURE:
<223> OTHER INFORMATION: Synthetic polynucleotide

<400> SEQUENCE: 60
cagctgcagc tgcaggagtc gggcccagga ctggtgaagc cttcggagac cctgtccctc      60
acctgcactg tctctggaag ctccatcagc aggagtaatt actactgggg ctggatccgc     120
cagcccccag ggaagggtct ggagtggatt gggactttct attatagtgg gaccacctac     180
tacaacccgt ccctcaagag tcgagtcacc atatccgaag acacgtccaa gaaacagtta     240
tccctgaacc tgaggtctgt gaccgccgca gacacggctg tgtattactg tgcgagacct     300
tccggatata ccaccagctg gggccagggc accctggtca ccgtctcctc a              351

<210> SEQ ID NO 61
<211> LENGTH: 36
<212> TYPE: PRT
<213> ORGANISM: Homo sapiens

<400> SEQUENCE: 61

Pro Glu Pro Cys Pro Asp Ser Asp Phe Leu Leu Trp Ile Leu Ala Ala
1               5                   10                  15

Val Ser Ser Gly Leu Phe Phe Tyr Ser Phe Leu Leu Thr Ala Val Ser
                20                  25                  30

Leu Ser Lys Met
        35

<210> SEQ ID NO 62
<211> LENGTH: 29
<212> TYPE: PRT
<213> ORGANISM: Homo sapiens

<400> SEQUENCE: 62

Pro Asp Ser Asp Phe Leu Leu Trp Ile Leu Ala Ala Val Ser Ser Gly

-continued

```
                1               5                  10                 15
Leu Phe Phe Tyr Ser Phe Leu Leu Thr Ala Val Ser Leu
                20                  25

<210> SEQ ID NO 63
<211> LENGTH: 23
<212> TYPE: PRT
<213> ORGANISM: Homo sapiens

<400> SEQUENCE: 63

Phe Leu Leu Trp Ile Leu Ala Ala Val Ser Ser Gly Leu Phe Phe Tyr
1               5                  10                  15

Ser Phe Leu Leu Thr Ala Val
                20

<210> SEQ ID NO 64
<211> LENGTH: 21
<212> TYPE: PRT
<213> ORGANISM: Homo sapiens

<400> SEQUENCE: 64

Phe Leu Leu Trp Ile Leu Ala Ala Val Ser Ser Gly Leu Phe Phe Tyr
1               5                  10                  15

Ser Phe Leu Leu Thr
                20

<210> SEQ ID NO 65
<211> LENGTH: 26
<212> TYPE: PRT
<213> ORGANISM: Mus musculus

<400> SEQUENCE: 65

Phe Leu Leu Trp Ile Leu Val Ala Val Ser Leu Gly Leu Phe Phe Tyr
1               5                  10                  15

Ser Phe Leu Val Ser Ala Val Ser Leu Ser
                20                  25

<210> SEQ ID NO 66
<211> LENGTH: 29
<212> TYPE: PRT
<213> ORGANISM: Homo sapiens

<400> SEQUENCE: 66

Thr Leu Val Val Gly Val Val Gly Gly Leu Leu Gly Ser Leu Val Leu
1               5                  10                  15

Leu Val Trp Val Leu Ala Val Ile Cys Ser Arg Ala Ala
                20                  25

<210> SEQ ID NO 67
<211> LENGTH: 21
<212> TYPE: PRT
<213> ORGANISM: Homo sapiens

<400> SEQUENCE: 67

Val Gly Val Val Gly Gly Leu Leu Gly Ser Leu Val Leu Leu Val Trp
1               5                  10                  15

Val Leu Ala Val Ile
                20

<210> SEQ ID NO 68
<211> LENGTH: 26
<212> TYPE: PRT
```

<213> ORGANISM: Homo sapiens

<400> SEQUENCE: 68

```
Phe Gln Thr Leu Val Val Gly Val Val Gly Gly Leu Leu Gly Ser Leu
1               5                   10                  15
Val Leu Leu Val Trp Val Leu Ala Val Ile
            20                  25
```